United States Patent
Georges

(10) Patent No.: US 10,849,984 B2
(45) Date of Patent: *Dec. 1, 2020

(54) IMMUNOGENIC COMPOUND

(71) Applicant: Altimmune UK Limited

(72) Inventor: Bertrand Georges, London (GB)

(73) Assignee: Altimmune UK Limited, Leeds (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/595,311

(22) Filed: Oct. 7, 2019

(65) Prior Publication Data

US 2020/0038519 A1    Feb. 6, 2020

Related U.S. Application Data

(63) Continuation of application No. 15/968,839, filed on May 2, 2018, now Pat. No. 10,434,183, which is a continuation of application No. 15/100,800, filed as application No. PCT/GB2014/053577 on Dec. 2, 2014, now Pat. No. 9,962,453.

(30) Foreign Application Priority Data

Dec. 2, 2013 (GB) .................................. 1321242.8

(51) Int. Cl.
A61K 47/62 (2017.01)
A61K 47/64 (2017.01)

(52) U.S. Cl.
CPC .................................. *A61K 47/646* (2017.08)

(58) Field of Classification Search
None
See application file for complete search history.

(56) References Cited

U.S. PATENT DOCUMENTS

| | | | |
|---|---|---|---|
| 4,801,575 A | 1/1989 | Pardridge | |
| 5,294,605 A | 3/1994 | Houghten et al. | |
| 7,968,562 B2 | 6/2011 | Skwierczynski et al. | |
| 8,598,192 B2 | 12/2013 | Kshirsagar et al. | |
| 8,916,162 B2 | 12/2014 | Zdanovsky | |
| 2003/0199538 A1 | 10/2003 | Skwierczynski et al. | |
| 2006/0013820 A1 | 1/2006 | Bonnet et al. | |
| 2008/0193474 A1 | 8/2008 | Griesgraber et al. | |
| 2008/0275077 A1 | 11/2008 | Skwierczynski et al. | |
| 2009/0105295 A1 | 4/2009 | Kshirsagar et al. | |
| 2010/0183650 A1 | 7/2010 | Bonnet et al. | |
| 2010/0183708 A1 | 7/2010 | Bonnet et al. | |
| 2011/0136801 A1 | 6/2011 | Isobe et al. | |
| 2012/0034259 A1 | 2/2012 | Bonnet et al. | |
| 2012/0148660 A1 | 6/2012 | Carson et al. | |
| 2012/0294885 A1 | 11/2012 | David et al. | |
| 2012/0315293 A1 | 12/2012 | Bonnet et al. | |
| 2012/0328642 A1 | 12/2012 | Zdanovsky | |
| 2015/0112042 A1 | 4/2015 | Bonnet et al. | |

FOREIGN PATENT DOCUMENTS

| | | |
|---|---|---|
| WO | 8800834 A1 | 2/1988 |
| WO | 9201462 A1 | 2/1992 |
| WO | 03045391 A1 | 6/2003 |
| WO | 2004032829 A2 | 4/2004 |
| WO | 2005048945 A2 | 6/2005 |
| WO | 2005099752 A2 | 10/2005 |
| WO | 2006116475 A2 | 11/2006 |
| WO | 2009027688 A1 | 3/2009 |
| WO | 2010048520 A1 | 4/2010 |
| WO | 2011068233 A1 | 6/2011 |
| WO | 2011103465 A2 | 8/2011 |
| WO | 2012024284 A1 | 2/2012 |
| WO | 2012090002 A1 | 7/2012 |
| WO | 2012167088 A1 | 12/2012 |

OTHER PUBLICATIONS

Border, WA, et al., Induction of membranous nephropathy in rabbits by administration of an exogenous cation inc antigen. J. Clin. Invest., Feb. 1982;69(2):451-461.
ChemBlink web page, http://www.chemblink.com/products/83461-56-7.htm, downloaded Jun. 12, 2017.
Chruszcz, M, et al., Serum albumins—unusual allergens, Biocheim Biophys Acat, Dec. 2013;1830(12):5375-5381.
Cote, SC, et al., Dectin-1/tlr2 and nod2 agonists render dendritic cells susceptible to infection by x4-using hiv-1 and promote cis-infection of cd4+ t cells, PLoS One, Jul. 2, 2013;8(7):e67735.
Eurasian Search Report dated Jan. 11, 2017, which issued during prosecution of Eurasian Application No. 201691146.
Genin, MJ, et al., Imidazopyridine and pyrazolopiperidine derivatives as novel inhibitors of serine palmitoyl transferase, J Med Chem, Jun. 23, 2016;59(12):5904-5910.
Higgins, SC, et al., Tlr, nlr agonists, and other immune modulators as infectious disease vaccine adjuvants, Curr Infect Dis Rep, Jan. 2010;12(1):4-12.
International Search Report dated May 29, 2015, which issued during prosecution of International Application No. PCT/GB2014/053577.
Kaczanowska, S, et al., Tlr agonists: our best frenemy in cancer immunotherapy, J Leukoc Biol, 2013;93(6):847-864.

(Continued)

*Primary Examiner* — Fred H Reynolds
(74) *Attorney, Agent, or Firm* — Koren Anderson

(57) ABSTRACT

The present application relates to an immunostimulatory compound comprising an immunostimulant portion and a peptide portion. The peptide portion is not a disease-associated immunogen. Furthermore, the peptide portion has an amino acid sequence in which 75% or less of the amino acid residues are hydrophobic and/or has an isoelectric point of 5 or greater. The compounds of the invention address the problem of systemic distribution of immunostimulants causing unwanted side effects. The inventors have found that the physicochemical properties of the immunostimulant can be controlled by covalent linkage to a peptide. Further physicochemical properties may be modified in a useful manner by incorporating additional features.

19 Claims, 6 Drawing Sheets
Specification includes a Sequence Listing.

(56) References Cited

OTHER PUBLICATIONS

Mattner, F, et al., Vaccination with poly-I-arginine as immunostimulant for peptide faccines: induction of potent and long-lasting t-cell responses against cancer antigens, Cancer Res, Mar. 1, 2002;62(5):1477-1480.

Prost, LR, et al., Non-carbohydrate glycomimetics and glycoprotein surrogates as de-sign antagonists and agonists, ACS Chem Biol, Sep. 21, 2012;7(9):1603-1608.

Shukla, NM, et al., Toward Self-Adjuvanting Subunit Vaccines: Model Peptide and Protein Antigens Incorporating Covalently Bound Toll-Like Receptor-7 Agonistic Imidazoquinolines, Bioorganic & Medicinal Chemistry Letters, Jun. 1, 2011;21(11)3232-3236.

The catalog page for muramyldipeptide from Invivogen, http://www.invivogen.com/mdp, downloaded Jun. 12, 2017.

The GenBank entry AAA51411, entered 2002.

The invivogen web page, http://www.invivogen.com/fulfurman, downloaded Jun. 12, 2017.

Tocris product information, cat#5901, downloaded Jun. 12, 2017.

United Kingdom Search Report dated Aug. 7, 2014, which issued during prosecution of GB Application No. 1321242.8.

Van Haren, SD, et al., Age-specific adjuvant synergy: dual tlr7/8 and mincle activation of human newborn dendritic cells enables th1 polarization, J Immunol, Dec. 1, 2016;197(11):4413-4424.

Willats, WG, Phage display: practicalities and prospects, Plant Mol Biol, Dec. 2002;50:837-854.

Wille-Reece, U, et al., HIV Gag protein conjugated to a Toll-like receptor 7/8 agonist improves the magnitude and quality of Th1 and CD8+ T cell responses in nonhuman primates, Proc Natl Acad Sci USA, Oct. 18, 2005;102(42)15190-4.

Written Opinion of the International Searching Authority dated May 29, 2015, which issued during prosecution of International Application No. PCT/GB2014/053577.

Zhao,R, et al., Purification of Glutathione by Immobilized Metal Ion Affinity Chromatography with Thiourea as the Ligand, Chromatographia, Feb. 2009;69(7-8):755-759.

IMMUNOGENIC COMPOUND

RELATED APPLICATIONS AND INCORPORATION BY REFERENCE

The present application is a continuation application of U.S. Ser. No. 15/968,839 filed 2 May 2018, which is a continuation application of U.S. Ser. No. 15/100,800 filed Jun. 1, 2016 (U.S. Pat. No. 9,962,453), which was filed pursuant to 35 U.S.C. § 371 as an U.S. National Phase Application of International Patent Application No. PCT/GB2014/053577, which was filed on Dec. 2, 2014, claiming the benefit of priority to United Kingdom Patent Application No. GB 1321242.8 filed on Dec. 2, 2013. The International Application was published as WO 2015/082905 on Jun. 11, 2015. The content of each of the aforementioned Patent Applications is incorporated herein by reference in its entirety.

SEQUENCE LISTING

The application contains a Sequence Listing which has been submitted electronically in ASCII format and is hereby incorporated by reference in its entirety. The ASCII copy, created 7 Jul. 2020, is named "IPF07US3 ST25" and has a file size of 30.8 KB.

FIELD OF THE INVENTION

The present invention relates to novel immunostimulatory compounds and the use of the compounds in medicine, particularly as adjuvants for vaccines.

BACKGROUND TO THE INVENTION

Live attenuated or inactivated bacteria and viruses have formed the basis of many successful vaccines. The whole virus or bacteria approach remains the most effective means of generating protective immunity by vaccination. However, these vaccines can be associated with mild to severe side effects. Furthermore, rare cases of vaccine-associated disease can result from reversion of an attenuated virus to the virulent form. Advances in genomics, molecular biology and immunology have facilitated the identification, recombinant expression and immunological characterization of protective antigens from infectious organisms, permitting a more rational approach to vaccine design. Purified native or recombinant peptides, proteins or polysaccharides (linked to carrier proteins) now provide a much cleaner, safer and more immunologically defined alternative to live or killed whole cell vaccines. However, these "purer" vaccine preparations lack the danger signals required to activate innate immune responses and must therefore be delivered with potent adjuvants or delivery systems in order to generate protective adaptive immune responses.

Vaccine adjuvants can be used for multiple purposes, such as for example to increase efficacy, reduce the amount of antigen and/or number of doses required, enhance the rapidity and/or intensity of response, increase the breadth of response (e.g. to protect against multiple epitopes, such as might arise from pathogen evolution), and to enhance the duration of response and/or ability to prime for later response (memory). For example, recent increased interest in adjuvants concerns their use in cases of poor immunogens (such as pandemic influenza vaccine H5N1), insufficient manufacturing capacity (dose sparing) and broader specific immune response (mutating viruses). Adjuvants are also potentially important for vaccination of the elderly (who may be subject to immunoscenescence mechanisms), children (with low pre-existing immunity), and immunocompromised individuals with low capacity to respond to vaccination. There are certain challenges associated with the use of adjuvants to stimulate the immune system in combination with the administration of a vaccine. Primarily, there is the importance of co-delivering and maintaining the antigen component and the immunostimulant component of the vaccine at the injection site, at least until contacting an immune cell. This is important to maximise the benefit of the adjuvant, but can also be necessary to reduce toxicity. Immunostimulants, such as agonists of Toll-like receptors (TLRs) or Nod-like receptors (NLRs), are typically small molecules which are readily transported throughout the body. They can therefore give rise to unacceptable clinical side effects due to systemic reactions, such as the triggering of autoimmune diseases.

It is known to covalently link an immunostimulant to a desired antigen, in order to ensure that both the antigen and the immunostimulant can be presented together to an immune cell. For example, WO 2012/167088 describes an "immune response modifier" covalently linked to an antigen by means of a linker comprising polyethylene glycol. WO 2004/032829 describes an immunostimulatory composition comprising an immune response modifier portion 'paired with' an antigenic portion, where the pairing may be by means of covalent linkage. WO 2006/116475 describes an immune response modifier covalently linked to an antigenic peptide.

It is also known to modify the chemical structure of an immunostimulant to aid in delivery. For example, WO 2012/024284 and WO 2010/048520 describe immunostimulants covalently linked to lipids, either to enable formulation or to improve bioavailability.

SUMMARY OF THE INVENTION

The present inventors have addressed the problem of systemic distribution of immunostimulants causing unwanted side effects. The inventors have found that the physicochemical properties of the immunostimulant can be controlled by covalent linkage to a peptide. Further physicochemical properties may be modified by incorporating additional features.

The present invention therefore provides a compound comprising an immunostimulant portion and a peptide portion, wherein the peptide portion:
(a) is not a disease-associated antigen;
(b) has an amino-acid sequence in which 75% or less of the amino acid residues are hydrophobic; and/or
(c) has an isoelectric point of 5 or greater.

The invention also provides a compound comprising an immunostimulant portion, a peptide portion, and a vector portion.

The invention also provides: the use of a peptide to reduce the solubility of an immunostimulant in extracellular fluid, wherein the peptide is covalently linked to the immunostimulant; a compound of the invention for use in a method of treating the human or animal body by therapy; a pharmaceutical composition comprising a compound of the invention and a pharmaceutically acceptable carrier or diluent; a pharmaceutical composition of the invention for use in a method of treating the human or animal body by therapy; a pharmaceutical composition of the invention for use in stimulating an immune response of an animal or human to an antigen; and the compound of the invention for use in the manufacture of a medicament for stimulating an immune response to an antigen.

DETAILED DESCRIPTION OF THE INVENTION

Figure 1:
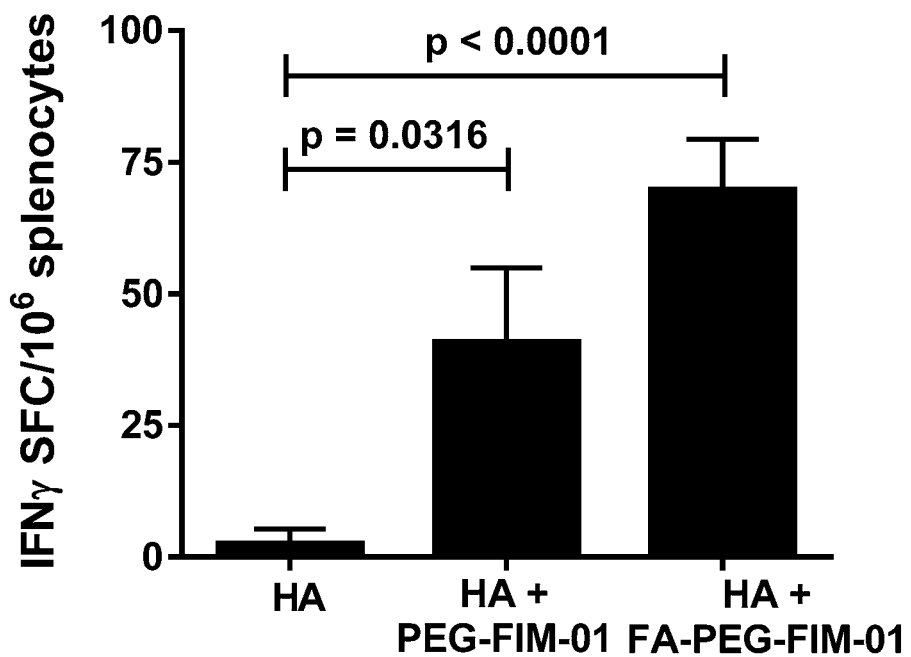
FIG. 1 depicts improvement of the T cell immune response against a recombinant protein in combination with different immunostimulatory-peptide conjugates, as demonstrated in the Examples. Female BALB/c mice were immunised with 12.5 μg HA alone or in addition with 13.2 μg PEG-FIM-01 or 15 μg PEG-FIM-01 (equimolar doses). Bars represent the mean number of spot forming cells as measured in the IFN-g ELISpot assay. Numbers of IFNγ SFC per $10^6$ splenocytes were counted. Bars represent mean±SEM responses to HA. Statistical analysis was based on a Student's T test.
Figure 2:
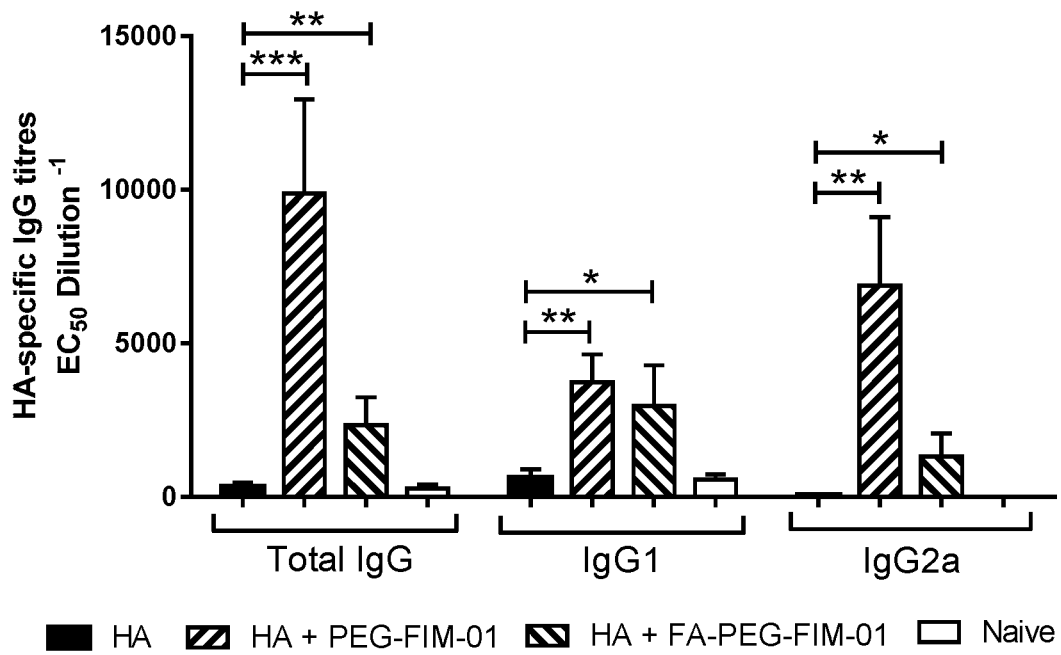
FIG. 2 depicts improvement of the humoral response against a recombinant protein in combination with different immunostimulatory-peptide conjugates, as demonstrated in the Examples. Female BALB/c mice were immunised with 12.5 μg HA alone or in addition with 13.2 μg PEG-FIM-01 or 15 μg PEG-FIM-01 (equimolar doses). Non-immunised animal were used as negative controls. Data is shown as the mean+standard error of the mean EC50 dilution-1. Log-transformed data was used for statistical analysis using a Student's T test where *<0.05, <0.01 and *<0.001.
Figure 3:
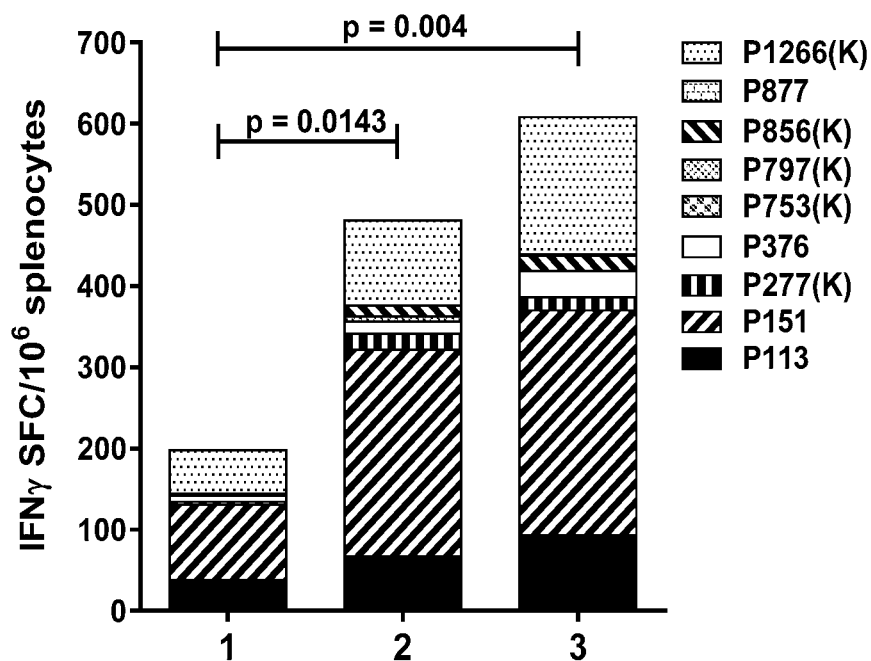
FIG. 3 depicts improvement of the immunogenicity of a peptide vaccine in combination with different immunostimulatory peptide conjugates, as demonstrated in the Examples. Female BALB/c mice were immunised with (1) FP-02.2 (25 mcg/peptide) alone, (2) FP-02.2 (25 mcg/peptide)+FA-FIM-01 (5 mcg), (3) FP-02.2 (25 mcg/peptide)+FA-PEG-FIM-01 (5 mcg). Bars represent the cumulative mean number of spot forming cells for each peptide contained in the FP-02.2 vaccine as measured in the IFN-g ELISpot assay. Statistical analysis was based on a Student's T test.
Figure 4:
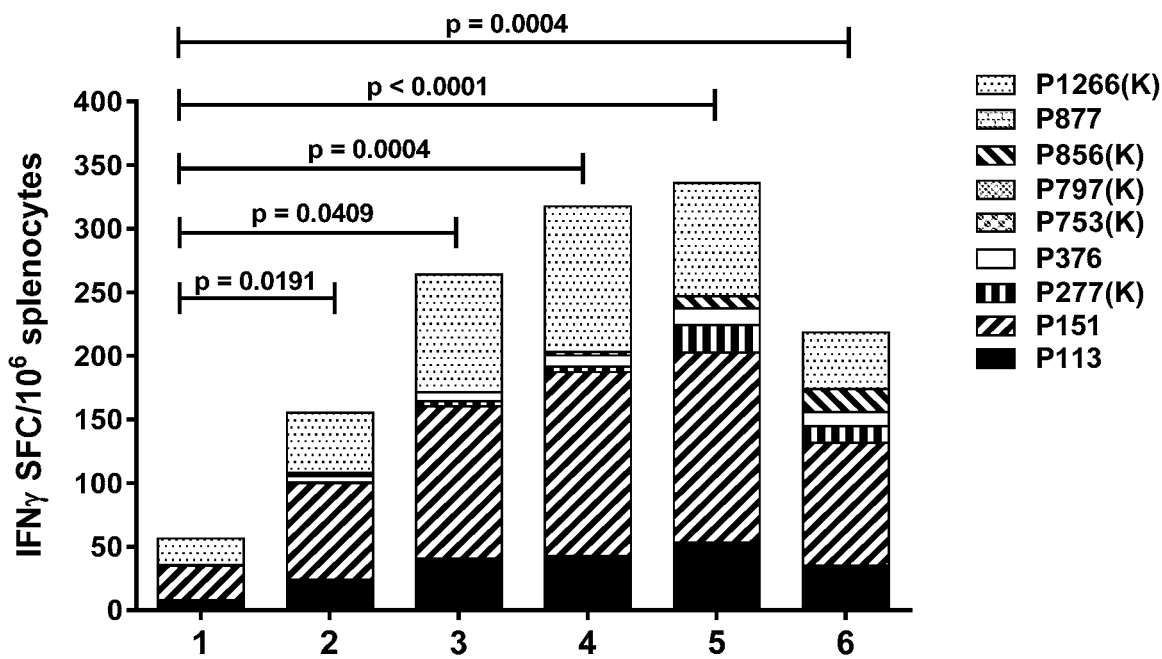
FIG. 4 depicts improved vaccine immunogenicity in the presence of an immunostimulatory peptide conjugate at different doses, as demonstrated in the Examples. Female BALB/c mice were immunised with FP-02.2 (25 mcg/peptide) alone or in combination with FA-PEG-FIM-01 at doses varying from (1) 0 mcg, (2) 0.5 mcg, (3) 1.58 mcg, (4) 5 mcg (5) 15.8 mcg and (6) 50 mcg. Bars represent the cumulative mean number of spot forming cells for each peptide contained in the FP-02.2 vaccine as measured in the IFN-g ELISpot assay. Statistical analysis was based on a Student's T test.
Figure 5:
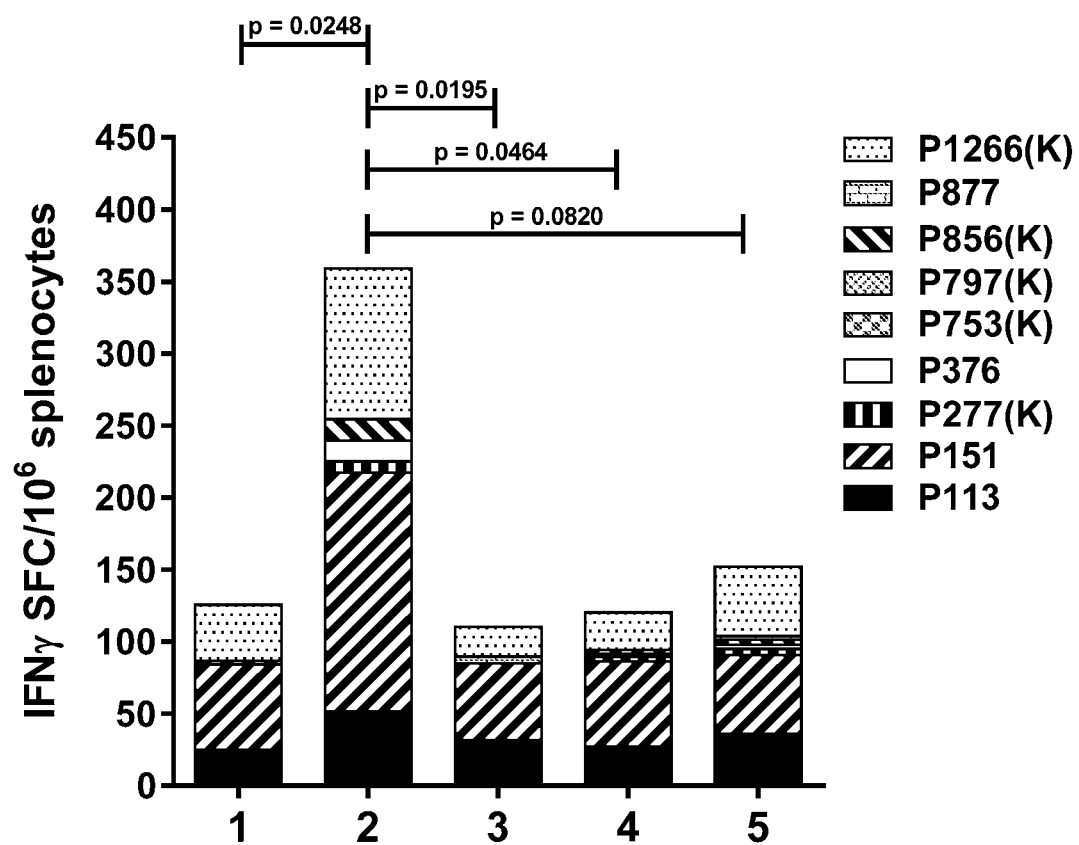
FIG. 5 depicts superior adjuvanticity of the immunostimulatory peptide conjugate compared to a free immune stimulant counterpart R848, as demonstrated in the Examples. Female BALB/c mice were immunised with (1) FP-02.2 (25 mcg/peptide), (2) FP-02.2 (25 mcg/peptide)+FA-PEG-FIM-01 (15 mcg), (3) FP-02.2 (25 mcg/peptide)+R848 (1.5 mcg), (4) FP-02.2 (25 mcg/peptide)+R848 (10 mcg) and (5) FP-02.2 (25 mcg/peptide)+R848 (50 mcg). Bars represent the cumulative mean number of spot forming cells for each peptide contained in the FP-02.2 vaccine as measured in the IFN-g ELISpot assay. Statistical analysis was based on a Student's T test.
Figure 6:
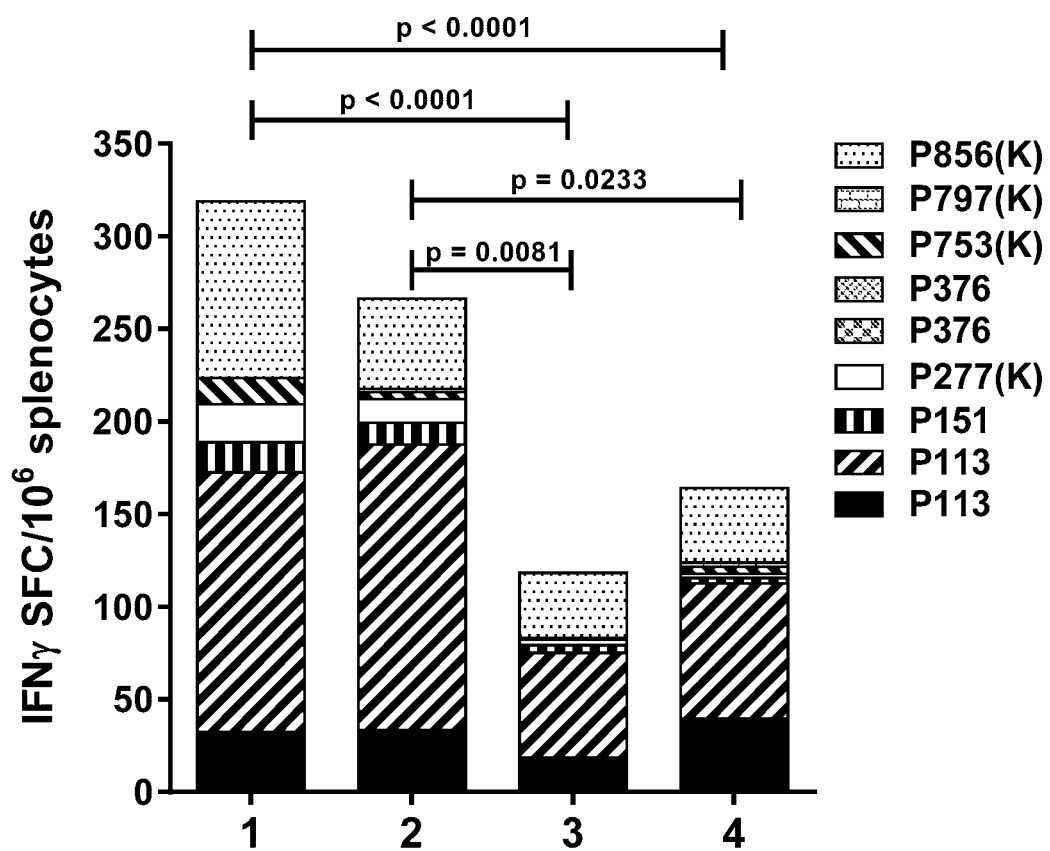
FIG. 6 depicts the key role played by the peptide portion in the vaccine adjuvanticity of immunostimulatory-peptide conjugates, as demonstrated in the Examples. Female BALB/c mice were immunised with (1) FP-02.2 (25 mcg/peptide)+FA-PEG-FIM-01 (15 mcg), (2) FP-02.2 (25 mcg/peptide)+PEG-FIM-01 (13.15 mcg) (3), FP-02.2 (25 mcg/peptide)+RKL-PEG-FIM-01 (4.3 mcg) (4) or FP-02.2 (25 mcg/peptide)+R848 (1.5 mcg) corresponding to equimolar doses. Bars represent the cumulative mean number of spot forming cells for each peptide contained in the FP-02.2 vaccine as measured in the IFN-g ELISpot assay. Statistical analysis was based on a Student's T test.
Figure 7:
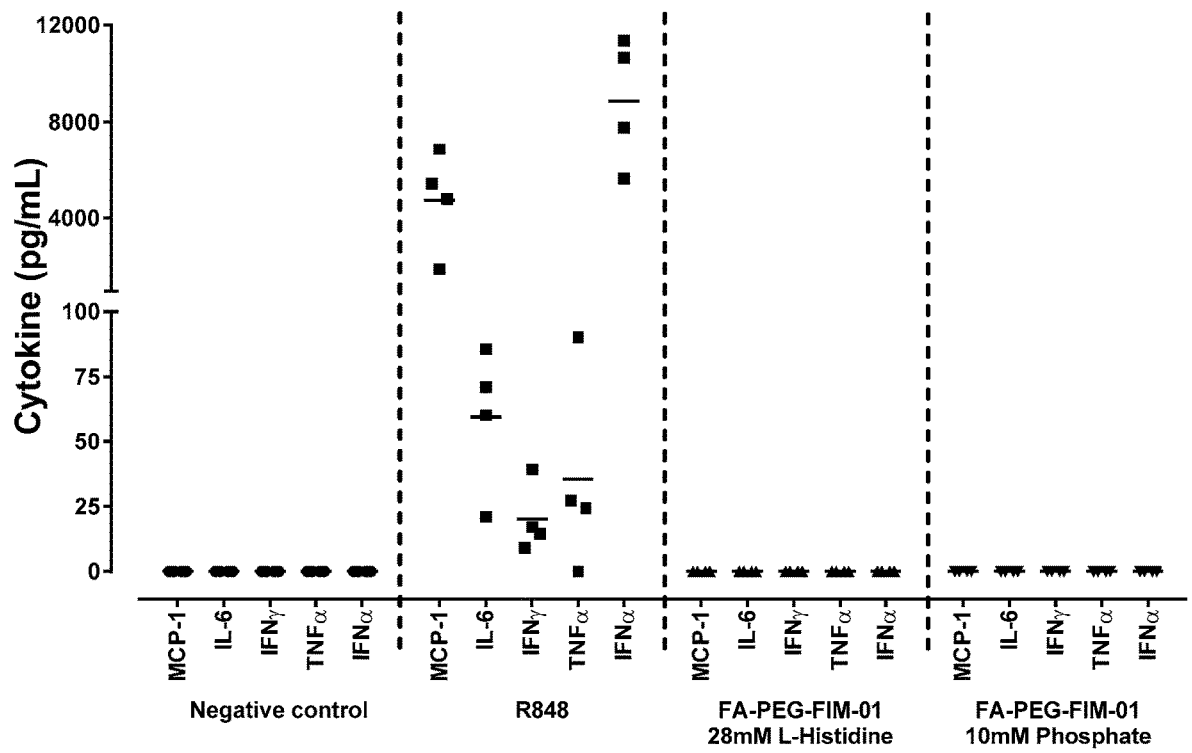
FIG. 7 depicts the absence of systemic pro-inflammatory responses with an immunostimulatory peptide conjugate as opposed to a free immune stimulant R848, as demonstrated in the Examples. Female BALB/c mice were injected on a single occasion with (1) the 28 mM L-Histidine vehicle, (2) R848 (1.5 mcg) in 28 mM L-Histidine, (3) FA-PEG-FIM-01 (15 mcg) in 28 mM L-Histidine, (3) FA-PEG-FIM-01 (15 mcg) in Phosphate 10 mM (n=4 per group). (R848 and FA-PEG-FIM-01 were delivered at equimolar doses). Graphs display peak cytokine concentrations for individual samples at 1 hour (IL-6, TNF-α, IFNα) or 4 hours (MCP-1, IFN-gamma) for each immunisation group. IL-10 and IL-12p70 were negative for all samples, data not shown. Statistical analysis was based on a Student's T test.

The present invention provides immunostimulatory compounds comprising an immunostimulant coupled to a peptide, optionally via a flexible spacer. The peptide may be further coupled to a vector. The various moieties within the compounds of the invention are coupled via covalent linkage.

The compounds of the invention are of interest for use in vaccines to prevent infectious diseases, such as viral, bacterial, parasitic and fungal infections. The compounds are also of interest in the field of immunotherapeutics, including the treatment of infection, the stimulation of immunity to cancer cells, the down-regulation of polypeptide hormones and the control of inappropriate immune responses such as anaphylaxis, allergy and/or autoimmunity.

Immunostimulant Portion

The compounds of the invention comprise an immunostimulant portion. As used herein, the term "immunostimulant portion" refers to a portion of the compound which provides the compound with immunostimulatory activity. For example, the immunostimulant portion may be derived from a known immunostimulant by removal of a hydrogen atom, the covalent bond to hydrogen being replaced by the covalent linkage to the remainder of the compound.

As used herein, the term "immunostimulatory activity" refers to the ability to stimulate the immune system of an individual. The immunostimulant may promote strong and prolonged cell-mediated immunity, preferably CD8+ T cell-mediated immunity. Alternatively or additionally, the immunostimulant may be capable of activating human dendritic cells, breaking tolerance to an antigen, and/or countering the effects of T-regulatory cells.

Preferably, the immunostimulant portion has a molecular weight of 5000 Da or less. More preferably, the molecular weight is 2000 Da or less, 1000 Da or less, 900 Da or less, 800 Da or less, 750 Da or less, 700 Da or less, 650 Da or less, 600 Da or less, 550 Da or less, 500 Da or less, 450 Da or less, 400 Da or less, 350 Da or less, 300 Da or less, or 250 Da or less. The immunostimulant portion may have a molecular weight which is at least 50 Da, at least 100 Da, at least 150 Da, at least 200 Da, at least 250 Da, at least 300 Da, at least 400 Da, at least 500 Da, at least 600 Da, at least 700 Da, at least 800 Da, at least 900 Da, or at least 1000 Da. Any endpoint may be combined with any other endpoint to define a range of suitable molecular weights. For example, the immunostimulant portion may have a molecular weight of from 100 to 600 Da, or from 500 to 900 Da.

Preferably, the immunostimulant portion is a non-nucleotide immunostimulant. For example, the immunostimulant portion may be a structure designed to mimic the shape and/or functionality of a nucleotide immunostimulant, or may have an unrelated structure and function.

Suitable immunostimulants may be categorised according to the receptors for which they act as agonists. For example, the immunostimulant may be selected from a Toll-like receptor (TLR) agonist, such as an agonist of TLR3, TLR4, TLR7, TLR8, or TLR9; a NOD-like receptor (NLR) agonist, such as an agonist of NOD-1 or NOD-2; and an agonist of one or more of DC-sign, Dectin-1, Dectin-2, Mincle, DDX41 and STRING. Preferably the immunostimulant portion is derived from an agonist of at least one of TLR 7, TLR8 and NOD-2.

Preferably, the immunostimulant portion comprises at least one of an imidazopyridine moiety, an imidazoquinoline moiety, a muramyl-dipeptide moiety, a muramyl-tripeptide moiety, and a glutamyl-meso-diaminopimelic acid moiety.

Imidazopyridine-based structures, and particularly imidazoquinoline-based structures, have shown activity as agonists of TLR7 and/or TLR8. Exemplary imidazoquinoline-based immunostimulants include the pharmaceutical compounds resiquimod, imiquimod and guardiquimod.

Muramyl di and tri-peptides have shown activity as agonists of NOD2. Exemplary immunostimulants include N-acetylmuramyl-L-alanyl-D-isoglutamine, N-glycolylmuramyl-L-alanyl-D-isoglutamine, N-acetylmuramyl-L-alanyl-D-glutamine n-butyl ester (murabutide), N-acetylmuramyl-L-alanyl-D-isoglutaminyl-L-lysine, N-acetylmuramyl-L-alanyl-γ-D-glutamyl-meso-diaminopimelic acid, N-acetyl-D-glucosaminyl-(β-1,4)-N-acetylmuramyl-L-alanyl-D-isoglutamine, 6-O-stearoyl-N-acetylmuramyl-L-alanyl-D-isoglutamine, mifamurtide, and N-acetylmuramyl-L-alanyl-D-isoglutaminyl-L-alanine cholesterol ester.

Glutamyl-meso-diaminopimelic acid-based structures have shown activity as agonists of NOD1. Exemplary immunostimulants include γ-D-glutamyl-meso-diaminopimelic acid, L-alanyl-γ-D-glutamyl-meso-diaminopimelic acid, N-acetylmuramyl-L-alanyl-γ-D-glutamyl-meso-diaminopimelic acid and lauroyl-γ-D-glutamyl-meso-diaminopimelic acid.

Preferably, the immunostimulant portion has a structure according to one of Formula (I), Formula (IIa), Formula (IIb), Formula (Ma), Formula (Mb) or Formula (IV):

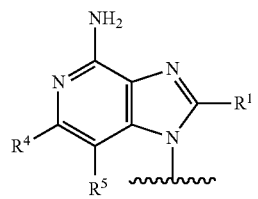
(I)

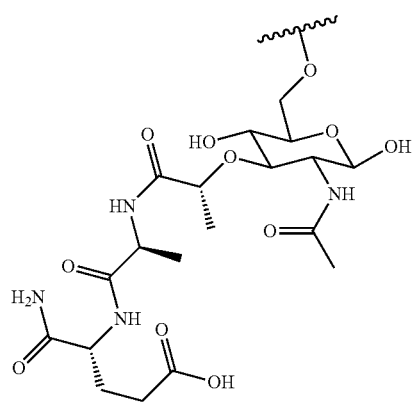
(IIa)

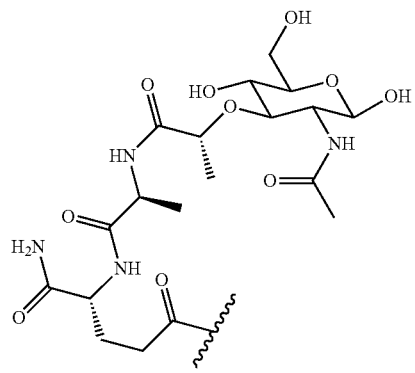
(IIb)

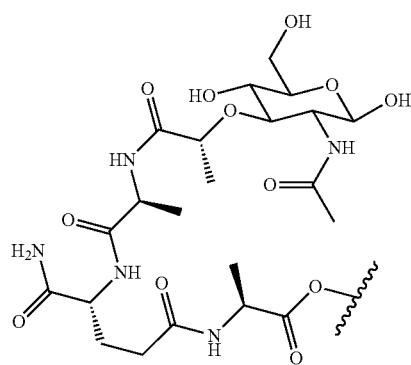
(IIIa)

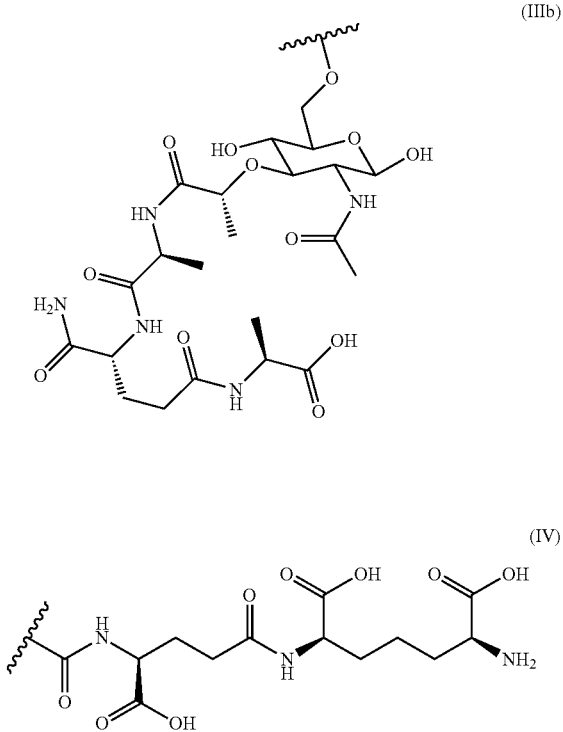

wherein $R^1$, $R^4$ and $R^5$ are each independently selected from H or $C_1$-$C_6$ branched or straight chain alkyl or alkenyl, or $R^4$ and $R^5$ together with the carbon atoms to which they are attached form a 4-, 5-, 6-, 7-, or 8-membered cycloalkyl, cycloalkenyl or aromatic hydrocarbon ring, with up to two carbon atoms in each of $R^1$, $R^4$, $R^5$, and $R^4$ and $R^5$ in combination, each being replaceable with a heteroatom selected from O, N and S; and the wavy line indicates the point of attachment to the rest of the compound. More preferably, the immunostimulant portion has a structure according to any one of Formula (I), Formula (IIa), Formula (Ma), and Formula (IV).

For example, the immunostimulant portion may be 6-O—(N-acetylmuramyl-L-alanyl-D-isoglutamine)-yl, N-acetyl-muramyl-L-alanyl-D-isoglutaminyl, N-acetylmuramyl-*L*-alanyl-D-isoglutaminyl-L-alanyl, or 6-O—(N-acetylmuramyl-L-alanyl-D-isoglutaminyl-L-alanine)-yl.

In particular, the immunostimulant portion may have a structure according to Formula (V):

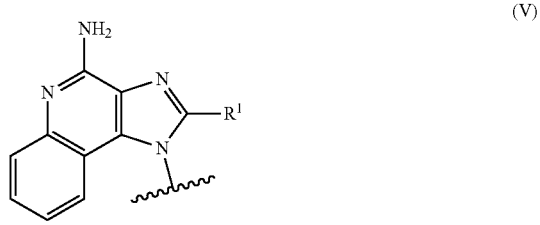

wherein $R^1$ is as defined above.

The immunostimulant portion preferably has a structure according to Formula (VI):

Peptide Portion

The compounds of the invention comprise a peptide portion. As used herein, the term "peptide portion" refers to a portion of the compound which is derivable from a peptide. In particular, the peptide portion may be derived from a peptide by removal of one or more hydrogen atoms and/or the C-terminal hydroxyl group, with the covalent bond(s) to hydrogen and/or the hydroxyl group being replaced by bonds to one or more other portions of the immunostimulatory compound. The peptide portion will therefore comprise at least two amino acid residues.

Preferably, the peptide portion comprises 100 or fewer amino acid residues, or 50 or fewer amino acid residues. For example, the peptide portion may comprise 45 or fewer, 35 or fewer, 25 or fewer, 20 or fewer, 15 or fewer amino acid residues. Alternatively or additionally, the peptide portion may comprise 4 or more, 5 or more, 6 or more, 7 or more, 8 or more, 9 or more, 10 or more, 15 or more, 20 or more, or 30 or more amino acid residues. Any endpoint may be combined with any other endpoint to provide a range of suitable peptide lengths. For example, the peptide portion may comprise between 4 and 45 amino acid residues, or between 10 and 35 amino acid residues.

The amino acids forming the peptide portion may be any suitable amino acids having both an amino group and a carboxylate group. In particular, the amino acids may be naturally-occurring amino acids (including the 22 proteinogenic amino acids, preferably any of the 20 amino acids that are encoded by the universal genetic code) and/or non-natural amino acids. The amino group and the carboxylate group of the amino acids may be separated by a single carbon atom (α-amino acid), by two carbon atoms (β-amino acid), or by three or more carbon atoms. Where the amino acid comprises a stereocentre, the stereocentre may have R or S stereochemistry. In the case of α-amino acids having a chiral a carbon, the amino acid may have D or L stereochemistry.

The amino acid residues forming the peptide portion may have one or more covalent links between the side chains of different amino acid residues, in addition to the covalent linkages of the peptide backbone. The sidechain links may be between the sidechains of amino acid residues which are adjacent in the amino acid sequence, or between those which are more widely separated. Examples of covalent links include disulfide bonds, carbon-heteroatom bonds, and carbon-carbon bonds.

The peptide portion may have an amino acid sequence in which 75% or less, 60% or less, 50% or less, 45% or less, or 40% or less of the amino acid residues have a hydrophobic sidechain. In particular, amino acids having a hydrophobic sidechain may be those in which the sidechain is selected from the group consisting of hydrogen, a hydrocarbon sidechain, a sidechain comprising an aromatic hydrocarbon ring, a thiol sidechain, and a thioether sidechain.

For example, amino acids having a hydrophobic sidechain may be those selected from the group consisting of tryptophan, tyrosine, phenylalanine, leucine, isoleucine, valine, methionine, alanine and glycine (W, Y, F, L, I, V, M, A, G). In a further example, amino acids having a hydrophobic sidechain may be those selected from the group consisting of tryptophan, tyrosine, phenylalanine, leucine, isoleucine, valine, methionine, alanine, proline and glycine. Acetylated lysine is typically also considered to be a hydrophobic amino acid.

The peptide portion may have an amino acid sequence which is non-natural. In particular, the peptide portion may have an amino acid sequence which has a sequence identity of less than 100%, 90% or less, 80% or less, 70% or less, 60% or less, or 50% or less, with any known natural peptide sequence. The non-natural sequence may comprise only naturally-occurring amino acids, or may additionally or alternatively comprise one or more non-natural amino acids.

Preferably, the peptide portion is not derived from a disease-associated antigen. In particular, the peptide portion may have an amino acid sequence which has a sequence identity of less than 100%, 99% or less, 98% or less, 95% or less, 90% or less, 85% or less, 80% or less, 70% or less, 60% or less, or 50% or less, with a known disease-associated antigen. Sequences of known disease-associated antigens are readily available.

Preferably, the peptide portion has an isoelectric point of 5 or greater. In particular, the peptide portion may have an isoelectric point of 5.0 or greater, 5.2 or greater, 5.4 or greater, 5.6 or greater, 5.8 or greater, 6.0 or greater, 6.5 or greater, or 7.0 or greater. The isoelectric point may be 12.6 or less, 8.0 or less, 7.5 or less, 7.0 or less, 6.5 or less, or 6.0 or less. Any lower limit may be combined with any upper limit to define a range of suitable values. Thus, for example, the peptide portion may have an isoelectric point of from 5.0 to 12.6, or from 5.0 to 7.0, or from 5.2 to 5.8.

Preferably, the peptide portion has an absolute net positive charge of 2 or greater, 3 or greater, 4 or greater. Preferably, the peptide portion has a ratio of net positively charged amino acids to total amino acids of from 2:17 to 3:4. Preferably, the peptide portion contain at least one histidine residue.

Preferably the peptide portion has an absolute net positive charge as defined herein and/or a ratio of net positively charged amino acids to total amino acids as defined herein, together with an amino acid sequence in which 75% or less, 60% or less, 50% or less, 45% or less, or 40% or less of the amino acid residues have a hydrophobic sidechain, as defined herein.

Preferably, the peptide portion has low intrinsic immunogenicity. For example, the peptide portion may comprise no known or predicted T cell epitopes, and/or no known or predicted B cell epitopes. Alternatively, any epitope present in the peptide portion may be an epitope that does not induce an immune response, for example because it is an epitope found in a human protein that is tolerated by the human immune system.

Preferably, the peptide portion is not known or adapted for targeting and/or binding to a particular type of cell receptor, or for crossing a cell membrane.

The peptide portion may be used to modify the physicochemical properties of the compound. The possibility for including amino acid residues having sidechains which are generally hydrophobic or hydrophilic allows the creation of a peptide portion or a compound having a required solubility in different solvents. Furthermore, since the amino acid residues can have sidechains which are acidic or basic, and with different pKa values, the solubility can be manipulated by varying the pH and/or ionic concentration of the solution. The modular nature of peptides, together with standardised techniques for peptide synthesis which are able to incorporate a wide range of amino acids, makes peptide portions readily suitable for this purpose.

It will be understood that the physicochemical properties of the peptide portion relate not only to interaction of a single compound with the surrounding solvent, but also to interaction of a peptide portion with itself (e.g. folding of the peptide), and with peptide portions of other nearby instances of the compound (e.g. agglomeration). Thus, the peptide portion may have an amino acid sequence which favours a particular secondary structure under certain conditions. Alternatively or additionally, the peptide may interact with other components present in a pharmaceutical composition. For example, the peptide portion may associate with an aluminium-based adjuvant, such as aluminium hydroxide or aluminium phosphate. Such interaction may be triggered by a charge present on the peptide portion. Any such interactions may cause the peptide to agglomerate.

In this way, the peptide can be selected to provide the compound with desirable properties under different conditions. For example, it may be desirable that the compound is soluble in a first solution, such as water for injection, histidine buffer solution (for example, 28 mM L-histidine buffer), sodium bicarbonate, Tris-HCl, a phosphate buffer or an acetic acid buffer, in order to allow the compound to be formulated in a pharmaceutical composition. It may then be desirable that the compound has a lower solubility and/or agglomerates in a second solution, such as a serum, plasma, interstitial fluid or cell culture medium (or a solution that is representative of such a physiological solution, for example: an aqueous sodium chloride solution such as 0.9% sodium chloride solution; an aqueous solution of sodium chloride and histidine such as 9.% sodium chloride in 28 mM L-histidine; or phosphate buffer solution, PBS). In particular, a soluble compound may freely diffuse throughout the solution, independently of other molecules of the compound, whereas an insoluble compound has restricted freedom to diffuse. Reduced solubility in a physiological fluid, particularly an extracellular fluid, may restrict the compound from being easily transported around a human or animal body following administration. In this way, the prevalence of unwanted side effects may be reduced.

Exemplary peptide portions include those comprising any sequence having amino acid residues selected from those listed in Table 1 and Table 2:

TABLE 1

| | Position | | | | | | | | | | | | | | | | |
|---|---|---|---|---|---|---|---|---|---|---|---|---|---|---|---|---|---|
| | P1 | P2 | P3 | P4 | P5 | P6 | P7 | P8 | P9 | P10 | P11 | P12 | P13 | P14 | P15 | P16 | P17 |
| Amino acid residues | K R H | K R H | L H Q | L H Q | K R H | K R H | L H Q | L H Q | K R H | L H Q | L H Q | K R H | K R H | L H Q | L H Q | K R H | K R H |

TABLE 1-continued

| | Position | | | | | | | | | | | | | | | | |
|---|---|---|---|---|---|---|---|---|---|---|---|---|---|---|---|---|---|
| | P1 | P2 | P3 | P4 | P5 | P6 | P7 | P8 | P9 | P10 | P11 | P12 | P13 | P14 | P15 | P16 | P17 |
| | Q | Q | A | A | Q | Q | A | A | Q | A | A | Q | Q | A | A | Q | Q |
| | A | A | | | A | A | W | W | A | W | W | A | A | | | A | A |
| | | | | | L | L | | | L | | | L | L | | | | |

TABLE 2

| | Position | | | | | | | | | | | | | | | | |
|---|---|---|---|---|---|---|---|---|---|---|---|---|---|---|---|---|---|
| | P1 | P2 | P3 | P4 | P5 | P6 | P7 | P8 | P9 | P10 | P11 | P12 | P13 | P14 | P15 | P16 | P17 |
| Amino acid residues | R | R | L | L | H | A | H | L | A | L | H | A | H | L | L | R | R |
| | K | K | | | K | | K | | K | | K | | K | | | K | K |
| | H | H | | | R | | R | | R | | R | | R | | | H | H |
| | L | | | | L | | L | | H | | L | | L | | | | L |
| | | | | | A | | A | | | | A | | A | | | | |
| | | | | | P | | P | | | | P | | P | | | | |

Thus, the peptide portion may have (i.e, comprise) a sequence in which position 1 is selected from the amino acid residues (K, R, H, Q, A); position 2 is selected from the amino acid residues (K, R, H, Q, A); position 3 is selected from the amino acid residues (L, H, Q, A); position 4 is selected from the amino acid residues (L, H, Q, A); position 5 is selected from the amino acid residues (K, R, H, Q, A, L); position 6 is selected from the amino acid residues (K, R, H, Q, A, L); position 7 is selected from the amino acid residues (L, H, Q, A, W); position 8 is selected from the amino acid residues (L, H, Q, A, W); position 9 is selected from the amino acid residues (K, R, H, Q, A, L); position 10 is selected from the amino acid residues (L, H, Q, A, W); position 11 is selected from the amino acid residues (L, H, Q, A, W); position 12 is selected from the amino acid residues (K, R, H, Q, A, L); position 13 is selected from the amino acid residues (K, R, H, Q, A, L); position 14 is selected from the amino acid residues (L, H, Q, A); position 15 is selected from the amino acid residues (L, H, Q, A); position 16 is selected from the amino acid residues (K, R, H, Q, A); and position 17 is selected from the amino acid residues (K, R, H, Q, A).

Further, the peptide portion may comprise a sequence in which position 1 is selected from the amino acid residues (R, K, H, L); position 2 is selected from the amino acid residues (R, K, H); position 3 is the amino acid residue (L); position 4 is the amino acid residue (L); position 5 is selected from the amino acid residues (H, K, R, L, A, P); position 6 is the amino acid residue (A); position 7 is selected from the amino acid residues (H, K, R, L, A, P); position 8 is the amino acid residue (L); position 9 is selected from the amino acid residues (A, K, R, H); position 10 is the amino acid residue (L); position 11 is selected from the amino acid residues (H, K, R, L, A, P); position 12 is the amino acid residue (A); position 13 is selected from the amino acid residues (H, K, R, L, A, P); position 14 is the amino acid residue (L); position 15 is the amino acid residue (L); position 16 is selected from the amino acid residues (R, K, H); and position 17 is selected from the amino acid residues (R, K, H, L).

Specifically, the peptide portion may comprise one of the following sequences:

| | |
|---|---|
| SEQ ID No 32 | RRLLHAHLALHAHLLRR |
| SEQ ID No 1 | RRLLAHLLHLLHALLRR |
| SEQ ID No 2 | RRLLAHLLALLHALLRR |
| SEQ ID No 3 | RALLAHLLALLHALLAR |
| SEQ ID No 4 | RALLAHLLHLLHALLAR |
| SEQ ID No 5 | RRLLRHLLHLLHRLLRR |
| SEQ ID No 6 | RRLLRHLLALLHRLLRR |
| SEQ ID No 7 | RHLLAHLLALLHALLHR |
| SEQ ID No 8 | RHLLAHLLHLLHALLHR |
| SEQ ID No 9 | AHLLAHLLHLLHALLHA |
| SEQ ID No 10 | AHLLAHLLALLHALLHA |
| SEQ ID No 11 | AHLLAHLLRLLHALLHA |
| SEQ ID No 12 | RRLLRRLLRLLRRLLRR |
| SEQ ID No 13 | KKLLKKLLKLLKKLLKK |
| SEQ ID No 14 | RRLLRRLLALLRRLLRR |
| SEQ ID No 15 | RRLLARLLALLRALLRR |
| SEQ ID No 16 | RRLLRALLALLARLLRR |
| SEQ ID No 17 | RRLLHALLALLAHLLRR |
| SEQ ID No 18 | RRLLPAPLALPAPLLRR |
| SEQ ID No 19 | RRLLPAALALAAPLLRR |
| SEQ ID No 20 | RRLLPALLALLAPLLRR |
| SEQ ID No 21 | RRLLLAPLALPALLLRR |
| SEQ ID No 22 | RRLLAAPLALPAALLRR |
| SEQ ID No 23 | LRLLHALLALLAHLLRL |
| SEQ ID No 24 | LRLLHAPLALPAHLLRL |
| SEQ ID No 25 | LRLLHAALALAAHLLRL |

-continued

| SEQ ID No 26 | LRLLPAHLALHAPLLRL |
| --- | --- |
| SEQ ID No 27 | LRLLAAHLALHAALLRL |
| SEQ ID No 28 | RRLLHAPLALPAHLLRR |
| SEQ ID No 29 | RRLLHAALALAAHLLRR |
| SEQ ID No 30 | RRLLPAHLALHAPLLRR |
| SEQ ID No 31 | RRLLAAHLALHAALLRR |
| SEQ ID No 33 | RRLLHAKLALKAHLLRR |
| SEQ ID No 34 | RRLLKAKLALKAKLLRR |
| SEQ ID No 35 | RRLKKAKLKLKAKKLRR |

Alternatively, the peptide portion may comprise a truncated sequence selected from any one of the above peptide sequences. For example, the peptide portion may comprise a truncated sequence of 9 or more, 10 or more, 11 or more, 12 or more, 13 or more, 14 or more, 15 or more, or 16 contiguous amino acids from any one of the above sequences. In particular, the truncated sequence may comprise 9 contiguous amino acids from positions P5 to P13 in any one of the above sequences.

The peptide portion may comprise a sequence having a sequence identity of 75% or more, 80% or more, 85% or more, 90% or more, or 95% or more with at least one of the above sequences. For example, the peptide portion may comprise a sequence having at least 80% identity with 9 contiguous amino acids from positions P5 to P13 of any one of SEQ ID No 1 to SEQ ID No 35.

Further, one or more leucine amino acids (L) in the peptide portion can be replaced by aliphatic, aromatic or thioether amino acids with similar physicochemical properties. Examples of such aliphatic, aromatic or thioether amino acids are isoleucine (I), valine (V), tryptophan (W), tyrosine (Y), phenylalanine (F) and methionine (M). For example, leucine amino acids can be replaced by isoleucine amino acids (I) and by valine amino acids (V). For example, in the exemplary peptide portions of Table 1 and Table 2 any L can be replaced by any of I, V, W, Y, F and M (e.g., any L can be replaced by I or by V).

Still further, particularly preferred peptide portions may have an amino acid sequence in which a dibasic sequence of formula RR, RK, KR, KK, HR, RH, HK, KH or HH is/are present at one or both of the N-terminus and the C-terminus of the sequence (wherein the dibasic sequence(s) is(are) more preferably selected from RR, RK, KR, KK and is(are) more preferably still RR). For example, in the exemplary peptide portions of Table 1 and Table 2 particularly preferred peptide portions may have such a dibasic sequence at positions 1 and 2, or at positions 16 and 17, or at all of positions 1, 2, 16 and 17. The presence of such dibasic sequences may advantageously contribute to the solubility of the peptide during formulation.

Especially preferred peptide portions of Table 1 and Table 2 have an amino acid sequence in which 75% or less of the amino acid residues have a hydrophobic sidechain (e.g., wherein amino acid residues having a hydrophobic sidechain are selected from the group consisting of tryptophan, tyrosine, phenylalanine, leucine, isoleucine, valine, methionine, alanine and glycine).

The peptide portion may comprise further amino acid residues at the N-terminus or C-terminus of the sequence. In particular, such additional amino acids may be incorporated to aid in manufacturing or purification of the peptide portion. Examples of additional amino acid sequences which can be used for such purposes are known in the art.

In one aspect, the invention relates to the use of a peptide to reduce the solubility of an immunostimulant in extracellular fluid, wherein the peptide is covalently linked to the immunostimulant. For the avoidance of doubt, the peptide and immunostimulant will then form the peptide portion and immunostimulant portion respectively of a compound, as described above. The extracellular fluid may be blood, serum or interstitial fluid. The reduction in the solubility of the immunostimulant in extracellular fluid may, for example, comprise reduced in vivo diffusion/body distribution, and/or local administration site entrapment, and/or reduced systemic activation of pro-inflammatory cytokine response through the formation of higher molecular weight structures or supramolecular structure, and/or physical contact with molecules or cells at the injection site, and/or entrapment/uptake by immunocompetent cells or lymphoid organs. The reduction in the solubility of the immunostimulant in extracellular fluid may also comprise reduced solubility (e.g., formation of higher molecular weight structures or supramolecular structure) in an extracellular fluid under in vitro conditions. By "reduce the solubility" is meant reduce compared to the solubility of the immunostimulant per se (i.e., when not covalently linked to the peptide).

In another aspect, the invention relates to the use of a peptide to increase the vaccine adjuvanticity of an immunostimulant in extracellular fluid, wherein the peptide is covalently linked to the immunostimulant compared with the immunostimulant per se (i.e., when not covalently linked to the peptide In these aspects relating to use of a peptide, preferably the use is a use of a peptide to reduce the solubility and to increase the adjuvanticity of an immunostimulant in extracellular fluid, wherein the peptide is covalently linked to the immunostimulant.

Coupling the peptide to the immunostimulant may, for example, reduce the pyrogenicity of the immunostimulant compared to the 'free' immunostimulant, and/or reduce the levels of in vivo inflammatory indicators, such as IL-1, TNF-α, IL-6 and/or IL-8 in the circulation. In another aspect of the invention, the peptide is used to improve the immunostimulatory effect of the immunostimulant on a specific immune response, compared to the effect of the 'free' immunostimulant. For example, the immunostimulant-peptide compound may promote a better in vivo cell-mediated immune response and/or humoral response to a co-administered antigen than the 'free' immunostimulant.

For the avoidance of doubt, where the peptide portion (a) is not a disease-associated immunogen; (b) has an amino acid sequence in which 75% or less of the amino acid residues are hydrophobic; and/or (c) has an isoelectric point of 5 or greater, the peptide portion necessarily has feature (a) and has at least one of features (b) and (c). Preferably the said peptide portion both has an amino acid sequence in which 75% or less of the amino acid residues are hydrophobic and has an isoelectric point of 5 or greater.

Vector Portion

The compounds of the invention may comprise a vector portion. As used herein, the term vector portion refers to a portion of the compound which is adapted for association with a non-aqueous environment. Preferably, the vector may comprise one or more moieties selected from a hydrocarbon, a fluorocarbon, and a lipid.

A hydrocarbon moiety may be any radical consisting of hydrogen and carbon, but will typically comprise a carbon chain, such as a chain of from 3 to 30 carbon atoms, from 5 to 25 carbon atoms, or from 8 to 20 carbon atoms. The carbon chain may be linear or branched, but is preferably linear, and may be saturated or unsaturated, but is preferably saturated.

In some embodiments, the hydrocarbon moiety can have the chemical structure:

$C_yH_x-$ or derivatives thereof, where y=3 to 30, and x≤2y+1. Typically x and y satisfy the relationship 2y−1≤x≤2y+1, and preferably x=2y+1. Preferably the $C_yH_x$ moiety is linear.

It is preferred that y is from 5 to 25, more preferably from 8 to 20. It is preferred that the $C_yH_x$ moiety is saturated (i.e., x=2y+1) and linear, and that y=8 to 18 or 8 to 16.

A vector comprising a hydrocarbon moiety may be particularly suitable for interaction with a hydrophobic environment, such as a hydrocarbon-rich environment. In the context of the current invention, the hydrocarbon moiety may be modified such that the vector is still capable of association with a non-aqueous environment. For example, the hydrocarbon moiety may comprise one or more heteroatoms without removing the ability of the hydrocarbon moiety to associate with a non-aqueous environment. Typically, however, the hydrocarbon moiety will consist of the elements carbon and hydrogen.

The fluorocarbon moiety may be any hydrocarbon moiety as defined above, in which one or more hydrogen atoms has been replaced with fluorine. In particular, the fluorocarbon moiety may be perfluorinated, or partially fluorinated. Thus, the fluorocarbon moiety will typically comprise a carbon chain, such as a chain of from 3 to 30 carbon atoms, from 5 to 25 carbon atoms, or from 8 to 20 carbon atoms. The carbon chain may be linear or branched, but is preferably linear, and may be saturated or unsaturated, but is preferably saturated.

In some embodiments, the fluorocarbon moiety can have the chemical structure:

$C_mF_n-C_yH_x-$ or derivatives thereof, where m=3 to 30, n≤2m+1, y=0 to 15, x≤2y, and (m+y)=3 to 30. Typically m and n satisfy the relationship 2m−1≤n≤2m+1, and preferably n=2m+1. Typically x and y satisfy the relationship 2y−2≤x≤2y, and preferably x=2y. Preferably the $C_mF_n-C_yH_x$ moiety is linear.

It is preferred that m is from 5 to 15, more preferably from 8 to 12. It is also preferred that y is from 0 to 8, more preferably from 0 to 6 or 0 to 4. It is preferred that the $C_mF_n-C_yH_x$ moiety is saturated (i.e., n=2m+1 and x=2y) and linear, and that m=8 to 12 and y=0 to 6 or 0 to 4.

In a particular example, the fluorocarbon moiety is derived from 2H, 2H, 3H, 3H-perfluoroundecanoic acid of the following formula:

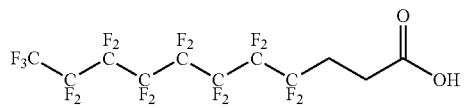

Thus, a preferred fluorocarbon moiety is the linear saturated moiety $C_8F_{17}(CH_2)_2-$.

Further examples of fluorocarbon moieties have the following formulae: $C_6F_{13}(CH_2)_2-$, $C_7F_{15}(CH_2)_2-$, $C_9F_{19}(CH_2)_2-$, $C_{10}F_{21}(CH_2)_2-$, $C_5F_{11}(CH_2)_3-$, $C_6F_{13}(CH_2)_3-$, $C_7F_{15}(CH_2)_3-$, $C_8F_{17}(CH_2)_3-$ and $C_9F_{19}(CH_2)_3-$ which are derived from $C_6F_{13}(CH_2)_2COOH$, $C_7F_{15}(CH_2)_2COOH$, $C_9F_{19}(CH_2)_2COOH$, $C_{10}F_{21}(CH_2)_2COOH$, $C_5F_{11}(CH_2)_3COOH$, $C_6F_{13}(CH_2)_3COOH$, $C_7F_{15}(CH_2)_3COOH$, $C_8F_{17}(CH_2)_3COOH$ and $C_9F_{19}(CH_2)_3COOH$ respectively.

Preferred examples of suitable structures for the fluorocarbon vector portion have the formula:

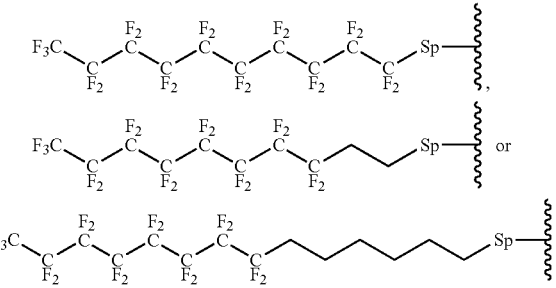

in which Sp is a spacer as defined herein and the wavy line indicates the point of attachment to the remainder of the molecule. Preferably Sp is derived from a lysine residue and has the formula $-CONH-(CH_2)_4-CH(NH_2)-CO-$. The amino group of the N-terminal amino acid of a peptide, such as the peptide portion of the compound of the invention, or of a peptide antigen, may thus form an amide linkage with the C-terminal carboxy group of the spacer of formula $-CONH-(CH_2)_4-CH(NH_2)-CO-$.

A vector comprising a fluorocarbon moiety may be particularly suitable for interaction with a fluorinated environment, such as a fluorocarbon-rich environment. Compounds having vector portions comprising fluorocarbon moieties may therefore self-associate to form multimolecular fluorocarbon-based micelles in both polar (protic and aprotic) and non-polar solvents.

Fluorocarbon-based vectors are known to be useful in improving delivery of antigens. Examples of fluorocarbon-linked peptides are given in WO2005/099752 and WO2009/027688 and the advantages afforded by the fluorocarbon attachment in the enhancement of immune responses to the peptide are provided therein. In order to improve the solubility of such fluorocarbon-linked peptides, WO 2012/090002 (incorporated in its entirety herein by reference) describes a process for treating the fluorocarbon-linked peptides to promote formation of multimolecular fluorocarbon-based micelle-like structures. The use of a fluorocarbon vector portion in the compound of the present invention therefore allows the compound to be incorporated into such micelles.

In the context of the current invention, the fluorocarbon vector portion may be modified such that the vector is still capable of association with a fluorinated environment. For example, the fluorocarbon moiety may comprise one or more heteroatoms without removing the ability of the fluorocarbon to associate with a non-aqueous environment. Similarly, one or more of the fluorine atoms may be replaced with other halogen atoms such as chlorine, bromine or iodine, without removing the ability of the fluorocarbon to associate with a fluorinated environment. Typically, however, the fluorocarbon moiety will consist of the elements carbon, fluorine, and optionally hydrogen.

The lipid moiety may be any suitable radical derivable from a lipid by removal of a hydrogen atom. The lipid may be any suitable lipid, and may be naturally-occurring or non-natural. Suitable lipids include fats, waxes, sterols, fat-soluble vitamins, monoglycerides, diglycerides, triglycerides and phospholipids. Suitable lipids may be categorised as fatty acids, glycerolipids, glycerophospholipids, sphingolipids, saccharolipids, polyketides, sterol lipids and prenol lipids. Sterol lipids are preferred. In particular, the lipid moiety may be derivable from cholesterol.

A vector comprising a lipid moiety may be particularly suitable for interacting with a lipid environment.

Compound Structure

The compound of the invention comprises an immunostimulant portion and a peptide portion, and may further comprise a vector portion. The immunostimulant portion may be linked to the peptide portion at any position in the amino acid sequence of the peptide portion, but is preferably each linked to an amino acid residue which is no more than 5 positions, no more than 4 positions, no more than 3 positions, or no more than 2 position from one end of the sequence, or is a terminal amino acid residue.

In particular, the compound may consist essentially of, or consist of, an immunostimulant portion, a peptide portion and a vector portion.

Where the vector portion is present, it is preferred that the immunostimulant portion and the vector portions are independently linked to amino acid residues which are separated in the amino acid sequence by at least 50%, at least 60%, at least 70%, at least 80%, at least 90%, or at least 95% of the sequence length. Particularly preferably, the immunostimulant portion and the vector portion are each linked to different terminal amino acid residues of the peptide portion sequence. Thus, for example, the immunostimulant portion may be linked to the C-terminal amino acid residue, and/or the vector portion may be linked to the N-terminal amino acid residue.

The immunostimulant portion, and vector portion where present, may be linked directly to the peptide portion by a single covalent bond, or may be linked by covalent bonds via one or more intermediate atoms. The immunostimulant portion may be linked to the peptide portion by a spacer portion. Preferably, the spacer portion is hydrophilic. For example, the spacer portion may comprise one or more or of β-alanine, aminobutyric acid, aminovaleric acid, and aminocaproic acid.

Alternatively or additionally, the spacer portion may comprise a polymeric moiety of at least three monomer units, such as a polyethylene glycol moiety. For example, the spacer portion may comprise a polyethylene glycol moiety having 3 or more, 4 or more, 5 or more, 6 or more, 7 or more, 8 or more, or 9 or more monomer units. The polyethylene glycol moiety may have 15 or fewer, 14 or fewer, 13 or fewer, 12 or fewer, 11 or fewer, 10 or fewer, 9 or fewer, or 8 or fewer monomer units. Any endpoint may be combined with any other endpoint to define a range of suitable polymer lengths. For example, the polyethylene glycol moiety may have from 5 to 15 monomer units.

The inclusion of a spacer portion may provide the immunostimulant portion with a degree of freedom relative to the peptide portion. Thus, where the peptide portion is insoluble in a particular environment, a spacer portion may allow the immunostimulant portion to be solvated and capable of presentation to a receptor on a suitable cell.

Preferably, the spacer portion comprises a cleavable linker. The linker may be, for example, an acid-cleavable linker or an enzymatically-cleavable linker. Exemplary acid-cleavable linkers include an imine, a hydrazone, a ketal or acetal, an acyl hydrazone, a cis-aconity, and a trityl. Exemplary enzymatically-cleavable linkers include the peptide sequence ALALX (cleavable by cathepsin B), a β-D-glucuronic ester (cleavable by β-glucuronidase), an azobenzene, such as an azobenzene-2-carboxylate (cleavable by azoreductase), an ester (cleavable by esterase), a phosphate ester (cleavable by acid phosphatase), and γ-glutamyl amide (cleavable by γ-glutamyl transpeptidase).

The compound may be prepared using standard synthetic chemistry routes. For example, the peptide portion may be prepared using solid phase peptide synthesis (SPPS) on suitable resin bead supports. Once synthesis of the peptide portion is complete, whilst the peptide portion is still attached to the support, a second portion of the compound may be attached at or near the free end of the peptide portion, either via the end of the peptide chain, or via a sidechain of an amino acid residue. A third portion of the compound may be attached at or near the bound end of the peptide portion, either via the sidechain of an amino acid residue, or with concomitant cleavage of the peptide portion from the resin. Alternatively, the peptide portion may be cleaved from the resin following attachment of the second portion, and attachment of the third portion carried out in solution.

Preferably, the peptide portion is grown from the C-terminus to the N-terminus on a suitable resin support, followed by coupling of a vector portion to the deprotected N-terminus. The previously prepared immunostimulant, optionally with attached spacer, is then coupled to the sidechain of the C-terminal amino acid residue. Finally, the peptide is cleaved from the resin support.

The immunostimulant portion and, where present, other portions of the compound, may be coupled to the peptide portion using any suitable chemical reaction resulting in the formation of a covalent bond. Preferably, the portions are coupled using the reaction of a nucleophile with a carboxyl group. For example, an amine on one portion may react with a carboxylate on a second portion to form an amide.

The compound may have a molecular weight which is at least 1000 Da, preferably at least 1700 Da, more preferably at least 2100 Da, such as at least 2500 Da. The compound may have a molecular weight of 10000 Da or less, preferably 8000 Da or less, more preferably 6500 Da or less, such as 5000 Da or less. Any endpoint may be combined with any other endpoint to define a range of suitable molecular weights. For example, the compound may have a molecular weight of from 1700 to 8000 Da, or from 2100 Da to 6500 Da.

Pharmaceutical Composition

The compound of the invention may be formulated as a pharmaceutical composition, in combination with a pharmaceutically acceptable carrier or diluent.

Alternatively, the compound of the invention may be formulated as a pharmaceutical composition with an immunogen, optionally in combination with a pharmaceutically acceptable carrier or diluent.

The compound may be soluble in the environment of the pharmaceutical composition. In some embodiments, therefore, following administration of the pharmaceutical composition, the solubility of the compound in the administration environment is reduced, thereby reducing the ability of the human or animal body to transport the compound away from the site of administration.

The diluent may comprise a stabilizer or bulking agent necessary for efficient lyophilisation. Examples include sorbitol, mannitol, polyvinylpyrrolidone, and mixtures thereof, preferably mannitol. Other excipients that may be present include preservatives such as antioxidants, lubricants, cryopreservatives and binders well known in the art.

The pharmaceutical composition may comprise more than one immunostimulatory compound, such as more than one compound of the invention. Different immunostimulatory compounds may have different immunostimulatory activity, and may for example act as agonists against different receptors. The compounds may act as agonists against two or more receptors selected from TLR, TLE and NOD. For example, the pharmaceutical composition may comprise a first compound comprising an immunostimulant portion which is an agonist for TLR7 and a second compound comprising an immunostimulant portion which is an agonist for TLR8 and/or NOD2. In this way, the immunogenicity of the composition may be improved, and/or the immunogenic response polarised towards certain cell types, such as for example Th1 and/or Th17.

The pharmaceutical composition may further comprise one or more adjuvants. An adjuvant is an agent that is able to modulate the immune response directed to a co-administered antigen while having few if any direct effects when given on its own. Such adjuvants may be capable of potentiating the immune response in terms of magnitude and/or cytokine profile. Examples of adjuvants include: natural or synthetically derived refinements of natural components of bacteria such as Freund's adjuvant & its derivatives, muramyldipeptide (MDP) derivatives, CpG, monophosphoryl lipid A; other known adjuvant or potentiating agents such as saponins, aluminium salts and cytokines; oil in water adjuvants, water-in-oil adjuvants, immunostimulating complex (ISCOMs), liposomes, formulated nano and micro-particles; bacterial toxins and toxoids; inulin, particularly gamma inulin; and TLR agonists.

Preferably, the adjuvant may be selected from the group consisting of: Peptidoglycan (such as TDM, MDP, muramyl dipeptide, Murabutide); alum solution (such as aluminium hydroxide, ADJUMER™ (polyphosphazene) or aluminium phosphate gel); glucans; algammulin; surfactants (such as squalane, Tween 80, Pluronic or squalene); calcium phosphate gel; bacterial toxins or toxoids (such as cholera holotoxin, cholera-toxin-A1-protein-A-D-fragment fusion protein, sub-unit B of the cholera toxin, or block copolymers); cytokine-containing liposomes; water-in-oil adjuvants (such as Freund's complete adjuvant, Freund's incomplete adjuvant or Montanide such as ISA 51 or ISA 720); oil-in-water adjuvants (such as MF-59); inulin-based adjuvants; cytokines (such as interferon-gamma; interleukin-1beta; interleukin-2; interleukin-7 or interleukin-12); ISCOMs (such as iscomatrix); microspheres and microparticles of any composition; and Toll-like receptor agonists (such as CpG, ligands of human TLR 1-10, ligands of murine TLR 1-13, ISS-1018, IC31, Imidazoquinolines, Poly (I:C), Monophosphoryl lipid A, Ribi529, cholera toxin, heat-labile toxin, Pam3Cys or Flagellin).

The pharmaceutical composition may comprise a discrete phase suspended in a continuous phase. Alternatively, the composition may comprise a solid or liquid which, when prepared for administration, comprises a discrete phase suspended in a continuous phase. For example, the pharmaceutical composition may comprise an emulsion, such as a water-in-oil emulsion or an oil-in-water emulsion. Alternatively or additionally, the pharmaceutical composition may comprise micelles or liposomes.

In particular, the continuous phase may be aqueous, and the discrete phase may be non-aqueous. In such cases, the compound may be localised to the discrete phase, and therefore not able to freely diffuse through the continuous phase independently of the discrete phase. For example, at least part of the compound may be adhered to the surface of, or embedded in, the discrete phase. This arrangement may be stabilised by solvation of that part of the compound by constituents of the discrete phase. At the same time, a further part of the compound may be exposed to, or located in, the continuous phase. In particular, the immunostimulant portion may be located in the continuous phase, such that the immunostimulant portion is generally surrounded by the continuous phase.

In particular, where the compound comprises a vector portion, the vector portion may be adhered to the surface of, or embedded in, the discrete phase. For example, where the vector portion comprises a hydrocarbon moiety, the discrete phase may comprise a hydrophobic phase, such that the vector portion is at least partially embedded in the hydrophobic phase. Where the vector portion comprises a fluorocarbon moiety, the discrete phase may comprise a fluorinated phase, such that the vector portion is at least partially embedded in the fluorocarbon phase. Where the vector portion comprises a lipid moiety, the discrete phase may comprise a lipid phase, such that the vector portion is at least partially embedded in the lipid phase. In each case, the immunostimulant portion and peptide portion of the compound may be exposed to the continuous phase, which may be an aqueous continuous phase.

Medical Uses

The invention provides the compound and composition of the invention for use in medical treatments.

Thus, the invention provides a method of stimulating an immune response to an immunogen, comprising administering the compound or pharmaceutical composition of the invention, to a human or animal. The method may comprise administering an immunogen concurrently or consecutively with the compound or pharmaceutical composition. For example, the pharmaceutical composition may comprise the immunogen as well as the compound of the invention. Preferably, the immunogen and the compound or pharmaceutical composition are administered to the same site on the human or animal body.

Alternatively, the method may comprise administering the compound or pharmaceutical composition without an immunogen. The compound of the invention may be useful in non-specific anti-viral, anti-tumour and/or anti-inflammatory therapies.

Thus the present invention also provides a product containing a compound of the invention and an immunogen for simultaneous, separate or sequential use in the treatment of a disease.

The method may also comprise administering a further immunostimulatory compound concurrently or consecutively with the compound or pharmaceutical composition. The further immunostimulatory compound may be a second compound of the invention. The compounds may have different immunostimulatory activity, as set out above. For example, the pharmaceutical composition may comprise two immunostimulatory compounds, such as two compounds of the invention. The compounds may differ in one or more features, and particularly in the nature of the immunostimulant portions. Preferably the further immunostimulatory compound, and the compound or pharmaceutical composition are administered to the same site on the human or animal body.

Thus the present invention also provides a product containing a compound of the invention and a further immunostimulatory compound for simultaneous, separate or sequential use in the treatment of a disease.

As used herein, the term 'stimulating an immune response' may refer to initiating an immune response to an immunogen in an individual, where such an immune response did not previously exist. Alternatively or additionally, the term may refer to provoking an existing immune response. In either case, it is expected that the ability of the immune system to react to the immunogen is strengthened, so that subsequent immune responses to the immunogen (even if not related to administration of the compound of the invention) will be more effective. The immune response may be effective in the treatment or prevention of a disease.

The disease is typically an infectious disease, an autoimmune disease, an allergy, a hormonal disease or cancer. Where the compound or pharmaceutical composition is administered with an immunogen, the immunogen is selected to include one or more epitopes from the pathogen causing the infectious disease, the autologous protein implicated in the autoimmune disease or hormonal disease, the allergen responsible for the allergy or a tumour antigen expressed on the cancer cells.

Examples of infectious diseases that may be treated or prevented using a compound or composition of the invention include, but are not restricted to, infections caused by the following viruses, bacteria, mycobacteria, parasites and fungi: influenza, Human Immunodeficiency Virus (HIV), Hepatitis C Virus (HCV), Hepatitis B Virus (HBV), Hepatitis A Virus (HAV), Respiratory Syncytial Virus (RSV), Venezuelan Equine Encephalitis virus (VEE), Japanese Encephalitis virus (JEV), Cytomegalovirus (CMV), Epstein Barr Virus (EBV), Herpes Virus (HSV-1 or HSV-2), Ebola, Marburg, Dengue, West Nile and Yellow fever viruses, Porcine reproductive and respiratory syndrome (PRRSV), Feline Immunodeficiency Virus (FIV), *Mycobacterium tuberculosis, Legionella*, Rickettsiae, Chlamydiae, and *Listeria monocytogenes, Plasmodium falciparum* and other species of the Plasmodial family, *Candida albicans, Cryptococcus, Clostridium tetani, Rhodotorula* and *Pneumocystis*.

Examples of cancers that may be treated or prevented using a compound or composition of the invention include breast cancer, melanoma, colorectal cancer nasopharyngeal carcinoma, Burkitt's lymphoma and other human cancers.

The compound or composition of the invention may be used to treat or vaccinate against influenza. The influenza vaccine formulation may be administered in combination with an anti-viral therapeutic composition, including neuraminidase inhibitor treatments such as amanidine, rimantidine, zanamivir or oseltamivir. The influenza vaccine formulation may be administered in combination with other influenza vaccines, such as conventional antibody generating influenza vaccines. The other influenza vaccine is preferably a seasonal influenza vaccine.

Administration may be contemporaneous or separated by time. The compound or composition of the invention may be administered before, together with or after the anti-viral therapeutic composition and/or other influenza vaccine.

The method may have therapeutic or prophylactic application, as defined above.

The appropriate dosage of the prophylactic or therapeutic composition to be administered to a patient will be determined in the clinic. However, as a guide, a suitable human dose, which may be dependent upon the preferred route of administration, may be from 1 to 1000 µg, such as about 100 µg, 200 µg or 500 µg. Multiple doses may be required to achieve an immunological or clinical effect, which, if required, will be typically administered between 2 to 12 weeks apart. Where boosting of the immune response over longer periods is required, repeat doses 1 month to 5 years apart may be applied.

Where a second therapeutic agent or prophylactic agent is used in conjunction with a compound or composition of the invention, administration may be contemporaneous or separated by time. The composition of the invention may be administered before, together with or after the second therapeutic agent. Thus, the invention also provides a product containing a compound of the invention and an immunogen for simultaneous, separate or sequential use in the treatment of cancer, a pathogenic infection, or an autoimmune disease.

Compositions of the invention can be administered to a human or animal subject in vivo using a variety of known routes and techniques. For example, the composition may be provided as an injectable solution, suspension or emulsion and administered via parenteral, subcutaneous, oral, epidermal, intradermal, intramuscular, interarterial, intraperitoneal, intravenous injection using a conventional needle and syringe, or using a liquid jet injection system. The composition may be administered topically to skin or mucosal tissue, such as nasally, intratrachealy, intestinally, sublingually, rectally or vaginally, or provided as a finely divided spray suitable for respiratory or pulmonary administration. Preferably, the compositions are administered intramuscularly.

The composition can be administered to a subject in an amount that is compatible with the dosage composition and that will be prophylactically and/or therapeutically effective. The administration of the composition of the invention may be for either "prophylactic" or "therapeutic" purpose. As used herein, the term "therapeutic" or "treatment" includes any one or more of the following: the prevention of infection or reinfection; the reduction or elimination of symptoms; and the reduction or complete elimination of a pathogen. Treatment may be effected prophylactically (prior to infection) or therapeutically (following infection).

The choice of carrier, if required, is frequently a function of the route of delivery of the composition. Within this invention, compositions may be formulated for any suitable route and means of administration. Pharmaceutically acceptable carriers or diluents include those used in compositions suitable for oral, ocular, rectal, nasal, topical (including buccal and sublingual), vaginal or parenteral (including subcutaneous, intramuscular, intravenous, intradermal, transdermal) administration.

The composition may be administered in any suitable form, for example as a liquid, solid or aerosol. For example, oral formulations may take the form of emulsions, syrups or solutions or tablets or capsules, which may be enterically coated to protect the active component from degradation in the stomach. Nasal formulations may be sprays or solutions. Transdermal formulations can be adapted for their particular delivery system and may comprise patches. Formulations for injection may be solutions or suspensions in distilled water or another pharmaceutically acceptable solvent or suspending agent.

Immunogen

An immunogen is an antigen or allergen capable of inducing an immune response in an animal, such as humans, either when administered alone, or when administered in combination with a suitable adjuvant and/or immunostimulant. Thus, administration of the pharmaceutical composition to a human or animal provides the human or animal body with both an immunogen and an immunostimulant, which may stimulate the immune response of the human or animal body to that immunogen.

The immunogen is typically associated with a particular disease state, such as a pathogenic disease, or a neoplasm. Thus, administration of the pharmaceutical composition may trigger or strengthen the immune response of the human or animal body to that disease state. In such cases, the peptide portion of the compound of the invention may be other than an immunogen associated with the same disease state. For example, the peptide portion may be non-immunogenic, or may be an immunogen which is not associated with the disease state. Alternatively, an immunogen may be a peptide covalently lined to the immunostimulant and the vector.

The immunogen may be derived from an infectious agent (pathogen), such as a virus, bacterium, *mycobacterium*, parasite or fungus, from an autologous protein, such as a cancer antigen (protein derived from a tumour cell), or from an allergen.

Thus, the invention provides a method of stimulating an immune response and/or treating a pathogenic infection, cancer or an autoimmune disease in a subject in need thereof. The subject may be human or animal, preferably a human. The animal is typically a vertebrate, such as a jawed vertebrate.

Examples of viruses include and are not limited to animal and human viruses such as: influenza, Human Immunodeficiency Virus (HIV), Hepatitis C Virus (HCV), Hepatitis B Virus (HBV), Hepatitis A Virus (HAV), Respiratory Syncytial Virus (RSV), Venezuelan Equine Encephalitis virus (VEE), Japanese Encephalitis virus (JEV), Cytomegalovirus (CMV), Epstein Barr Virus (EBV), Herpes Virus (HSV-1 or HSV-2), Ebola, Marburg, Dengue, West Nile and Yellow fever viruses, Porcine reproductive and respiratory syndrome virus (PRRSV) and Feline Immunodeficiency Virus (FIV).

Examples of bacteria and mycobacteria include, but are not limited to *Mycobacterium tuberculosis, Legionella*, Rickettsiae, Chlamydiae, and *Listeria monocytogenes.*

Examples of parasites include, but are not limited to *Plasmodium falciparum* and other species of the Plasmodial family.

Examples of fungi include, but are not limited to *Candida albicans, Cryptococcus, Rhodotorula* and *Pneumocystis.*

Autologous or self-antigens include, but are not limited to the following antigens associated with cancers, P53, MAGE-A3, NY-ESO-1, SURVIVIN, WT1, HER-2/neu, MUC 1, hTERT, MAGE-1, LAGE-1, PAP, T21, TRP-2, PSA, Livin, HAGE, SSX-1, PRAME, PASD1, IMP-3, SSX-4, CDCA-1 and/or BAGE.

Allergens include, but are not limited to, phospholipase A2 (API ml) associated with severe reactions to bee, Derp-2, Der p 2, Der f, Der p 5 and Der p 7 associated with reaction against the house-dust mite *Dermatophagoides pteronyssinus*, the cockroach allergen Bla g 2 and the major birch pollen allergen Bet v 1.

In one embodiment, the immunogen is a peptide derived from the influenza virus. The influenza peptide antigen may comprise one or more epitopes from an influenza type A protein, an influenza type B protein or an influenza type C protein. Examples of the influenza virus proteins, from both the influenza A and B types, include: haemagglutinin, neuraminidase, matrix (M1) protein, M2, nucleoprotein (NP), PA, PB1, PB2, NS1 or NS2 in any such combination. Examples of influenza peptide antigens are given in WO 2009/027688 and WO 2012/090002, both of which are incorporated herein in their entireties by reference.

As used herein the term immunogen refers to a molecule having the ability to be recognised by immunological receptors such as T cell receptor (TCR) or B cell receptor (BCR or antibody). The immunogen may be natural or non-natural, provided it presents at least one epitope, for example a T cell and/or a B cell epitope. T cell and B cell epitopes represent the active part of the immunogen, and it is these epitopes that are recognised by the adaptive immune system. The peptide may contain one or more T cell epitopes, including T helper cell epitopes and/or cytotoxic T lymphocyte (CTL) epitopes, and/or one or more B cell epitopes or combinations of T and B cell epitopes, such as MHC class I or MHC class II epitopes. Methods for identifying epitopes are well known in the art. The epitopes may be overlapping linear epitopes so that the peptide comprises a cluster of densely packed multi-specific epitopes.

The pharmaceutical composition may include, or the methods may involve administration with, more than one immunogen. The immunogens may be associated with the same disease state, or with different disease states, and may have the same or different types of immunonological activity. For example, the immunogen may be a peptide immunogen which can stimulate a T cell response, and a B-cell antigen. It will be understood by vaccine designers that more than one immunogen may be required to provide a broader prophylactic or immunotherapeutic effect. Such multi-component products are desirable since they are likely to be more effective at eliciting appropriate immune responses. For example, the optimal formulation of an influenza vaccine may comprise a number of peptide epitopes from different influenza proteins or the optimal formulation of an HBV immunotherapeutic may comprise a number of epitopes from different HBV proteins. Alternatively, multiple epitopes may be incorporated into a formulation in order to confer immunity against a range of pathogens. For example a respiratory infection vaccine may contain epitopes from influenza virus and respiratory syncytial virus.

A pharmaceutical composition of the invention may comprise, or a method of the invention may comprise administration of, multiple immunogenic peptides. Typically each peptide comprises a different epitope.

The immunogen may be any suitable immunogen known in the art. Preferably, the immunogen is a peptide antigen. The peptide antigen may comprise at least one peptide from 15 to 60 amino acids in length. Thus, the peptide typically has a length of from 15 or 20 to 60 amino acids, such as from 25 to 50 amino acids, preferably from 30 to 40 amino acids, for example, 31, 32, 33, 34, 35, 36, 37, 38 or 39 amino acids.

The peptide antigen must include at least one epitope, but may include additional amino acids. The additional amino acids may facilitate manufacture or formulation of the peptide or enhance stability of the peptide. For example, the peptide may comprise one or more additional amino acids, typically at the N-terminus and/or the C-terminus to enhance the net positive charge of the peptide and/or to reduce the hydrophobicity of the peptide. The net positive charge may be increased so that the peptide has an isoelectric point greater than or equal to 7.

The peptide antigen may have one or more, such as two or three positively charged amino acids (arginine and/or lysine), added to the N- and/or C-terminus. For example, three lysine residues may be added to the N- and/or C-terminus of one or more of the peptides. Positive amino acids are typically added at the end(s) of peptides that have an overall hydrophobicity of more than 65%, a net charge of less than zero and/or include cluster of hydrophobic amino acids.

The peptide antigen may comprise one or more long (approximately 35-mer) peptides that encompass short minimal epitopes. These peptides are typically more effective immunogens than peptides consisting of the minimal epitopes. The peptide antigen may have a tertiary structure that may protect it from exopeptidase-mediated degradation, and may be too long to be presented directly on HLA; so that it must be internalized by professional APC and processed for presentation. The peptide antigens may each comprise at least one CD8+ T-cell (HLA Class I) and at least one CD4+ T-cell (HLA Class II) epitope.

Unlike short peptides, such long peptides induce memory CD8+ T-cell responses that are boosted dramatically on repeat vaccination in mice, and induce substantially improved tumour control compared to vaccination with short peptides. Induction of CD4+ helper T-cells reactive to epitopes within the long peptides is also necessary for long term T-cell memory. The vaccine, and preferably each peptide in the vaccine, contains epitopes that activate CD8+ and CD4+ T-cell responses in individuals with different HLA backgrounds. Thus, the vaccine of the invention has broad population coverage and induces a durable immune response against tumour antigens.

The peptide antigen may comprise a fusion peptide where a promiscuous T helper epitope is covalently linked (optionally via a polypeptide linker or a spacer) to an antigenic consensus sequence. As an example, the promiscuous T helper epitope can be the PADRE peptide, tetanus toxoid peptide (830-843) or influenza haemagglutinin, HA (307-319).

The immunogen may comprise further, non-immunogenic, portions. For example, the immunogen (whether based on a peptidic or non-peptidic antigen moiety) may further comprise one or more non-peptide portions. The amino acid residues of any peptide portions (whether immunogenic or not) may be modified, such as to modify the physicochemical properties of the immunogen. In particular, terminal amino acids may be added or modified. Where a desired peptide is sensitive to cleavage by peptidases, the normal peptide bond can be replaced by a non-cleavable peptide mimetic. Such bonds and methods of synthesis are well known in the art.

The immunogen may comprise a vector portion such as that described above for the compound of the invention. In particular, the immunogen may comprise one or more peptide immunogens having a fluorocarbon vector portion as described above. The fluorocarbon vector portion may be modified such that the resulting compound is still capable of delivering the peptide to antigen-presenting cells. Thus, for example, a number of the fluorine atoms may be replaced with other halogen atoms such as chlorine, bromine or iodine. In addition, it is possible to replace a number of the fluorine atoms with methyl groups and still retain the properties of the molecule described herein.

Where the pharmaceutical composition comprises a discrete phase suspended in a continuous phase, the immunogen may be localised to the discrete phase. For example, the immunogen may comprise a vector portion which is adhered to the surface of, or embedded in, the discrete phase, in a similar manner to that described above for the compound of the invention.

Each peptide may be linked to a common fluorocarbon vector portion. More practically, combinations of fluorocarbon-linked peptides may be present in a formulation of the invention, wherein different peptides are independently linked to fluorocarbon chains. In a mixture of fluorocarbon-linked peptides, each peptide may be linked to a fluorocarbon chain of a single structure. Alternatively, the mixture may comprise peptides linked to fluorocarbon chains with different structures.

Preferably, where the immunogen is a fluorocarbon-linked peptide, the immunostimulant used to enhance the immune response to the immunogen also comprises a fluorocarbon vector.

The concentrations of the compound and the immunogen in the pharmaceutical composition may be such that each instance of the discrete phase is associated with at least one compound of the invention and at least one immunogen. In this way, the compound and immunogen are delivered together to a human or animal and may be maintained in close proximity within the human or animal body following administration, due to their mutual association with the discrete phase. At the same time, because there is no covalent linkage between the immunogen and the compound, it may be possible to formulate pharmaceutical compositions having different relative amounts of the immunogen and immunostimulant, according to the requirements of each recipient or group of recipients.

Preparation

The pharmaceutical compositions of the invention can be prepared in any standard manner known in the art. For example, the components of the pharmaceutical composition may be solubilised to disperse the components and form a clear, homogeneous solution. This solution may be sterilised, such as by filtration, and then dried.

The term "solubilisation" is used herein to mean the dispersion of the compound, and optionally other components of the composition, in a solvent to form a visually clear solution that does not lose material upon sterile filtration. By "dispersion" is meant dissolution of the compound, and optionally other components of the composition, in order to disrupt particulates and achieve solubility.

The concentration of the compound in the solution typically is from about 0.1 mM to about 10 mM, such as about 0.5 mM, 1 mM, 2 mM, 2.5 mM or 5 mM. An example of a suitable concentration is about 10 mg/mL.

The input components for the pharmaceutical composition may be blended homogenously together to the desired ratios with any aggregates dispersed, rendered sterile and presented in a suitable format for administration. Such examples could include the introduction of a vortexing and/or sonication post-blending or post-dilution stage to facilitate solubilisation. Other permutations of the manufacturing process flow could include sterile filtration being performed at an earlier stage of the process or the omission of lyophilisation to permit a liquid final presentation.

Examples of solvents that may be used to disperse the compound in the blend include phosphate buffered saline (PBS), propan-2-ol, tert-butanol, acetone, acetic acid and other organic solvents.

Where more than one solvent is used in the manufacturing process, each solvent used is typically: able to solubilise the component it is being used to solubilise at relatively high concentrations (for example, up to 10 millimolar, such as up to 2 millimolar); water-miscible to facilitate dilution with water prior to lyophilisation; compatible with lyophilisation stabilizers, such as mannitol, that may be used in the manufacturing process; has a safety profile acceptable to the pharmaceutical regulatory authorities, for example, complies with the requirements of ICH Q3C (Note for Guidance on Impurities: Residual Solvents) and the requirements of Class III solvents, as defined by USP Residual Solvents <467> (residual solvent limit of 50 mg/day in finished product or less than 5000 ppm or 0.5%); amenable to lyophilisation, that is, sufficiently volatile to be removed to safe levels upon lyophilisation; able to disperse the component molecules efficiently in a reproducible and uniform manner such that yield losses on sterilising grade filtration are minimised; unable to react with, or promote degradation of, the compound or component; and/or compatible with the materials routinely used in pharmaceutical product manufacture (containers/filter membranes/pipework etc).

Where the compound and another component, such as an immunogen, are solubilised separately, for example in different solvents or in different concentrations of acetic acid, the solubilised compound and other solubilised components are blended to create a mixture.

The compound is typically desiccated. Compounds that comprise a peptide portion shorter than 20 amino acids and/or that have fewer than 50% hydrophobic residues may generally be solubilised in a solvent other than acetic acid. Acetic acid is typically used where the peptide portion has more than 20 amino acids and/or has more than 50% hydrophobic residues.

After solubilisation and blending, the solution of the compound and optionally other components may be diluted. For example, the blend may be diluted in water.

The solution containing the compound is preferably sterilised. Sterilisation is particularly preferred where the formulation is intended for systemic use. Any suitable means of sterilisation may be used, such as UV sterilisation or filter sterilisation. Preferably, filter sterilisation is used. Sterile filtration may include a 0.45 μm filter followed by a 0.22 μm sterilizing grade filter train. Sterilisation may be carried out before or after addition of any excipients and/or adjuvants.

The pharmaceutical composition may be in dried, such as lyophilized, form. The composition of the invention may be an aqueous solution, for example an aqueous solution formed by dissolving a lyophilisate or other dried formulation in an aqueous medium. The aqueous solution is typically pH neutral.

Drying the formulation facilitates long-term storage. Any suitable drying method may be used. Lyophilisation is preferred but other suitable drying methods may be used, such as vacuum drying, spray-drying, spray freeze-drying or fluid bed drying. The drying procedure can result in the formation of an amorphous cake within which the compound of the invention is incorporated.

For long-term storage, the sterile composition may be lyophilized Lyophilisation can be achieved by freeze-drying. Freeze-drying typically includes freezing and then drying. For example, the composition component mixture may be frozen for 2 hours at −80° C. and freeze-dried in a freeze drying machine for 24 hours.

Variations to the process flow are permitted, as known to one skilled in the art, to achieve the same resulting product characteristics; namely, that the input components are blended homogenously together to the desired ratios with any aggregates dispersed, rendered sterile and presented in a suitable format for administration. Such examples could include the introduction of a vortexing and/or sonication post-blending or post-dilution stage to facilitate solubilisation. Other permutations of the manufacturing process flow could include sterile filtration being performed at an earlier stage of the process or the omission of lyophilisation to permit a liquid final presentation.

Pharmaceutically acceptable compositions of the invention may be solid compositions. The composition may be obtained in a dry powder form. A cake resulting from lyophilisation can be milled into powder form. A solid composition according to the invention thus may take the form of free-flowing particles. The solid composition typically is provided as a powder in a sealed vial, ampoule or syringe. If for inhalation, the powder can be provided in a dry powder inhaler. The solid matrix can alternatively be provided as a patch. A powder may be compressed into tablet form.

The dried, for example, lyophilized, composition may be reconstituted prior to administration. As used herein, the term "reconstitution" is understood to mean dissolution of the dried vaccine product prior to use. Following drying, such as lyophilisation, the compound preferably is reconstituted to form an isotonic, pH neutral, homogeneous suspension. The formulation is typically reconstituted in the aqueous phase, for example by adding Water for Injection, histidine buffer solution (such as 28 mM L-histidine buffer), sodium bicarbonate, Tris-HCl or phosphate buffered saline (PBS). The reconstituted formulation is typically dispensed into sterile containers, such as vials, syringes or any other suitable format for storage or administration.

The composition may be stored in a container, such as a sterile vial or syringe, prior to use.

Where the composition comprises a fluorocarbon, the fluorocarbon-containing compound may be present in a multimolecular micellar structure. The fluorocarbon-containing compound may be the compound of the invention (such as with a fluorocarbon-based vector portion), or a fluorocarbon-containing immunogen or both. These components may be solubilised in acetic acid to promote micelle formation. In particular, approaches for solubilising fluorocarbon vector-peptide conjugates, such as will be relevant where the compound comprises a vector comprising a fluorocarbon moiety, are described in WO 2012/090002.

EXAMPLES

The following Examples illustrate the invention.

Example 1

An immunostimulant is prepared according to the reaction scheme of Scheme 1:

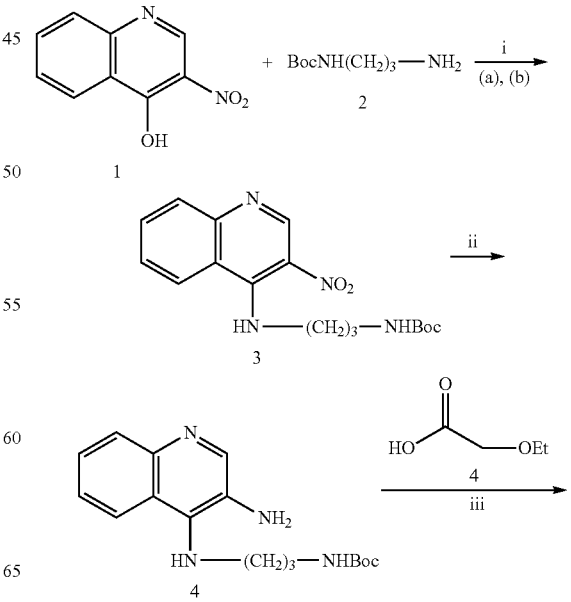

29
-continued
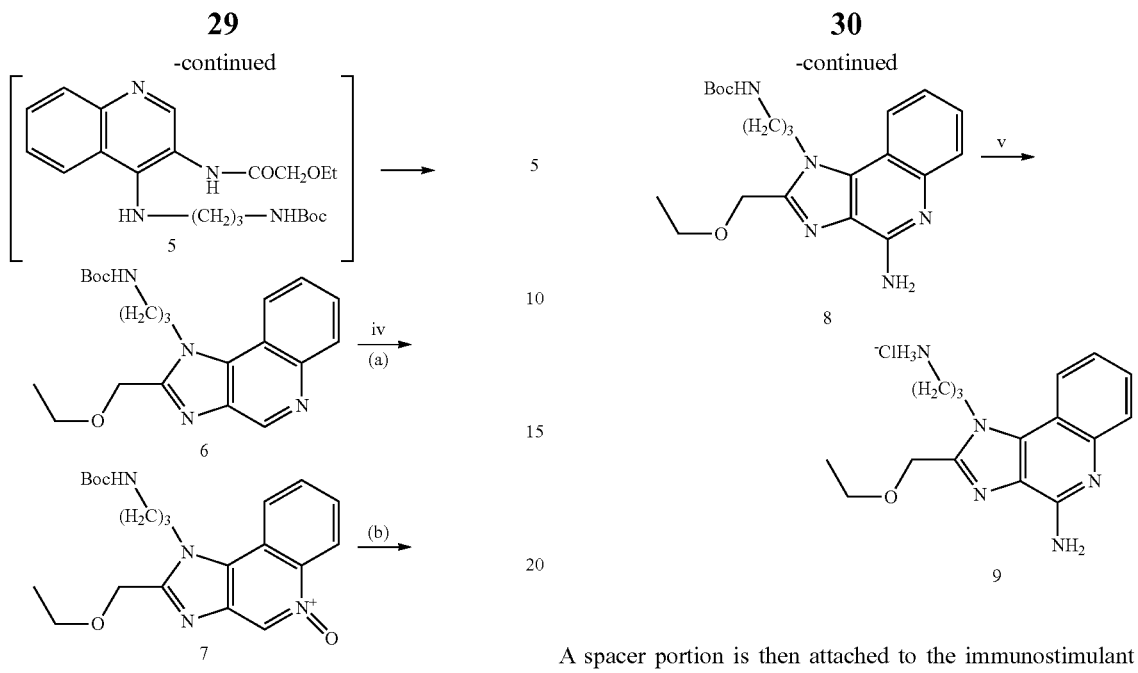
30
-continued
A spacer portion is then attached to the immunostimulant portion according to Scheme 2:
Scheme 2
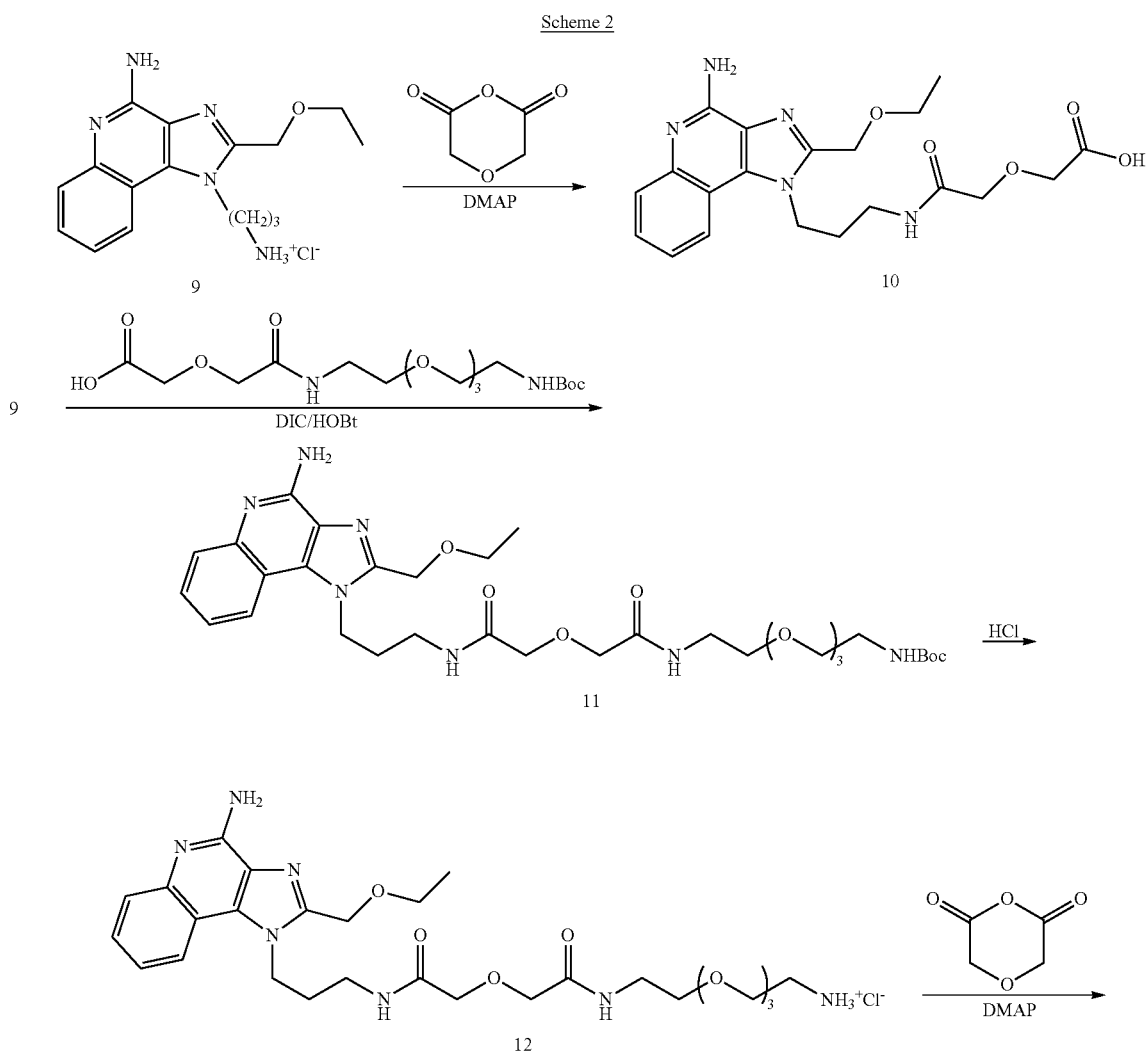

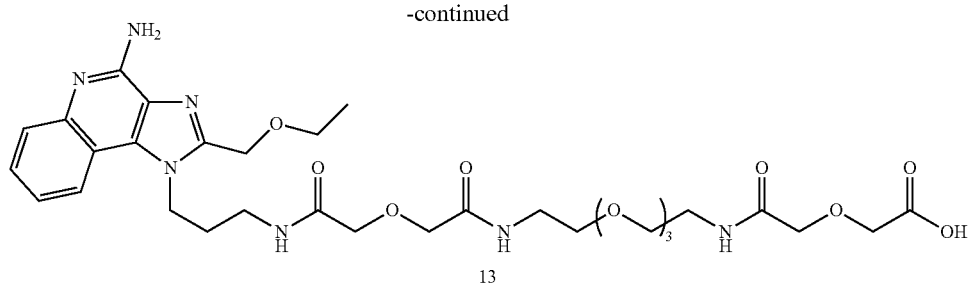
13
A peptide portion is prepared using solid-phase peptide synthesis, functionalised at the N-terminus with a fluorocarbon vector portion, functionalised at the C-terminus with the above immunostimulant-spacer portion, and then cleaved from the resin to give the compound of the invention, as shown in Scheme 3:
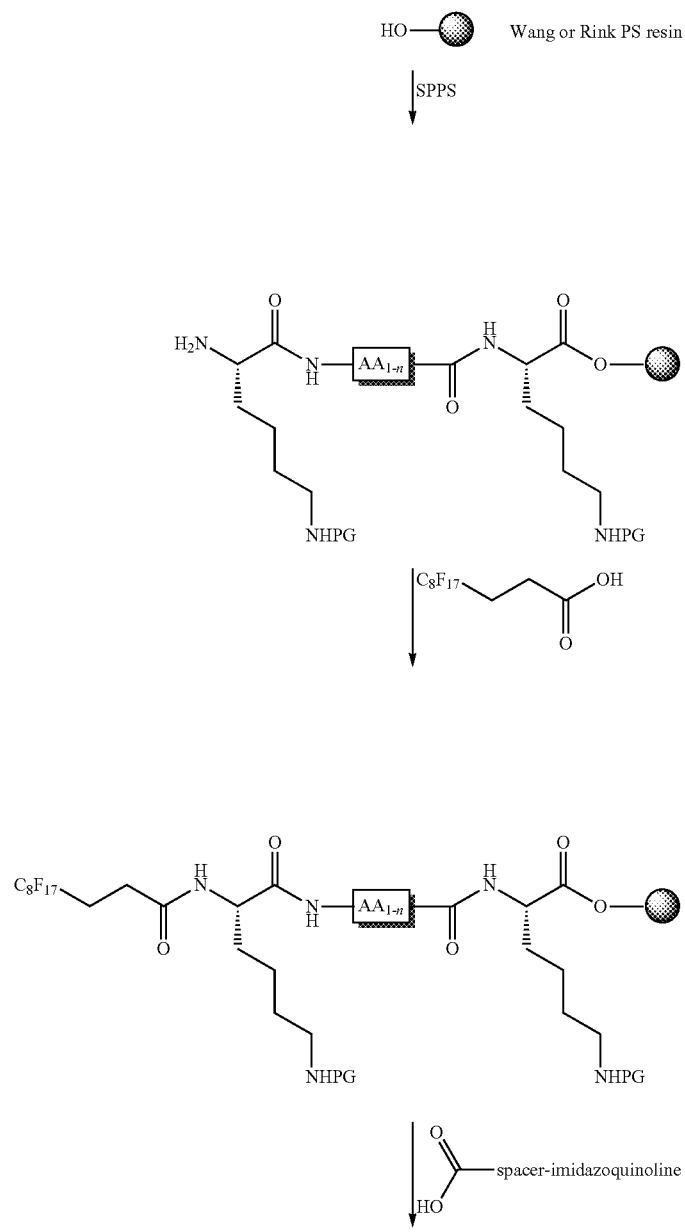

-continued

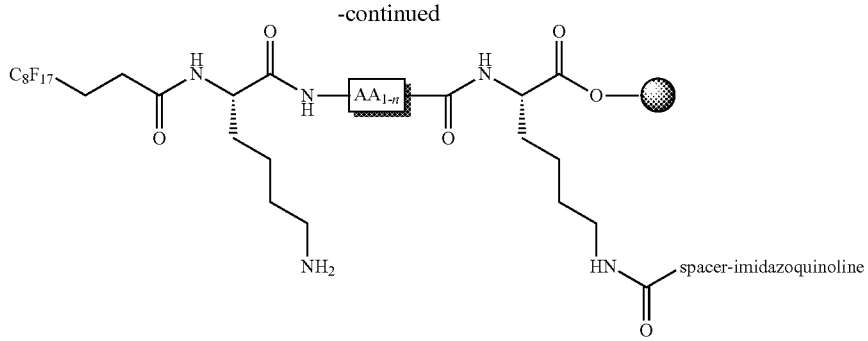

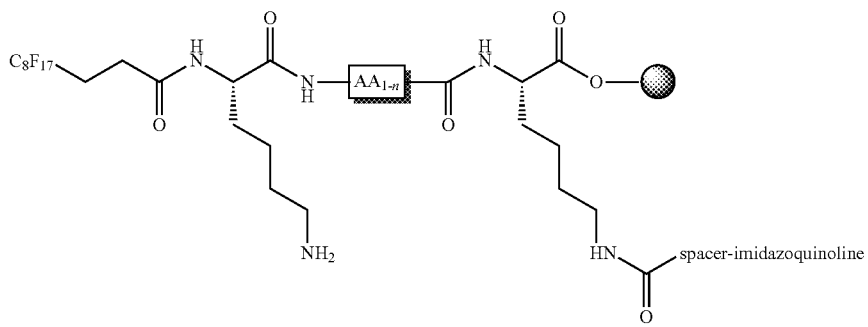

PG = protecting group

The compound is solubilised in acetic acid so that the fluorocarbon vector portion self-assembles into a multimolecular micelle-like structure. The solution is diluted with water, filtered for sterilisation, and then lyophilised to give a dry powder.

Example 2

Materials and Methods

Immune Stimulants

Compound "R848" is 1-[4-Amino-2-(ethoxymethyl)-1H-imidazo[4,5-c]quinolin-1-yl]-2-methyl-2-propanol, HCl, having the structure

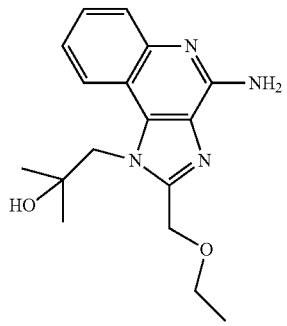 [SMILES: CCOCc1nc2c(N)nc3ccccc3c2n1CC(C)(C)O]

In the compounds below, "$FA_1$" is $C_8F_{17}(CH_2)_2CO-$, "Ac"=$CH_3CO-$, "PEG" is $-CO((CH_2)_2O)_3NH-$, and "FIM" is 1-[4-amino-2-(ethoxymethyl)1H-imidazo[4,5-c]quinolin-1-yl]-propanamino-diglycolyl-.

Compound "PEG-FIM-01" is K(Ac)RRLLHAHLAL-HAHLLRRLK(PEG-FIM)-$NH_2$, having the structure

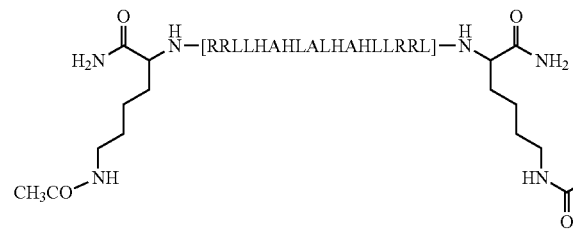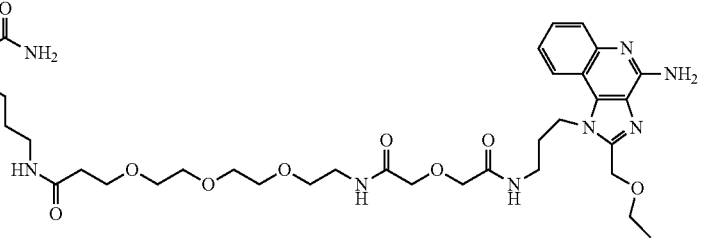

Compound "FA-PEG-FIM-01" is K(FA$_1$)RRLLHAHLA-LHAHLLRRLK(PEG-FIM)-NH$_2$, having the structure

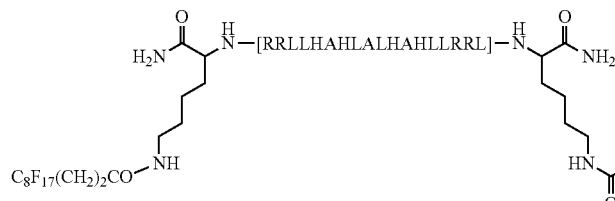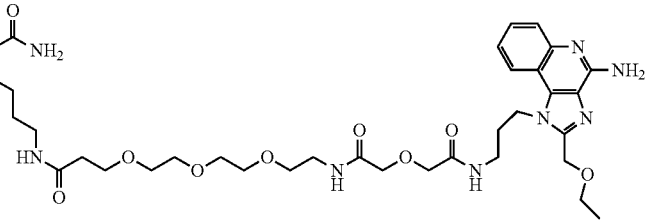

Compound "FA-FIM-01" is K(FA$_1$)RRLLHAHLAL-HAHLLRRLK(FIM)-NH$_2$, having the structure

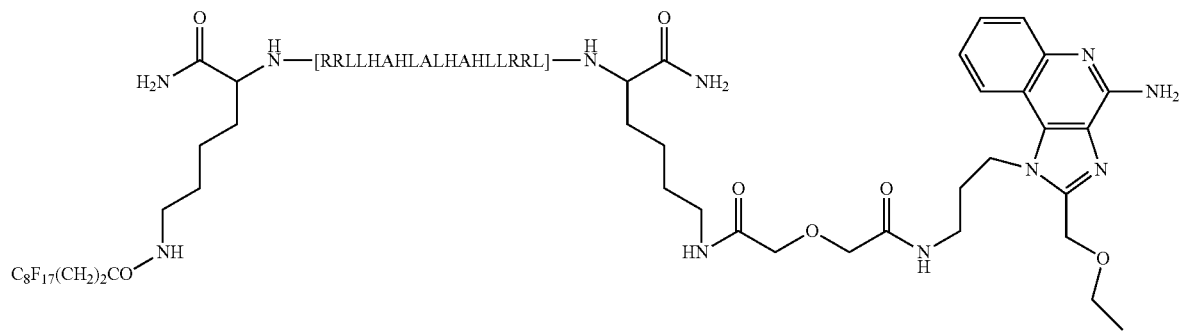

Compound "RLK-PEG-FIM-01" is RLK(PEG-FIM)-NH$_2$, having the structure

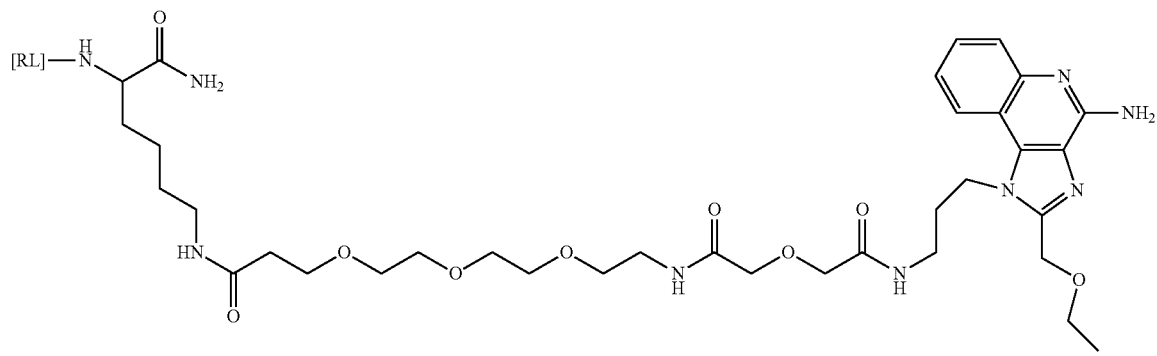

Hemagglutinin Antigen

Recombinant hemagglutinin antigen HA (influenza A/California/07/2009 H1N1 sequence) produced in insect cells was obtained from Protein Sciences Corporation (Protein sciences, Cat # IT-003-SW12DTMp). The antigen has purity greater than 90% and is tested for sterility and pyrogenicity. The HA antigen was reconstituted in 28 mM histidine before injection.

FP-02.2 Vaccine Composition and Manufacture

FP-02.2 is a vaccine composed of 9 long peptides ranging from 32 to 41 amino-acids (Table 3). Each peptide was manufactured using Fmoc (fluorenylmethyloxycarbonyl chloride) solid-phase peptide synthesis. After completion of the peptide elongation on the resin, a fluorocarbon vector was attached to the epsilon side chain of an additional N-terminal lysine. Following cleavage and deprotection, each peptide was purified by RP-HPLC. After acetate exchange, each peptide was freeze-dried and stored at −20° C. All peptides were produced at a purity >95%. For the manufacture of FP-02.2, each peptide was re-suspended in water+acetic acid. After blending and dilution with a mannitol/water solution, the formulation was filtered using a 0.22 μm filter. The filtered solution was aliquoted in glass vials before freeze-drying. The FP-02.2 vaccine was reconstituted in 28 mM L-histidine before injection (unless stated otherwise).

TABLE 3

| | |
|---|---|
| FA-P113 | K(FA1)-VGPLTVNEKRRLKLIMPARFYPNVTKYLPLDKGIK-CONH$_2$ |
| FA-P151 | K(FA1)-PEHVVNHYFQTRHYLHTLWKAGILYKRETTRSASF-CONH$_2$ |
| FA-P277(K) | K(FA1)-RVSWPKFAVPNLQSLTNLLSSNLSWLSLDVSAAFYHKKK-CONH$_2$ |
| FA-P376 | K(FA1)-KLHLYSHPIILGFRKIPMGVGLSPFLLAQFTSAISSVVRR-CONH$_2$ |
| FA-P753(K) | K(FA1)-KKKEFGATVELLSFLPSDFFPSVRDLLDTASALYR KKK-CONH$_2$ |
| FA-P797(K) | K(FA1)-SPHHTALRQAILSWGELMTLATWVGSNLEDPASRDKKK-CONH$_2$ |
| FA-P856(K) | K(FA1)- LTFGRETVLEYLVSFGVWIRTPPAYRPPNAPILSTKKK-CONH$_2$ |
| FA-P877 | K(FA1)- PPAYRPPNAPILSTLPETTVVRRRGRSPRRR-CONH$_2$ |
| FA-P1266(K) | K(FA1)-KKKGPLLVLQAGFFLLTRILTIPQSLDSWWTSLNFLKKK-CONH$_2$ |

Peptide Antigens Used for In Vitro Restimulation

Each peptide described in Table 4 was synthesized using Fmoc solid-phase chemistry. After cleavage from the resin and deprotection, peptide purification was performed by RP-HPLC. After acetate exchange, each peptide was freeze-dried and stored at −20° C. All peptides were produced at a purity >90%.

TABLE 4

| | |
|---|---|
| P113 | VGPLTVNEKRRLKLIMPARFYPNVTKYLPLDKGIK |
| P151 | PEHVVNHYFQTRHYLHTLWKAGILYKRETTRSASF |
| P277(K) | RVSWPKFAVPNLQSLTNLLSSNLSWLSLDVSAAFYHKKK |
| P376 | KLHLYSHPIILGFRKIPMGVGLSPFLLAQFTSAISSVVRR |
| P753(K) | KKKEFGATVELLSFLPSDFFPSVRDLLDTASALYRKKK |
| P797(K) | SPHHTALRQAILSWGELMTLATWVGSNLEDPASRDKKK |
| P856(K) | LTFGRETVLEYLVSFGVWIRTPPAYRPPNAPILSTKKK |
| P877 | PPAYRPPNAPILSTLPETTVVRRRGRSPRRR |
| P1266(K) | GPLLVLQAGFFLLTRILTIPQSLDSWWTSLNFLKKK |
| CTL epitope 151 | HYFQTRHYL |

Animal Immunisation, Blood Sampling and Spleen Harvest

Female BALB/c mice were immunised intramuscularly with 50 μL vaccine containing 25 mcg/peptide FP-02.2 or 12.5 mcg of recombinant protein±test adjuvants or vehicle only on the inside back leg. For serum cytokine analysis, blood samples were taken 1 or 4 hours post-immunisation by tail vein puncture or cardiac puncture following cervical dislocation. Serum was isolated by centrifuging clotted blood samples for 10 minutes at 14000 rpm and stored at −20° C. For immunogenicity analysis, mice were culled 11 or 14 days after the last immunisation, spleens were harvested and single splenocyte suspensions were prepared to a density of $10^7$ cells/mL. All animal procedures were carried out following Home Office regulations.

IFN-Gamma ELISpot Assay $5 \times 10^5$ splenocytes were re-stimulated in vitro with 10 mcg each FP-02.2 component peptide or 5 mcg of HA antigen for 18 hours at 37° C./5% $CO_2$ in an IFN-γ ELISpot assay (BD Biosciences). Numbers of IFN-γ spot-forming cells (SFC) were counted using an automated plate counting system (CTL Europe) and normalized to SFC/$10^6$ splenocytes.

Antibody Titer

Plasma HA-specific total IgG, IgG1 or IgG2a were measured by means of ELISA. Maxisorb (nunc) plates were coated overnight at 4° C. with rHA from A/California/7/2009 (Protein sciences, Cat # IT-003-SW12DTMp) at 0.22 mg/mL. Plates were blocked with 2% FCS/PBS for 2 hours at rt. A 7-fold 1:10 serial dilution of plasma was performed in 1% BSA/PBS for individual mouse plasma, starting at a dilution of 1:100. Diluted plasma was incubated at room temperature for 4 hours. Plates were washed and a 1:4000 dilution of goat anti-mouse IgG1-HRP or IgG2a-HRP (both AbD Serotech) or IgG-HRP (KPL) was applied for 1.5 hours at RT. Plates were washed and 100 mL of substrate solution added (1-step ultra TMB-ELISA, Thermo Scientific). After 3 minutes 50 mL of 2M sulphuric acid was added and the adsorbance was read at 450 nm.

Cytometric Bead Array and ELISA for Cytokine Analysis of Serum Samples

Serum samples were diluted 1:4 in PBS and soluble cytokine concentrations (IFN-gamma, TNF-alpha, MCP-1, IL-6 and IL-10) were measured using Cytometric Bead Array (BD Biosciences). IFN-alpha was measured by ELISA (eBioscience Platinum ELISA).

Human TLR7 and TLR8 Reporter Gene Assays

The activity of different TLR-7 or TLR-8 agonist were tested using human TLR-specific HEK-Blue™ reporter gene assays (Invivogen, France). HEK-Blue™-hTLR7 cells and HEK-Blue™-hTLR8 cells were obtained by co-transfection of the human TLR7 gene or human TLR8 genes and an inducible SEAP (secreted embryonic alkaline phosphatase) reporter gene into HEK293 cells. The SEAP gene is placed under the control of the IFN-β minimal promoter fused to five NF-kappaB and AP-1-binding sites. Stimulation with a TLR ligand activates NF-kappaB and AP-1 which induce the production of SEAP. Cells were maintained in HEK-Blue™ selection medium containing Blasticidin, Zeocin and Normocin. HEK-Blue™ cells were incubated at a density of $10^5$ cells/mL in a volume of 200 ul in 96 well plates. In the presence of the HEK-Blue™ detection media, the secretion of SEAP (proportional to the to the NF-kappaB induction) was quantified at 620 nM.

Results
Improvement of the Immunogenicity of a Recombinant Protein in Combination with Different Immunostimulant-Peptide Conjugates Female BALB/c mice (n=6 or 7 per group) were immunised twice (2 weeks apart) with 12.5 mcg HA alone (group 1) or in addition with 13.2 µg of PEG-FIM-01 (group 2) or 15 µg of PEG-FIM-01 (group 3) corresponding to equimolar doses. 11 Days after immunization, splenocytes were collected and restimulated in vitro with the HA antigen before measuring the immune response by mean of an IFN-gamma ELISpot assay. Results are presented in FIG. 1.

Co-formulating the recombinant hemagglutinin (from Influenza-A H1N1) with FA-PEG-FIM-01 or PEG-FIM-01 significantly enhanced the immunogenicity by 25.2- and 15.3-fold respectively compared to recombinant hemagglutinin alone [P values: p=0.0316 (Group 2:Group 1); p<0.0001 (Group 3:Group 1)]. This result demonstrates the strong immunostimulatory properties of the imidazoquinoline moiety covalently linked to the peptide portion. In addition, the presence of the hydrophobic vector ($FA_1$) on the N-terminus of the immunostimulatory-peptide conjugate (FA-PEG-FIM-01) resulted in a 71% improvement of the cell-mediated immune response compared to PEG-FIM-01.

Plasma HA-specific total IgG, IgG1 or IgG2a were also measured (FIG. 2). Results showed significant improvement of the humoral response against the HA antigen when administered with FA-PEG-FIM-01 or PEG-FIM-01.

Both immunostimulatory-peptide conjugates are not anticipated to bind to the HA antigen. Visual appearance changes were not observed when co-formulating the immunostimulatory peptide conjugates and the antigen. This demonstrates that both immune-stimulatory conjugates improve the immune response in the absence of physical interaction between the immune stimulant and the antigen as previously postulated by Wille-Reece et al. Proc Natl Acad Sci USA. 2005 Oct. 18; 102(42):15190-4).

Improvement of the Immunogenicity of a Peptide Vaccine in Combination with Different Immunostimulant-Peptide Conjugates Female BALB/c mice (n=6 per group) were immunised on a single occasion with FP-02.2 (25 mcg/peptide) alone (group 1), FP-02.2 (25 mcg/peptide)+FA-FIM-01 (5 mcg) (group 2), FP-02.2 (25 mcg/peptide)+FA-PEG-FIM-01 (5 mcg) (group 3). 14 Days after immunization, splenocytes were collected and restimulated in vitro with the FP-02.2 peptide antigens before measuring the immune response by mean of an IFN-gamma ELISpot assay. Results are presented in FIG. 3.

Both FA-PIM-01 and FA-PEG-PIM-01 in combination with FP-02.2 enhanced the magnitude of response by 2.4- and 3.1-fold respectively relative to FP-02.2 alone. Compared to FA-FIM-01, the presence of the pegylated portion within the FA-PEG-FIM-01 construct further enhanced the overall immune response by 26%. More specifically, the presence of the pegylated portion increased the immune response by 40, 9, 117, 41 and 60% for peptides P113, P151, P376, P856 and P1266(K) respectively.

Improved Vaccine Immunogenicity in the Presence of an Immunostimulant-Peptide Conjugate at Different Doses Female BALB/c mice (n=6 per group) were immunised on a single occasion with FP-02.2 (25 mcg/peptide) alone (group 1) or in combination with FA-PEG-FIM-01 at doses varying 0.5, 1.58, 5, 15.8 and 50 mcg (groups 2,3,4,5 and 6 respectively). 14 Days after immunization, splenocytes were collected and restimulated in vitro with the FP-02.2 peptide antigens before measuring the immune response by mean of an IFN-gamma ELISpot assay. Results are presented in FIG. 4.

The addition of different doses of FA-PEG-FIM-01 to FP-02.2 significantly increased the overall vaccine immunogenicity compared to FP-02.2 alone. [P values: p=0.0191 (Group 2:Group 1); p=0.0409 (Group 3:Group 1); p=0.004 (Group 4: Group 1); p<0.0001 (Group 5:Group 1); p=0.0004 (Group 6:Group 1)]. Magnitude of response peaked at 15.8 μg FA-PEG-PIM-01. This provided an overall 5.9-fold increase in magnitude relative to non-adjuvanted FP-02.2. The presence of the immune stimulant also increased the breadth of response moving from 3 immunogenic peptides in FP02.2 alone to 6 immunogenic peptides at a higher dose of FA-PEG-PIM-01.

Superior Adjuvanticity of the Immunostimulant-Peptide Conjugate Compared to the Free Immune Stimulant R848

Female BALB/c mice (n=4 per group) were immunised on a single occasion with FP-02.2 25 mcg/peptide alone (group 1) or in combination with FA-PEG-FIM-01 15 mcg (group 2), R848 1.5 mcg (group 3), R848 10 mcg (group 4) and R848 50 mcg (group 5). 14 Days after immunization, splenocytes were collected and restimulated in vitro with the FP-02.2 peptide antigens before measuring the immune response by mean of an IFN-gamma ELISpot assay. Results are presented in FIG. 5.

Surprisingly, the addition of FA-PEG-FIM-01 to FP-02.2 significantly increased the overall vaccine immunogenicity compared to FP-02.2 alone as opposed R848. The superiority of the immunostimulatory peptide conjugate over the free immune stimulant was observed at an equimolar dose but also at higher doses.

Key Role Played by the Peptide Portion in the Vaccine Adjuvanticity of Immunostimulant-Peptide Conjugates Female BALB/c mice (n=8 per group) were immunised on a single occasion with FP-02.2 25 mcg/peptide alone (control group) or in combination with FA-PEG-FIM-01 15 mcg (group 1), PEG-FIM-01 13.15 mcg (group 2), (3) RLK-PEG-FIM-01 4.3 mcg (group 3) or (4) R848 1.5 mcg (group 4) corresponding to equimolar doses. Results are presented in FIG. 6.

Both FA-PEG-PIM-01 and PEG-FIM-01 enhance the magnitude of response relative to FP-02.2 compared to-PEG-PIM-01 and PEG-FIM-01. This establishes the key role played by the peptide portion in the adjuvanticity of the immunostimulatory-peptide conjugates. As observed in FIG. 6, the presence of the hydrophobic vector ($FA_1$) on the N-terminus of the immunostimulatory-peptide conjugate (FA-PEG-FIM-01) resulted in an improvement of the cell-mediated immune response compared to PEG-FIM-01.

Absence of Systemic Pro-Inflammatory Responses with an Immunostimulatory Peptide Conjugate as Opposed to a Free Immune Stimulant Counterpart R848

Female BALB/c mice (n=4 per group) were injected on a single occasion with (1) 28 mM L-Histidine vehicle only, (2) R848 (1.5 mcg) in 28 mM L-Histidine, (3) FA-PEG-FIM-01 (15 mcg) in 28 mM L-Histidine, (4) FA-PEG-FIM-01 (15 mcg) in Phosphate 10 mM (n=4 per group) corresponding to equimolar doses. Blood samples were taken at 1 and 4 hours. Serum cytokine concentrations were measured using cytometric bead array (MCP-1, IL-6, TNF-alpha, IFN-gamma, IL-10 and IL-12p70) or ELISA (IFN-alpha). Results are presented in FIG. 7.

Surprisingly, pro-inflammatory cytokines were only observed at 1 or 4 hours in animals receiving R848. IFN-alpha (8851±2641 pg/mL), IL-6 (15±7 pg/mL) and TNF-α (9±10 pg/mL) production peaked at 1 hour, while MCP-1

(4749±2083 pg/mL) and IFN-gamma (20±13 pg/mL) production peaked at 4 hours. IL-10 and IL-12p70 were not detected at either time point in any group. The induction of pro-inflammatory cytokines with R848 reflects the rapid systemic diffusion of the small molecule.

Figure 8:
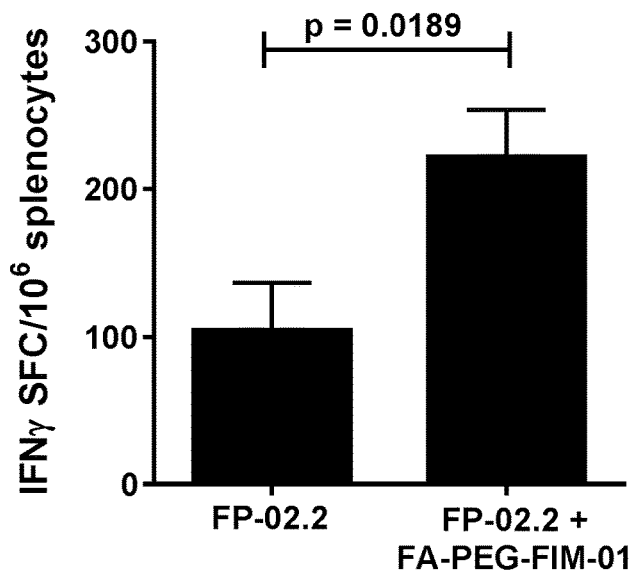
FIG. 8 depicts improved vaccine-induced CTL response in the presence of an immunostimulatory peptide conjugate, as demonstrated in the Examples. Female BALB/c mice were immunised with FP-02.2 alone or in addition with 15 μg PEG-FIM-01. Bars represent the mean number of spot forming cells induced by the CTL epitope 151 as measured in the IFN-g ELISpot assay. Statistical analysis was based on a Student's T test.

Improved Vaccine-Induced CTL Response in the Presence of an Immunostimulatory Peptide Conjugate Female BALB/c mice (n=8 per group) were immunised on a single occasion with FP-02.2 25 mcg/peptide alone or in combination with FA-PEG-FIM-01 15 mcg. 14 Days after immunization, splenocytes were collected and restimulated in vitro with the CTL epitope 151 before measuring the immune response by mean of an IFN-gamma ELISpot assay. Results are presented in FIG. 8. The results demonstrate the ability of FA-PEG-PIM-01 to enhance the CTL response induced by FP-02.2.

Specificity of the Immunostimulatory Peptide Conjugates for TLR-7 and TLR-8

Figure 9:
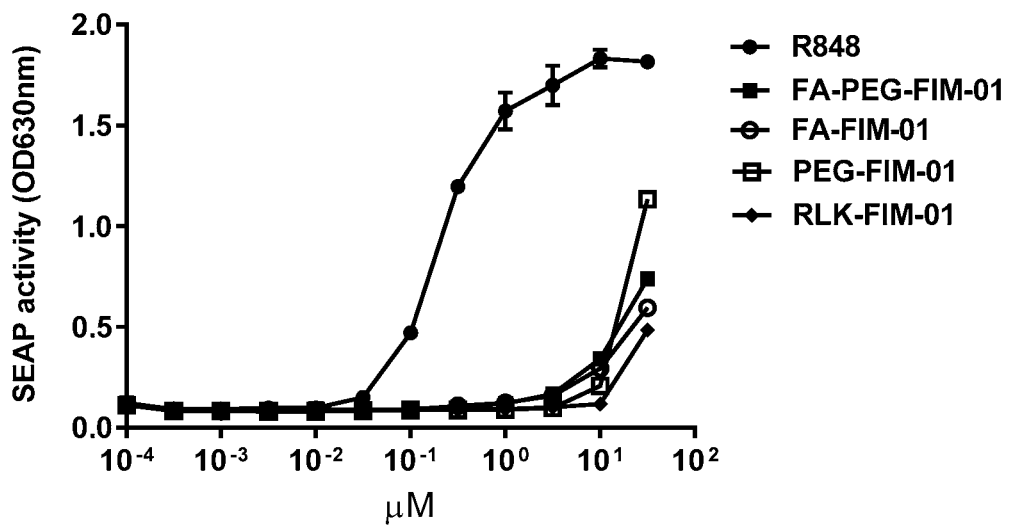
FIG. 9 depicts specificity of the immunostimulatory peptide conjugates for TLR-7 and TLR-8, as demonstrated in the Examples. FA-PEG-FIM-01, FA-FIM-01, RLK-PEG-FIM-01 and PEG-FIM-01 were tested for their ability to induce NF-kappaB activation in the HEK-293 cells expressing TLR-7 (A) and TLR-8 (B) in comparison with the R848.
Figure 9:
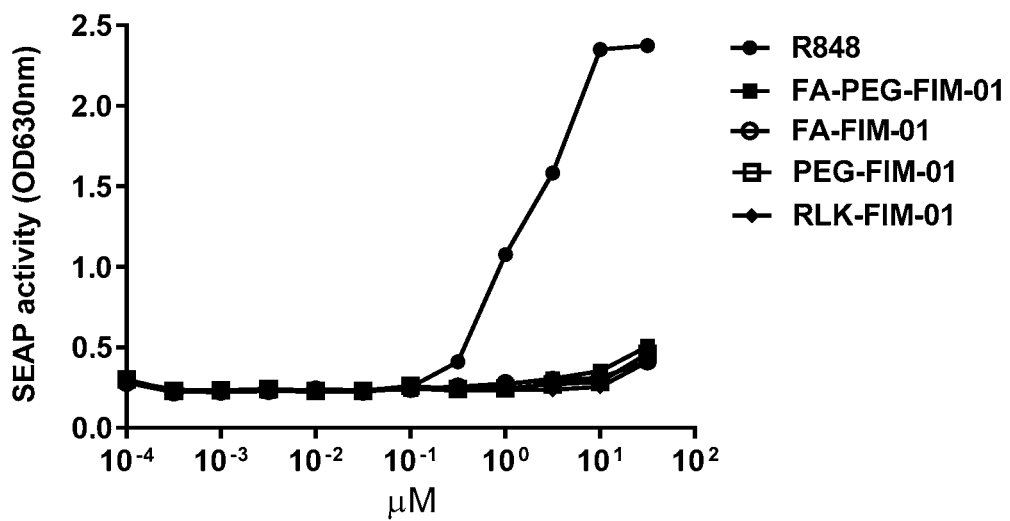

FA-PEG-FIM-01, FA-FIM-01, RLK-PEG-FIM-01 and PEG-FIM-01 were tested for their ability to induce NF-kappaB activation in the HEK-293 cells expressing TLR-7 and TLR-8 in comparison with the R848 (see FIG. 9). As expected, R848 was highly active in both cell lines. FA-PEG-FIM-01, FA-FIM-01, RLK-PEG-FIM-01 and PEG-FIM-01 were also active in the TLR-7 and TLR-8 cell line but to a much lesser extent compared to R848. These results were surprising in the light of the in vivo adjuvanticity data described above, which showed substantially improved in vivo adjuvanticity was achieved by the peptide conjugates compared with R848.

CONCLUSIONS

This example demonstrates that the adjuvanticity of immunostimulant-peptide conjugates can significantly enhance the immune response towards peptide or protein-based vaccines.

This effect is achieved in the absence of physical interaction between the immunostimulant-peptide conjugates and the antigen.

The example also demonstrates that the adjuvanticity of the immunostimulant-peptide conjugates is mainly driven by the presence of the peptide portion in its entirety.

This adjuvanticity can be further enhanced if a hydrophobic vector is attached to the extremity of the peptide and/or if a PEG spacer is introduced between the peptide and the immunostimulatory moiety.

Surprisingly, the immunostimulant-peptide conjugates are significantly superior to a free small immunostimulatory molecules (R848) providing little to no-adjuvanticity property.

In addition, immunostimulant-peptide conjugates do not promote the induction of systemic pro-inflammatory cytokines as opposed to a free small immunostimulatory molecule (R848). The induction of systemic pro-inflammatory cytokines by small immune stimulants has been associated with serious adverse events in humans.

The peptide portion selected to be incorporated in the immunostimulant-peptide conjugates support the retention of the construct at the administration site. This effect may be provided by the physico-chemical properties of the peptide portion driving the formation of aggregates under increased pH and/or ionic strength conditions compared to the reconstitution conditions.

The improvement in adjuvanticity and lack of systemic pro-inflammatory response associated with the immunostimulant-peptide conjugates support their use in animal and human as a vaccine adjuvant but also as a locally acting immune modulator (delivered through intratumoral, pulmonary, intranasal or intravesical administration).

As a result of the physico-chemical property of the peptide portion (hydrophobicity, charges), the immunostimulant-peptide conjugates have excellent solubility in reconstitution conditions.

Example 3—Impact of the Primary Sequence of the Peptide on the Formation of Aggregates as a Result of pH and Ionic Strength Changes Materials and Methods
Peptide and Peptide-Conjugates Compounds used in this Example are shown in Table 5 below. Peptides 16 and 16' correspond to the peptides incorporated in the conjugates of Example 2. Peptides 6, 8 and 10 have an amino acid sequence in which 75% or more of the amino acid residues are hydrophobic.

TABLE 5

| NAME | SEQUENCE | A (%) | B (%)* | C |
|---|---|---|---|---|
| Peptide 1 | Ac-RRLLPAPLALPAPLLRRL-NH$_2$ | 98.7 | 55.6 | 4 |
| Peptide 2 | Ac-RRLLPAALALAAPLLRRL-NH$_2$ | 98.6 | 66.7 | 4 |
| Peptide 3 | Ac-RRLLPALLALLAPLLRRL-NH$_2$ | 96.9 | 66.7 | 4 |
| Peptide 4 | Ac-RRLLLAPLALPALLLRRL-NH$_2$ | 94.3 | 66.7 | 4 |
| Peptide 5 | Ac-RRLLAAPLALPAALLRRL-NH$_2$ | 98.0 | 66.7 | 4 |
| Peptide 6 | Ac-LRLLHALLALLAHLLRLL-NH$_2$ | 93.9 | 77.8 | 4 |
| Peptide 7 | Ac-LRLLHAPLALPAHLLRLL-NH$_2$ | 96.3 | 66.7 | 4 |
| Peptide 8 | Ac-LRLLHAALALAAHLLRLL-NH$_2$ | 98.4 | 77.8 | 4 |
| Peptide 9 | Ac-LRLLPAHLALHAPLLRLL-NH$_2$ | 99.5 | 66.7 | 4 |
| Peptide 10 | Ac-LRLLAAHLALHAALLRLL-NH$_2$ | 99.1 | 77.8 | 4 |
| Peptide 11 | Ac-RRLLHALLALLAHLLRRL-NH$_2$ | 99.2 | 66.7 | 4 |
| Peptide 12 | Ac-RRLLHAPLALPAHLLRRL-NH$_2$ | 98.3 | 55.6 | 6 |

TABLE 5-continued

| NAME | SEQUENCE | A (%) | B (%)* | C |
|---|---|---|---|---|
| Peptide 13 | Ac-RRLLHAALALAAHLLRRL-NH$_2$ | 98.2 | 66.7 | 6 |
| Peptide 14 | Ac-RRLLPAHLALHAPLLRRL-NH$_2$ | 97.9 | 55.6 | 6 |
| Peptide 15 | Ac-RRLLAAHLALHAALLRRL-NH$_2$ | 97.8 | 66.7 | 6 |
| Peptide 16 | Ac-RRLLHAHLALHAHLLRRL-NH$_2$ | 92.3 | 55.6 | 8 |
| Peptide 17 | Ac-RRLLHAKLALKAHLLRRL-NH$_2$ | 92.0 | 55.6 | 8 |
| Peptide 18 | Ac-RRLLKAKLALKAKLLRRL-NH$_2$ | 97.9 | 55.6 | 8 |
| Peptide 19 | Ac-RRLKKAKLKLKAKKLRRL-NH$_2$ | 96.1 | 38.9 | 10 |
| Peptide 16' | K(Ac)RRLLHAHLALHAHLLRRLK(Ac)-NH$_2$ | 97.6 | 60** | 8 |
| PEG-FIM-01 | K(Ac)RRLLHAHLALHAHLLRRLK(PEG-FIM)-NH$_2$ | 95.3 | 60**/*** | 8 |
| FA-PEG-FIM-01 | K(FA1)RRLLHAHLALHAHLLRRLK(PEG-FIM)-NH$_2$ | 95.7 | 60**/*** | 8 |

A: RP-HPLC purity (%); B: Hydrophobicity (%); C: Number of positively charged amino acid residues.
FA$_1$ = C$_8$F$_{17}$(CH$_2$)$_2$CO—; Ac = CH$_3$CO—; PEG = —CO((CH$_2$)$_2$O)$_3$NH—; FIM = 1-[4-amino-2-(ethoxymethyl)1H-imidazo[4,5-c]quinolin-1-yl]-propanamino-diglycolyl-
*The degree of hydrophobicity is calculated based on the number of hydrophobic residues (L, A, G, W, Y, I, F, V, M) divided by total number of residues in the peptide sequence and was calculated for each peptide
**Acetylated lysine is considered hydrophobic
***Calculated for the peptide portion only All peptides were manufactured using solid phase synthesis (Fmoc chemistry) and purified by RP-HPLC. Peptides were produced with TFA as a counter-ion. Average purity was 97% ranging from 92.3 to 99.5% Amino-acid analysis was performed on all peptides and net mass were calculated from the results. All peptides were stored at −20° C.

Preparation of the Peptide Solutions

All solutions and samples were prepared in a laminar flow hood cabinet. Water, 28 mM L-Histidine buffer (HIST), 0.9% Sodium chloride (NaCl), 0.9% Sodium chloride in 28 mM L-histidine (NaCl/HIST) and 1X Phosphate buffer saline (PBS) were prepared the day before the analysis. Aqueous solutions were filtered twice using a 0.22 mcm filter, sonicated for 30 minutes and kept at room temperature. All borosilicate glass containers used for the preparation of the peptide solution were washed three time with filtered water. Peptides were re-suspended with the different aqueous solutions to achieve a concentration of 2 mg net mass/ml and vortexed for 30 second. pH was measured a sample from all peptide solutions. pH of the peptide/water solutions were ranging from 3.1 to 4.1. pH of the different peptide/28 mM L-Histidine solutions were ranging from 5.9 to 6.4. pH of the peptide/0.9% sodium chloride solutions were ranging from 3.3 to 4.2. pH of the peptide/0.9% sodium chloride in 28 mM L-Histidine solutions were ranging from 5.9 to 6.3. pH of the peptide/PBS solutions was ranging from 6.9 to 7.5. Peptide solutions were equilibrated at room temperature for 30 minutes and visually checked for the presence of insoluble aggregates. Visually clear peptide solutions were filtered using a sterile 0.45 mcm PVDF filter (first drop discarded). 150 mcL of the peptide solutions were carefully dispatched in an individually wrapped disposable microcuvette (ultra-micro z 8.5 mm, Brandtech, Lot 412806), capped and left at room temperature for 30 minutes.

Particle Size Measurement (Dynamic Light Scattering)

A Zetasizer Nano S (Malvern Instruments, UK) enabling measurement of particles from 0.6 nm to 6 microns was employed to monitor the particle size. Measurement were made at 20+/−0.1° C. Analyses were performed with the Dispersion Technology Software (Malvem Instruments, UK). Equilibration time was set to 2 minutes. Laser attenuation was set automatically by the Zetasizer Nano S. Correlation times were based on 10 seconds per run and a total of 10 to 40 runs per measurement were made depending on the nature of the samples. Measurements were repeated up to three times. Calibration was performed with 60 nM calibration latex beads and a 2% bovine serum albumin/PBS solution. Particle size measurement were only tested for peptide solutions with a good apparent solubility. Samples showing the presence of visible insoluble aggregates are indicated as INS. Samples with no measurable particles are indicated as 0 (Zero).

Results

Results of the particle size measurements are presented in table 6. All peptides having a hydrophobicity >75% (peptides 6, 8 and 10) were found to be insoluble in all 5 different aqueous solutions including water, 28 mM L-Histidine and 0.9% NaCl as opposed all other peptides having a degree of hydrophobicity >75%.

Peptides 1-5, 7, 9 and 11-19 had a degree of hydrophobicity <75%, an isoelectric point >5 and an apparent solubility in water, 28 mM L-Histidine and eventually other aqueous solutions with increased higher ionic strength and/or pH.

TABLE 6

| | Water | HIST | NaCl | HIST/NaCl | PBS |
|---|---|---|---|---|---|
| Peptide 6 | INS. | INS. | INS. | INS. | INS. |
| Peptide 8 | INS. | INS. | INS. | INS. | INS. |
| Peptide 10 | INS. | INS. | INS. | INS. | INS. |
| Peptide 11 | 0* | 0* | 0* | INS. | INS. |
| Peptide 9 | 0* | 0* | 6.02* | INS. | INS. |
| Peptide 7 | 0* | 0* | 0* | INS. | INS. |

TABLE 6-continued

|  | Water | HIST | NaCl | HIST/NaCl | PBS |
|---|---|---|---|---|---|
| Peptide 13 | 0* | 0* | 2.2* | 2.7* | 2.3* |
| Peptide 5 | 0* | 0* | 1.6* | 3.3* | 1.35* |
| Peptide 15 | 0* | 0* | 0* | 2.66* | 360.7* |
| Peptide 1 | 0* | 0* | 0* | 0.87* | 2.39* |
| Peptide 14 | 0* | 0* | 0* | 0* | 1.5* |
| Peptide 16' | 0* | 0* | 0* | 2.3* | 2.9* |
| PEG-FIM-01 | 0* | 0* | 0* | 4* | 4* |
| FA-PEG-FIM-01 | 445.3* | 425.8* | 520.1* | INS. | INS. |
| Peptide 16 | 0* | 0* | 0* | 1.83* | 1.4* |
| Peptide 2 | 0* | 0* | 0* | 0* | 4.52* |
| Peptide 3 | 0* | 0* | 0* | 0* | 3.37* |
| Peptide 4 | 0* | 0* | 0* | 0* | 2.38* |
| Peptide 12 | 0* | 0* | 0* | 0* | 1.35* |
| Peptide 17 | 0* | 0* | 0* | 0* | 0* |
| Peptide 18 | 0* | 0* | 0* | 0* | 0* |
| Peptide 19 | 0* | 0* | 0* | 0* | 0* |

INS. = presence of visible insoluble aggregates (not measured);
0 = no detectable particle;
*= apparent solubility As expected, peptide 16, peptide 16' and the immunostimulatory-peptide constructs PEG-FIM-01 and FA-PEG-FIM-01 (either containing peptide 16 or peptide 16') behaved similarly in this particle size assay, showing apparent solubility in water, 28 mM L-Histidine and 0.9% NaCl with the formation of larger particles or insoluble aggregates in 28 mM L-Histidine/NaCl or PBS.

In Example 2 it was demonstrated that PEG-FIM-01 and FA-PEG-FIM-01 exerted biological effects, notably an ability to promote an improved antibody or T cell responses when combined with peptide or recombinant antigen vaccine in the absence of systemic pro-inflammatory response as opposed to a free small immune stimulant. Example 3 implies that immunostimulatory peptide conjugates derived from other tested peptides shown in Table 5 above will have similar biological effects to PEG-FIM-01 derived from peptide 16.

At a pH inferior to their respective pKa, positively charged residues (R, K and H) are hydrophilic and may contribute to peptide solubility depending on their position in the peptide sequence and the contribution of other amino-acids. This Examples shows that the dibasic sequences (RR) present on the N-terminus and the C-terminus side contribute to the solubility of the peptide. For example, the substitution of the arginines (R) on positions 1 and 17 in peptides 11, 13 and 15 by a leucine residue (L), leading to peptides 6, 8 and 10 respectively (see below), makes them become insoluble in water and other aqueous solution with higher pH and ionic strength if the overall hydrophobicity is >75%.

```
Peptide11    RRLLHALLALLAHLLRRL
             -RLLHALLALLAHLLR-L
Peptide6     LRLLHALLALLAHLLRLL Peptide13    RRLLHAALALAAHLLRRL
             -RLLHAALALAAHLLR-L
Peptide8     LRLLHAALALAAHLLRLL Peptide15    RRLLAAHLALHAALLRRL
             -RLLAAHLALHAALLR-L
Peptide10    LRLLAAHLALHAALLRLL
```

The invention claimed is:

1. A method of stimulating an anti-tumor immune response, comprising:
administering an immunostimulatory compound to a subject in need thereof, wherein the immunostimulatory compound comprises (i) an immunostimulant portion covalently coupled to (ii) a peptide portion,
wherein the immunostimulant portion is selected from a Toll-like receptor 7 (TLR7) or TLR8 agonist, or a NOD-like receptor (NLR) agonist (NOD1 or NOD2)

and wherein the immunostimulant portion comprises at least one of an imidazopyridine moiety, an imidazoquinoline moiety, a muramyl dipeptide moiety, a muramyl tripeptide moiety, and a γ-D-glutamyl-meso-diaminopimelic acid moiety; and, wherein the peptide portion is 17 to 45 amino acids in length, and comprises an amino acid sequence of RRLL(5)A(7)LAL(11)A(13)LLRR (SEQ ID NO: 84):

wherein amino acid positions (5), (7), (11) and (13) are each selected from A, L, or H; and, wherein the peptide reduces solubility of the immunostimulant portion after administration to the subject.

2. The method of claim 1, wherein the peptide portion is further covalently coupled to a vector comprising a hydrocarbon, a fluorocarbon or a lipid moiety.

3. The method of claim 1, wherein the immunostimulatory compound is present as a liquid, aerosol, solid, injectable solution, spray, suspension or emulsion.

4. The method of claim 1, wherein administering is via parenteral, subcutaneous, oral, epidermal, intradermal, intramuscular, intraarterial, intraperitoneal, intratumoral, intravesical or intravenous injection; or topically to skin or mucosa.

5. The method of claim 1, wherein the immunostimulant portion has a structure according to any one of Formulae (I), (IIa), (IIb), (IIIa), (IIIb) or (IV):

wherein R1, R4 and R5 are each independently selected from H or C1-C6 branched or unbranched alkyl or alkenyl, or R4 and R5 together with the carbon atoms to which they are attached form a 4-, 5-, 6-, 7- or 8-membered cycloalkyl, cycloalkenyl, or aromatic hydrocarbon ring, with up to two carbon atoms in each of R1, R4, and R5, or R4 and R5 in combination, being replaceable with heteroatoms selected from O, N and S; and the wavy line indicates the point of attachment to the remainder of the compound.

6. The method of claim 1, wherein the immunostimulant portion has a structure according to Formula (VI):

7. The method of claim 1, wherein the peptide portion comprises a sequence having 90% identity to SEQ ID NO. 17, SEQ ID NO. 29, SEQ ID NO. 31 or SEQ ID NO. 32.

8. The method of claim 1, wherein the peptide portion comprises a dibasic sequence of formula RRLL (SEQ ID NO: 85) at one or both of N-terminus or C-terminus of the peptide portion.

9. The method of claim 1, wherein the peptide portion comprises a terminal lysine.

10. The method of claim 1, wherein the immunostimulant portion comprises a compound selected from N-acetylmuramyl-L-alanyl-D-isoglutamine, N-glycolylmuramyl-L-alanyl-D-isoglutamine, N-acetylmuramyl-L-alanyl-D-glutamine n-butyl ester (murabutide), N-acetylmuramyl-L-alanyl-D-isoglutaminyl-L-lysine, N-acetylmuramyl-L-alanyl-γ-D-glutamyl-meso-diaminopimelic acid, N-acetyl-D-glucosaminyl-(β-1,4)-N-acetylmuramyl-L-alanyl-D-isoglutamine, 6-O-stearoyl-N-acetylmuramyl-L-alanyl-D-isoglutamine, mifamurtide, N-acetylmuramyl-L-alanyl-D-isoglutaminyl-L-alanine cholesterol ester, γ-D-glutamyl-meso-diaminopimelic acid, L-alanyl-γ-D-glutamyl-meso-diaminopimelic acid, N-acetylmuramyl-L-alanyl-γ-D-glutamyl-meso-diaminopimelic acid, lauroyl-γ-D-glutamyl-meso-diaminopimelic acid, 6-O-(N-acetylmuramyl-L-alanyl-D-isoglutamine)-yl, N-acetylmuramyl-L-alanyl-D-isoglutaminyl, N-acetylmuramyl-L-alanyl-D-isoglutaminyl-L-alanyl, or 6-O-(N-acetylmuramyl-L-alanyl-D-isoglutaminyl-L-alanine)-yl.

11. A method of stimulating an immune response, comprising: administering intratumorally an immunostimulatory compound to a subject in need thereof, wherein the immunostimulatory compound comprises (i) an immunostimulant portion covalently coupled to (ii) a peptide portion,
wherein the immunostimulant portion is selected from a Toll-like receptor 7 (TLR7) or TLR8 agonist, or a NOD-like receptor (NLR) agonist (NOD1 or NOD2) and wherein the immunostimulant portion comprises at least one of an imidazopyridine moiety, an imidazoquinoline moiety, a muramyl dipeptide moiety, a muramyl tripeptide moiety, and a γ-D-glutamyl-meso-diaminopimelic acid moiety; and,
wherein the peptide portion is 17 to 45 amino acids in length, and comprises an amino acid sequence of RRLL(5)A(7)LAL(11)A(13)LLRR (SEQ ID NO: 84): wherein amino acid positions (5), (7), (11) and (13) are each selected from A, L, or H; and, wherein the peptide reduces solubility of the immunostimulant portion after administration to the subject.

12. The method of claim 11, wherein the peptide portion is further covalently coupled to a vector comprising a hydrocarbon, a fluorocarbon or a lipid moiety.

13. The method of claim 11, wherein the immunostimulatory compound is present as a liquid, injectable solution, suspension or emulsion.

14. The method of claim 11, wherein the immunostimulant portion has a structure according to any one of Formulae (I), (IIa), (IIb), (IIIa), (IIIb) or (IV):

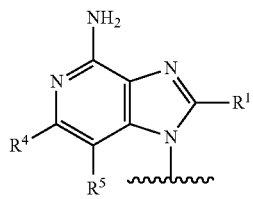
(I)

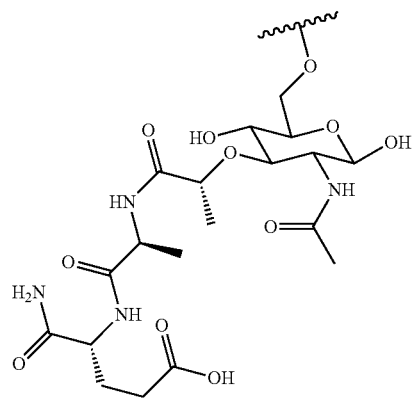
(IIa)

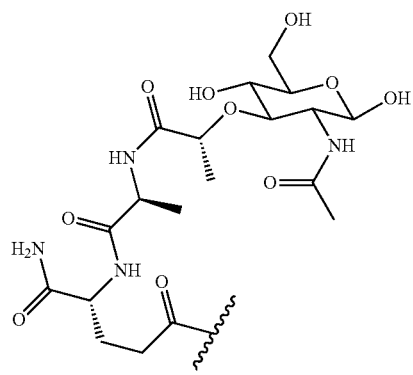
(IIb)

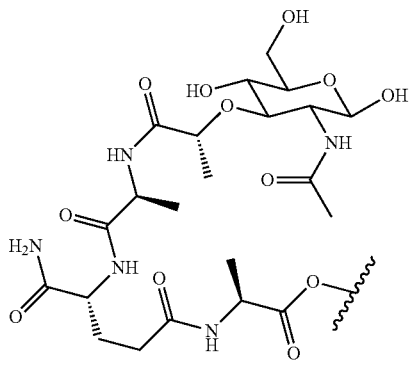
(IIIa)

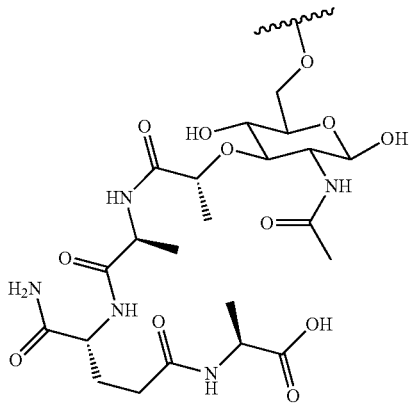
(IIIb)

-continued

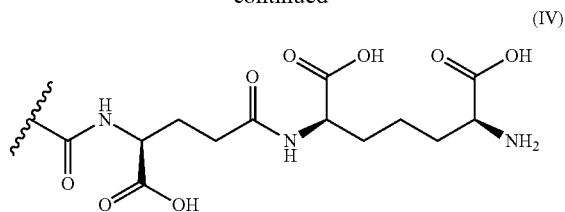
(IV)

wherein R1, R4 and R5 are each independently selected from H or C1-C6 branched or unbranched alkyl or alkenyl, or R4 and R5 together with the carbon atoms to which they are attached form a 4-, 5-, 6-, 7- or 8-membered cycloalkyl, cycloalkenyl, or aromatic hydrocarbon ring, with up to two carbon atoms in each of R1, R4, and R5, or R4 and R5 in combination, being replaceable with heteroatoms selected from O, N and S; and the wavy line indicates the point of attachment to the remainder of the compound.

15. The method of claim 11, wherein the immunostimulant portion has a structure according to Formula (VI):

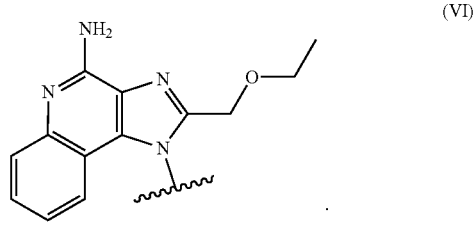 [SMILES: *n1c(COCC)nc2c(N)nc3ccccc3c21]
(VI)

16. The method of claim 11, wherein the peptide portion comprises a sequence having 90% identity to SEQ ID NO. 17, SEQ ID NO. 29, SEQ ID NO. 31 or SEQ ID NO. 32.

17. The method of claim 11, wherein the peptide portion comprises a dibasic sequence of formula RRLL (SEQ ID NO: 85) at one or both of N-terminus or C-terminus of the peptide portion.

18. The method of claim 11, wherein the peptide portion comprises a terminal lysine.

19. The method of claim 11, wherein the immunostimulant portion comprises a compound selected from N-acetylmuramyl-L-alanyl-D-isoglutamine, N-glycolylmuramyl-L-alanyl-D-isoglutamine, N-acetylmuramyl-L-alanyl-D-glutamine n-butyl ester (murabutide), N-acetylmuramyl-L-alanyl-D-isoglutaminyl-L-lysine, N-acetylmuramyl-L-alanyl-γ-D-glutamyl-meso-diaminopimelic acid, N-acetyl-D-glucosaminyl-(β-1,4)-N-acetylmuramyl-L-alanyl-D-isoglutamine, 6-O-stearoyl-N-acetylmuramyl-L-alanyl-D-isoglutamine, mifamurtide, N-acetylmuramyl-L-alanyl-D-isoglutaminyl-L-alanine cholesterol ester, γ-D-glutamyl-meso-diaminopimelic acid, L-alanyl-γ-D-glutamyl-meso-diaminopimelic acid, N-acetylmuramyl-L-alanyl-γ-D-glutamyl-meso-diaminopimelic acid, lauroyl-γ-D-glutamyl-meso-diaminopimelic acid, 6-0-(N-acetylmuramyl-L-alanyl-D-isoglutamine)-yl, N-acetylmuramyl-L-alanyl-D-isoglutaminyl, N-acetylmuramyl-L-alanyl-D-isoglutaminyl-L-alanyl, or 6-O-(N-acetylmuramyl-L-alanyl-D-isoglutaminyl-L-alanine)-yl.

* * * * *

SEQUENCE LISTING

```
<160> NUMBER OF SEQ ID NOS: 85

<210> SEQ ID NO 1
<211> LENGTH: 17
<212> TYPE: PRT
<213> ORGANISM: Artificial Sequence
<220> FEATURE:
<223> OTHER INFORMATION: synthetic peptide

<400> SEQUENCE: 1

Arg Arg Leu Leu Ala His Leu Leu His Leu Leu His Ala Leu Leu Arg
1               5                   10                  15

Arg

<210> SEQ ID NO 2
<211> LENGTH: 17
<212> TYPE: PRT
<213> ORGANISM: Artificial Sequence
<220> FEATURE:
<223> OTHER INFORMATION: synthetic peptide

<400> SEQUENCE: 2

Arg Arg Leu Leu Ala His Leu Leu Ala Leu Leu His Ala Leu Leu Arg
1               5                   10                  15

Arg

<210> SEQ ID NO 3
<211> LENGTH: 17
<212> TYPE: PRT
<213> ORGANISM: Artificial Sequence
<220> FEATURE:
<223> OTHER INFORMATION: synthetic peptide
```

<400> SEQUENCE: 3

Arg Ala Leu Leu Ala His Leu Leu Ala Leu Leu His Ala Leu Leu Ala
1               5                   10                  15

Arg

<210> SEQ ID NO 4
<211> LENGTH: 17
<212> TYPE: PRT
<213> ORGANISM: Artificial Sequence
<220> FEATURE:
<223> OTHER INFORMATION: synthetic peptide

<400> SEQUENCE: 4

Arg Ala Leu Leu Ala His Leu Leu His Leu Leu His Ala Leu Leu Ala
1               5                   10                  15

Arg

<210> SEQ ID NO 5
<211> LENGTH: 17
<212> TYPE: PRT
<213> ORGANISM: Artificial Sequence
<220> FEATURE:
<223> OTHER INFORMATION: synthetic peptide

<400> SEQUENCE: 5

Arg Arg Leu Leu Arg His Leu Leu His Leu Leu His Arg Leu Leu Arg
1               5                   10                  15

Arg

<210> SEQ ID NO 6
<211> LENGTH: 17
<212> TYPE: PRT
<213> ORGANISM: Artificial Sequence
<220> FEATURE:
<223> OTHER INFORMATION: synthetic peptide

<400> SEQUENCE: 6

Arg Arg Leu Leu Arg His Leu Leu Ala Leu Leu His Arg Leu Leu Arg
1               5                   10                  15

Arg

<210> SEQ ID NO 7
<211> LENGTH: 17
<212> TYPE: PRT
<213> ORGANISM: Artificial Sequence
<220> FEATURE:
<223> OTHER INFORMATION: synthetic peptide

<400> SEQUENCE: 7

Arg His Leu Leu Ala His Leu Leu Ala Leu Leu His Ala Leu Leu His
1               5                   10                  15

Arg

<210> SEQ ID NO 8
<211> LENGTH: 17
<212> TYPE: PRT
<213> ORGANISM: Artificial Sequence
<220> FEATURE:
<223> OTHER INFORMATION: synthetic peptide

<400> SEQUENCE: 8

Arg His Leu Leu Ala His Leu Leu His Leu Leu His Ala Leu Leu His

```
1               5                   10                  15
Arg

<210> SEQ ID NO 9
<211> LENGTH: 17
<212> TYPE: PRT
<213> ORGANISM: Artificial Sequence
<220> FEATURE:
<223> OTHER INFORMATION: synthetic peptide

<400> SEQUENCE: 9

Ala His Leu Leu Ala His Leu Leu His Leu Leu His Ala Leu Leu His
1               5                   10                  15
Ala

<210> SEQ ID NO 10
<211> LENGTH: 17
<212> TYPE: PRT
<213> ORGANISM: Artificial Sequence
<220> FEATURE:
<223> OTHER INFORMATION: synthetic peptide

<400> SEQUENCE: 10

Ala His Leu Leu Ala His Leu Leu Ala Leu Leu His Ala Leu Leu His
1               5                   10                  15
Ala

<210> SEQ ID NO 11
<211> LENGTH: 17
<212> TYPE: PRT
<213> ORGANISM: Artificial Sequence
<220> FEATURE:
<223> OTHER INFORMATION: synthetic peptide

<400> SEQUENCE: 11

Ala His Leu Leu Ala His Leu Leu Arg Leu Leu His Ala Leu Leu His
1               5                   10                  15
Ala

<210> SEQ ID NO 12
<211> LENGTH: 17
<212> TYPE: PRT
<213> ORGANISM: Artificial Sequence
<220> FEATURE:
<223> OTHER INFORMATION: synthetic peptide

<400> SEQUENCE: 12

Arg Arg Leu Leu Arg Arg Leu Leu Arg Leu Leu Arg Arg Leu Leu Arg
1               5                   10                  15
Arg

<210> SEQ ID NO 13
<211> LENGTH: 17
<212> TYPE: PRT
<213> ORGANISM: Artificial Sequence
<220> FEATURE:
<223> OTHER INFORMATION: synthetic peptide

<400> SEQUENCE: 13

Lys Lys Leu Leu Lys Lys Leu Leu Lys Leu Leu Lys Lys Leu Leu Lys
1               5                   10                  15
Lys
```

<210> SEQ ID NO 14
<211> LENGTH: 17
<212> TYPE: PRT
<213> ORGANISM: Artificial Sequence
<220> FEATURE:
<223> OTHER INFORMATION: synthetic peptide

<400> SEQUENCE: 14

Arg Arg Leu Leu Arg Arg Leu Leu Ala Leu Leu Arg Arg Leu Leu Arg
1               5                   10                  15

Arg

<210> SEQ ID NO 15
<211> LENGTH: 17
<212> TYPE: PRT
<213> ORGANISM: Artificial Sequence
<220> FEATURE:
<223> OTHER INFORMATION: synthetic peptide

<400> SEQUENCE: 15

Arg Arg Leu Leu Ala Arg Leu Leu Ala Leu Leu Arg Ala Leu Leu Arg
1               5                   10                  15

Arg

<210> SEQ ID NO 16
<211> LENGTH: 17
<212> TYPE: PRT
<213> ORGANISM: Artificial Sequence
<220> FEATURE:
<223> OTHER INFORMATION: synthetic peptide

<400> SEQUENCE: 16

Arg Arg Leu Leu Arg Ala Leu Leu Ala Leu Leu Ala Arg Leu Leu Arg
1               5                   10                  15

Arg

<210> SEQ ID NO 17
<211> LENGTH: 17
<212> TYPE: PRT
<213> ORGANISM: Artificial Sequence
<220> FEATURE:
<223> OTHER INFORMATION: synthetic peptide

<400> SEQUENCE: 17

Arg Arg Leu Leu His Ala Leu Leu Ala Leu Leu Ala His Leu Leu Arg
1               5                   10                  15

Arg

<210> SEQ ID NO 18
<211> LENGTH: 17
<212> TYPE: PRT
<213> ORGANISM: Artificial Sequence
<220> FEATURE:
<223> OTHER INFORMATION: synthetic peptide

<400> SEQUENCE: 18

Arg Arg Leu Leu Pro Ala Pro Leu Ala Leu Pro Ala Pro Leu Leu Arg
1               5                   10                  15

Arg

<210> SEQ ID NO 19
<211> LENGTH: 17
<212> TYPE: PRT

```
<213> ORGANISM: Artificial Sequence
<220> FEATURE:
<223> OTHER INFORMATION: synthetic peptide

<400> SEQUENCE: 19

Arg Arg Leu Leu Pro Ala Ala Leu Ala Leu Ala Ala Pro Leu Leu Arg
1               5                   10                  15

Arg

<210> SEQ ID NO 20
<211> LENGTH: 17
<212> TYPE: PRT
<213> ORGANISM: Artificial Sequence
<220> FEATURE:
<223> OTHER INFORMATION: synthetic peptide

<400> SEQUENCE: 20

Arg Arg Leu Leu Pro Ala Leu Ala Leu Leu Ala Pro Leu Leu Arg
1               5                   10                  15

Arg

<210> SEQ ID NO 21
<211> LENGTH: 17
<212> TYPE: PRT
<213> ORGANISM: Artificial Sequence
<220> FEATURE:
<223> OTHER INFORMATION: synthetic peptide

<400> SEQUENCE: 21

Arg Arg Leu Leu Leu Ala Pro Leu Ala Leu Pro Ala Leu Leu Leu Arg
1               5                   10                  15

Arg

<210> SEQ ID NO 22
<211> LENGTH: 17
<212> TYPE: PRT
<213> ORGANISM: Artificial Sequence
<220> FEATURE:
<223> OTHER INFORMATION: synthetic peptide

<400> SEQUENCE: 22

Arg Arg Leu Leu Ala Ala Pro Leu Ala Leu Pro Ala Ala Leu Leu Arg
1               5                   10                  15

Arg

<210> SEQ ID NO 23
<211> LENGTH: 17
<212> TYPE: PRT
<213> ORGANISM: Artificial Sequence
<220> FEATURE:
<223> OTHER INFORMATION: synthetic peptide

<400> SEQUENCE: 23

Leu Arg Leu Leu His Ala Leu Leu Ala Leu Leu Ala His Leu Leu Arg
1               5                   10                  15

Leu

<210> SEQ ID NO 24
<211> LENGTH: 17
<212> TYPE: PRT
<213> ORGANISM: Artificial Sequence
<220> FEATURE:
<223> OTHER INFORMATION: synthetic peptide
```

```
<400> SEQUENCE: 24

Leu Arg Leu Leu His Ala Pro Leu Ala Leu Pro Ala His Leu Leu Arg
1               5                   10                  15

Leu

<210> SEQ ID NO 25
<211> LENGTH: 17
<212> TYPE: PRT
<213> ORGANISM: Artificial Sequence
<220> FEATURE:
<223> OTHER INFORMATION: synthetic peptide

<400> SEQUENCE: 25

Leu Arg Leu Leu His Ala Ala Leu Ala Leu Ala Ala His Leu Leu Arg
1               5                   10                  15

Leu

<210> SEQ ID NO 26
<211> LENGTH: 17
<212> TYPE: PRT
<213> ORGANISM: Artificial Sequence
<220> FEATURE:
<223> OTHER INFORMATION: synthetic peptide

<400> SEQUENCE: 26

Leu Arg Leu Leu Pro Ala His Leu Ala Leu His Ala Pro Leu Leu Arg
1               5                   10                  15

Leu

<210> SEQ ID NO 27
<211> LENGTH: 17
<212> TYPE: PRT
<213> ORGANISM: Artificial Sequence
<220> FEATURE:
<223> OTHER INFORMATION: synthetic peptide

<400> SEQUENCE: 27

Leu Arg Leu Leu Ala Ala His Leu Ala Leu His Ala Ala Leu Leu Arg
1               5                   10                  15

Leu

<210> SEQ ID NO 28
<211> LENGTH: 17
<212> TYPE: PRT
<213> ORGANISM: Artificial Sequence
<220> FEATURE:
<223> OTHER INFORMATION: synthetic peptide

<400> SEQUENCE: 28

Arg Arg Leu Leu His Ala Pro Leu Ala Leu Pro Ala His Leu Leu Arg
1               5                   10                  15

Arg

<210> SEQ ID NO 29
<211> LENGTH: 17
<212> TYPE: PRT
<213> ORGANISM: Artificial Sequence
<220> FEATURE:
<223> OTHER INFORMATION: synthetic peptide

<400> SEQUENCE: 29

Arg Arg Leu Leu His Ala Ala Leu Ala Leu Ala Ala His Leu Leu Arg
1               5                   10                  15
```

Arg

<210> SEQ ID NO 30
<211> LENGTH: 17
<212> TYPE: PRT
<213> ORGANISM: Artificial Sequence
<220> FEATURE:
<223> OTHER INFORMATION: synthetic peptide

<400> SEQUENCE: 30

Arg Arg Leu Leu Pro Ala His Leu Ala Leu His Ala Pro Leu Leu Arg
1               5                   10                  15

Arg

<210> SEQ ID NO 31
<211> LENGTH: 17
<212> TYPE: PRT
<213> ORGANISM: Artificial Sequence
<220> FEATURE:
<223> OTHER INFORMATION: synthetic peptide

<400> SEQUENCE: 31

Arg Arg Leu Leu Ala Ala His Leu Ala Leu His Ala Ala Leu Leu Arg
1               5                   10                  15

Arg

<210> SEQ ID NO 32
<211> LENGTH: 17
<212> TYPE: PRT
<213> ORGANISM: Artificial Sequence
<220> FEATURE:
<223> OTHER INFORMATION: synthetic peptide

<400> SEQUENCE: 32

Arg Arg Leu Leu His Ala His Leu Ala Leu His Ala His Leu Leu Arg
1               5                   10                  15

Arg

<210> SEQ ID NO 33
<211> LENGTH: 17
<212> TYPE: PRT
<213> ORGANISM: Artificial Sequence
<220> FEATURE:
<223> OTHER INFORMATION: synthetic peptide

<400> SEQUENCE: 33

Arg Arg Leu Leu His Ala Lys Leu Ala Leu Lys Ala His Leu Leu Arg
1               5                   10                  15

Arg

<210> SEQ ID NO 34
<211> LENGTH: 17
<212> TYPE: PRT
<213> ORGANISM: Artificial Sequence
<220> FEATURE:
<223> OTHER INFORMATION: synthetic peptide

<400> SEQUENCE: 34

Arg Arg Leu Leu Lys Ala Lys Leu Ala Leu Lys Ala Lys Leu Leu Arg
1               5                   10                  15

Arg

```
<210> SEQ ID NO 35
<211> LENGTH: 17
<212> TYPE: PRT
<213> ORGANISM: Artificial Sequence
<220> FEATURE:
<223> OTHER INFORMATION: synthetic peptide

<400> SEQUENCE: 35

Arg Arg Leu Lys Lys Ala Lys Leu Lys Leu Lys Ala Lys Lys Leu Arg
1               5                   10                  15

Arg

<210> SEQ ID NO 36
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(2)
<223> OTHER INFORMATION: X = [K, R, H, Q, OR A]
<220> FEATURE:
<221> NAME/KEY: MISC_FEATURE
<222> LOCATION: (3)..(4)
<223> OTHER INFORMATION: X = [L, H, Q, OR A]
<220> FEATURE:
<221> NAME/KEY: MISC_FEATURE
<222> LOCATION: (5)..(6)
<223> OTHER INFORMATION: X = [K, R, H, Q, A, OR L]
<220> FEATURE:
<221> NAME/KEY: MISC_FEATURE
<222> LOCATION: (7)..(8)
<223> OTHER INFORMATION: X = [L, H, Q, A, OR W]
<220> FEATURE:
<221> NAME/KEY: MISC_FEATURE
<222> LOCATION: (9)..(9)
<223> OTHER INFORMATION: X = [K, R, H, Q, A, OR L]
<220> FEATURE:
<221> NAME/KEY: MISC_FEATURE
<222> LOCATION: (10)..(11)
<223> OTHER INFORMATION: X = [L, H, Q, A, OR W]
<220> FEATURE:
<221> NAME/KEY: MISC_FEATURE
<222> LOCATION: (12)..(13)
<223> OTHER INFORMATION: X = [K, R, H, Q, A, OR L]
<220> FEATURE:
<221> NAME/KEY: MISC_FEATURE
<222> LOCATION: (14)..(15)
<223> OTHER INFORMATION: X = [L, H, Q, OR A]
<220> FEATURE:
<221> NAME/KEY: MISC_FEATURE
<222> LOCATION: (16)..(17)
<223> OTHER INFORMATION: X = [K, R, H, Q, OR A]

<400> SEQUENCE: 36

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 37
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X = [R, K, H, OR L]
<220> FEATURE:
<221> NAME/KEY: MISC_FEATURE
<222> LOCATION: (2)..(2)
```

```
<223> OTHER INFORMATION: X = [R, K, OR H]
<220> FEATURE:
<221> NAME/KEY: MISC_FEATURE
<222> LOCATION: (5)..(5)
<223> OTHER INFORMATION: X = [H, K, R, L, A, OR P]
<220> FEATURE:
<221> NAME/KEY: MISC_FEATURE
<222> LOCATION: (7)..(7)
<223> OTHER INFORMATION: X = [H, K, R, L, A, OR P]
<220> FEATURE:
<221> NAME/KEY: MISC_FEATURE
<222> LOCATION: (9)..(9)
<223> OTHER INFORMATION: X = [A, K, R, OR H]
<220> FEATURE:
<221> NAME/KEY: MISC_FEATURE
<222> LOCATION: (11)..(11)
<223> OTHER INFORMATION: X = [H, K, R, L, A, OR P]
<220> FEATURE:
<221> NAME/KEY: MISC_FEATURE
<222> LOCATION: (13)..(13)
<223> OTHER INFORMATION: X = [H, K, R, L, A, OR P]
<220> FEATURE:
<221> NAME/KEY: MISC_FEATURE
<222> LOCATION: (16)..(16)
<223> OTHER INFORMATION: X = [R, K, OR H]
<220> FEATURE:
<221> NAME/KEY: MISC_FEATURE
<222> LOCATION: (17)..(17)
<223> OTHER INFORMATION: X = [R, K, H, OR L]

<400> SEQUENCE: 37

Xaa Xaa Leu Leu Xaa Ala Xaa Leu Xaa Leu Xaa Ala Xaa Leu Leu Xaa
1               5                   10                  15

Xaa

<210> SEQ ID NO 38
<211> LENGTH: 20
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEG-FIM-01
<220> FEATURE:
<221> NAME/KEY: MISC_FEATURE
<222> LOCATION: (1)..(1)
<223> OTHER INFORMATION: CH3CO-
<220> FEATURE:
<221> NAME/KEY: MISC_FEATURE
<222> LOCATION: (20)..(20)
<223> OTHER INFORMATION: PEG-FIM

<400> SEQUENCE: 38

Lys Arg Arg Leu Leu His Ala His Leu Ala Leu His Ala His Leu Leu
1               5                   10                  15

Arg Arg Leu Lys
            20

<210> SEQ ID NO 39
<211> LENGTH: 18
<212> TYPE: PRT
<213> ORGANISM: Artificial Sequence
<220> FEATURE:
<223> OTHER INFORMATION: synthetic peptide

<400> SEQUENCE: 39

Arg Arg Leu Leu His Ala His Leu Ala Leu His Ala His Leu Leu Arg
1               5                   10                  15

Arg Leu
```

<210> SEQ ID NO 40
<211> LENGTH: 20
<212> TYPE: PRT
<213> ORGANISM: Artificial Sequence
<220> FEATURE:
<223> OTHER INFORMATION: synthetic peptide
<220> FEATURE:
<223> OTHER INFORMATION: FA-PEG-FIM-01
<220> FEATURE:
<221> NAME/KEY: MISC_FEATURE
<222> LOCATION: (1)..(1)
<223> OTHER INFORMATION: C8F17(CH2)2CO-
<220> FEATURE:
<221> NAME/KEY: MISC_FEATURE
<222> LOCATION: (20)..(20)
<223> OTHER INFORMATION: PEG-FIM

<400> SEQUENCE: 40

Lys Arg Arg Leu Leu His Ala His Leu Ala Leu His Ala His Leu Leu
1               5                   10                  15

Arg Arg Leu Lys
            20

<210> SEQ ID NO 41
<211> LENGTH: 20
<212> TYPE: PRT
<213> ORGANISM: Artificial Sequence
<220> FEATURE:
<223> OTHER INFORMATION: synthetic peptide
<220> FEATURE:
<223> OTHER INFORMATION: FA-FIM-01
<220> FEATURE:
<221> NAME/KEY: MISC_FEATURE
<222> LOCATION: (1)..(1)
<223> OTHER INFORMATION: C8F17(CH2)2CO-
<220> FEATURE:
<221> NAME/KEY: MISC_FEATURE
<222> LOCATION: (20)..(20)
<223> OTHER INFORMATION: FIM

<400> SEQUENCE: 41

Lys Arg Arg Leu Leu His Ala His Leu Ala Leu His Ala His Leu Leu
1               5                   10                  15

Arg Arg Leu Lys
            20

<210> SEQ ID NO 42
<211> LENGTH: 36
<212> TYPE: PRT
<213> ORGANISM: Artificial Sequence
<220> FEATURE:
<223> OTHER INFORMATION: synthetic polypeptide
<220> FEATURE:
<223> OTHER INFORMATION: FA-P113
<220> FEATURE:
<221> NAME/KEY: MISC_FEATURE
<222> LOCATION: (1)..(1)
<223> OTHER INFORMATION: FA1
<220> FEATURE:
<221> NAME/KEY: MISC_FEATURE
<222> LOCATION: (36)..(36)
<223> OTHER INFORMATION: CONH2

<400> SEQUENCE: 42

Lys Val Gly Pro Leu Thr Val Asn Glu Lys Arg Arg Leu Lys Leu Ile
1               5                   10                  15

Met Pro Ala Arg Phe Tyr Pro Asn Val Thr Lys Tyr Leu Pro Leu Asp
            20                  25                  30

Lys Gly Ile Lys
        35

<210> SEQ ID NO 43
<211> LENGTH: 36
<212> TYPE: PRT
<213> ORGANISM: Artificial Sequence
<220> FEATURE:
<223> OTHER INFORMATION: synthetic polypeptide
<220> FEATURE:
<223> OTHER INFORMATION: FA-P151
<220> FEATURE:
<221> NAME/KEY: MISC_FEATURE
<222> LOCATION: (1)..(1)
<223> OTHER INFORMATION: FA1
<220> FEATURE:
<221> NAME/KEY: MISC_FEATURE
<222> LOCATION: (36)..(36)
<223> OTHER INFORMATION: CONH2

<400> SEQUENCE: 43

Lys Pro Glu His Val Val Asn His Tyr Phe Gln Thr Arg His Tyr Leu
1               5                   10                  15

His Thr Leu Trp Lys Ala Gly Ile Leu Tyr Lys Arg Glu Thr Thr Arg
            20                  25                  30

Ser Ala Ser Phe
        35

<210> SEQ ID NO 44
<211> LENGTH: 40
<212> TYPE: PRT
<213> ORGANISM: Artificial Sequence
<220> FEATURE:
<223> OTHER INFORMATION: synthetic polypeptide
<220> FEATURE:
<223> OTHER INFORMATION: FA-P277(K)
<220> FEATURE:
<221> NAME/KEY: MISC_FEATURE
<222> LOCATION: (1)..(1)
<223> OTHER INFORMATION: FA1
<220> FEATURE:
<221> NAME/KEY: MISC_FEATURE
<222> LOCATION: (40)..(40)
<223> OTHER INFORMATION: CONH2

<400> SEQUENCE: 44

Lys Arg Val Ser Trp Pro Lys Phe Ala Val Pro Asn Leu Gln Ser Leu
1               5                   10                  15

Thr Asn Leu Leu Ser Ser Asn Leu Ser Trp Leu Ser Leu Asp Val Ser
            20                  25                  30

Ala Ala Phe Tyr His Lys Lys Lys
        35                  40

<210> SEQ ID NO 45
<211> LENGTH: 41
<212> TYPE: PRT
<213> ORGANISM: Artificial Sequence
<220> FEATURE:
<223> OTHER INFORMATION: synthetic polypeptide
<220> FEATURE:
<223> OTHER INFORMATION: FA-P376
<220> FEATURE:
<221> NAME/KEY: MISC_FEATURE
<222> LOCATION: (1)..(1)
<223> OTHER INFORMATION: FA1
<220> FEATURE:
<221> NAME/KEY: MISC_FEATURE
<222> LOCATION: (41)..(41)
<223> OTHER INFORMATION: CONH2

<400> SEQUENCE: 45

Lys Lys Leu His Leu Tyr Ser His Pro Ile Leu Gly Phe Arg Lys
1               5                   10                  15

Ile Pro Met Gly Val Gly Leu Ser Pro Phe Leu Leu Ala Gln Phe Thr
            20                  25                  30

Ser Ala Ile Ser Ser Val Val Arg Arg
        35                  40

<210> SEQ ID NO 46
<211> LENGTH: 39
<212> TYPE: PRT
<213> ORGANISM: Artificial Sequence
<220> FEATURE:
<223> OTHER INFORMATION: synthetic polypeptide
<220> FEATURE:
<223> OTHER INFORMATION: FA-P753(K)
<220> FEATURE:
<221> NAME/KEY: MISC_FEATURE
<222> LOCATION: (1)..(1)
<223> OTHER INFORMATION: FA1
<220> FEATURE:
<221> NAME/KEY: MISC_FEATURE
<222> LOCATION: (39)..(39)
<223> OTHER INFORMATION: CONH2

<400> SEQUENCE: 46

Lys Lys Lys Lys Glu Phe Gly Ala Thr Val Glu Leu Leu Ser Phe Leu
1               5                   10                  15

Pro Ser Asp Phe Phe Pro Ser Val Arg Asp Leu Leu Asp Thr Ala Ser
            20                  25                  30

Ala Leu Tyr Arg Lys Lys Lys
        35

<210> SEQ ID NO 47
<211> LENGTH: 39
<212> TYPE: PRT
<213> ORGANISM: Artificial Sequence
<220> FEATURE:
<223> OTHER INFORMATION: synthetic polypeptide
<220> FEATURE:
<223> OTHER INFORMATION: FA-P797(K)
<220> FEATURE:
<221> NAME/KEY: MISC_FEATURE
<222> LOCATION: (1)..(1)
<223> OTHER INFORMATION: FA1
<220> FEATURE:
<221> NAME/KEY: MISC_FEATURE
<222> LOCATION: (39)..(39)
<223> OTHER INFORMATION: CONH2

<400> SEQUENCE: 47

Lys Ser Pro His His Thr Ala Leu Arg Gln Ala Ile Leu Ser Trp Gly
1               5                   10                  15

Glu Leu Met Thr Leu Ala Thr Trp Val Gly Ser Asn Leu Glu Asp Pro
            20                  25                  30

Ala Ser Arg Asp Lys Lys Lys
        35

<210> SEQ ID NO 48
<211> LENGTH: 39
<212> TYPE: PRT
<213> ORGANISM: Artificial Sequence
<220> FEATURE:
<223> OTHER INFORMATION: synthetic polypeptide
<220> FEATURE:
<223> OTHER INFORMATION: FA-P856(K)
<220> FEATURE:
<221> NAME/KEY: MISC_FEATURE
<222> LOCATION: (1)..(1)

<223> OTHER INFORMATION: FA1
<220> FEATURE:
<221> NAME/KEY: MISC_FEATURE
<222> LOCATION: (39)..(39)
<223> OTHER INFORMATION: CONH2

<400> SEQUENCE: 48

Lys Leu Thr Phe Gly Arg Glu Thr Val Leu Glu Tyr Leu Val Ser Phe
1               5                   10                  15

Gly Val Trp Ile Arg Thr Pro Pro Ala Tyr Arg Pro Pro Asn Ala Pro
            20                  25                  30

Ile Leu Ser Thr Lys Lys Lys
        35

<210> SEQ ID NO 49
<211> LENGTH: 32
<212> TYPE: PRT
<213> ORGANISM: Artificial Sequence
<220> FEATURE:
<223> OTHER INFORMATION: synthetic polypeptide
<220> FEATURE:
<223> OTHER INFORMATION: FA-P877
<220> FEATURE:
<221> NAME/KEY: MISC_FEATURE
<222> LOCATION: (1)..(1)
<223> OTHER INFORMATION: FA1
<220> FEATURE:
<221> NAME/KEY: MISC_FEATURE
<222> LOCATION: (32)..(32)
<223> OTHER INFORMATION: CONH2

<400> SEQUENCE: 49

Lys Pro Pro Ala Tyr Arg Pro Pro Asn Ala Pro Ile Leu Ser Thr Leu
1               5                   10                  15

Pro Glu Thr Thr Val Val Arg Arg Arg Gly Arg Ser Pro Arg Arg Arg
            20                  25                  30

<210> SEQ ID NO 50
<211> LENGTH: 40
<212> TYPE: PRT
<213> ORGANISM: Artificial Sequence
<220> FEATURE:
<223> OTHER INFORMATION: synthetic polypeptide
<220> FEATURE:
<223> OTHER INFORMATION: FA-P1266(K)
<220> FEATURE:
<221> NAME/KEY: MISC_FEATURE
<222> LOCATION: (1)..(1)
<223> OTHER INFORMATION: FA1
<220> FEATURE:
<221> NAME/KEY: MISC_FEATURE
<222> LOCATION: (40)..(40)
<223> OTHER INFORMATION: CONH2

<400> SEQUENCE: 50

Lys Lys Lys Lys Gly Pro Leu Leu Val Leu Gln Ala Gly Phe Phe Leu
1               5                   10                  15

Leu Thr Arg Ile Leu Thr Ile Pro Gln Ser Leu Asp Ser Trp Trp Thr
            20                  25                  30

Ser Leu Asn Phe Leu Lys Lys Lys
        35                  40

<210> SEQ ID NO 51
<211> LENGTH: 35
<212> TYPE: PRT
<213> ORGANISM: Artificial Sequence
<220> FEATURE:
<223> OTHER INFORMATION: synthetic polypeptide

<220> FEATURE:
<223> OTHER INFORMATION: P113

<400> SEQUENCE: 51

Val Gly Pro Leu Thr Val Asn Glu Lys Arg Arg Leu Lys Leu Ile Met
1               5                   10                  15

Pro Ala Arg Phe Tyr Pro Asn Val Thr Lys Tyr Leu Pro Leu Asp Lys
            20                  25                  30

Gly Ile Lys
        35

<210> SEQ ID NO 52
<211> LENGTH: 35
<212> TYPE: PRT
<213> ORGANISM: Artificial Sequence
<220> FEATURE:
<223> OTHER INFORMATION: synthetic polypeptide
<220> FEATURE:
<223> OTHER INFORMATION: P151

<400> SEQUENCE: 52

Pro Glu His Val Val Asn His Tyr Phe Gln Thr Arg His Tyr Leu His
1               5                   10                  15

Thr Leu Trp Lys Ala Gly Ile Leu Tyr Lys Arg Glu Thr Thr Arg Ser
            20                  25                  30

Ala Ser Phe
        35

<210> SEQ ID NO 53
<211> LENGTH: 39
<212> TYPE: PRT
<213> ORGANISM: Artificial Sequence
<220> FEATURE:
<223> OTHER INFORMATION: synthetic polypeptide
<220> FEATURE:
<223> OTHER INFORMATION: P277(K)

<400> SEQUENCE: 53

Arg Val Ser Trp Pro Lys Phe Ala Val Pro Asn Leu Gln Ser Leu Thr
1               5                   10                  15

Asn Leu Leu Ser Ser Asn Leu Ser Trp Leu Ser Leu Asp Val Ser Ala
            20                  25                  30

Ala Phe Tyr His Lys Lys Lys
        35

<210> SEQ ID NO 54
<211> LENGTH: 40
<212> TYPE: PRT
<213> ORGANISM: Artificial Sequence
<220> FEATURE:
<223> OTHER INFORMATION: synthetic polypeptide
<220> FEATURE:
<223> OTHER INFORMATION: P376

<400> SEQUENCE: 54

Lys Leu His Leu Tyr Ser His Pro Ile Ile Leu Gly Phe Arg Lys Ile
1               5                   10                  15

Pro Met Gly Val Gly Leu Ser Pro Phe Leu Leu Ala Gln Phe Thr Ser
            20                  25                  30

Ala Ile Ser Ser Val Val Arg Arg
        35                  40

<210> SEQ ID NO 55

```
<211> LENGTH: 38
<212> TYPE: PRT
<213> ORGANISM: Artificial Sequence
<220> FEATURE:
<223> OTHER INFORMATION: synthetic polypeptide
<220> FEATURE:
<223> OTHER INFORMATION: P753(K)

<400> SEQUENCE: 55

Lys Lys Lys Glu Phe Gly Ala Thr Val Glu Leu Leu Ser Phe Leu Pro
1               5                   10                  15

Ser Asp Phe Phe Pro Ser Val Arg Asp Leu Leu Asp Thr Ala Ser Ala
            20                  25                  30

Leu Tyr Arg Lys Lys Lys
        35

<210> SEQ ID NO 56
<211> LENGTH: 38
<212> TYPE: PRT
<213> ORGANISM: Artificial Sequence
<220> FEATURE:
<223> OTHER INFORMATION: synthetic polypeptide
<220> FEATURE:
<223> OTHER INFORMATION: P797(K)

<400> SEQUENCE: 56

Ser Pro His His Thr Ala Leu Arg Gln Ala Ile Leu Ser Trp Gly Glu
1               5                   10                  15

Leu Met Thr Leu Ala Thr Trp Val Gly Ser Asn Leu Glu Asp Pro Ala
            20                  25                  30

Ser Arg Asp Lys Lys Lys
        35

<210> SEQ ID NO 57
<211> LENGTH: 38
<212> TYPE: PRT
<213> ORGANISM: Artificial Sequence
<220> FEATURE:
<223> OTHER INFORMATION: synthetic polypeptide
<220> FEATURE:
<223> OTHER INFORMATION: P856(K)

<400> SEQUENCE: 57

Leu Thr Phe Gly Arg Glu Thr Val Leu Glu Tyr Leu Val Ser Phe Gly
1               5                   10                  15

Val Trp Ile Arg Thr Pro Pro Ala Tyr Arg Pro Pro Asn Ala Pro Ile
            20                  25                  30

Leu Ser Thr Lys Lys Lys
        35

<210> SEQ ID NO 58
<211> LENGTH: 31
<212> TYPE: PRT
<213> ORGANISM: Artificial Sequence
<220> FEATURE:
<223> OTHER INFORMATION: synthetic polypeptide
<220> FEATURE:
<223> OTHER INFORMATION: P877

<400> SEQUENCE: 58

Pro Pro Ala Tyr Arg Pro Pro Asn Ala Pro Ile Leu Ser Thr Leu Pro
1               5                   10                  15

Glu Thr Thr Val Val Arg Arg Arg Gly Arg Ser Pro Arg Arg
            20                  25                  30
```

```
<210> SEQ ID NO 59
<211> LENGTH: 36
<212> TYPE: PRT
<213> ORGANISM: Artificial Sequence
<220> FEATURE:
<223> OTHER INFORMATION: Synthetic polypeptide
<220> FEATURE:
<223> OTHER INFORMATION: P1266(K)

<400> SEQUENCE: 59

Gly Pro Leu Leu Val Leu Gln Ala Gly Phe Phe Leu Leu Thr Arg Ile
1               5                   10                  15

Leu Thr Ile Pro Gln Ser Leu Asp Ser Trp Trp Thr Ser Leu Asn Phe
            20                  25                  30

Leu Lys Lys Lys
        35

<210> SEQ ID NO 60
<211> LENGTH: 9
<212> TYPE: PRT
<213> ORGANISM: Artificial Sequence
<220> FEATURE:
<223> OTHER INFORMATION: synthetic peptide
<220> FEATURE:
<223> OTHER INFORMATION: CTL epitope 151

<400> SEQUENCE: 60

His Tyr Phe Gln Thr Arg His Tyr Leu
1               5

<210> SEQ ID NO 61
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 1
<220> FEATURE:
<221> NAME/KEY: MISC_FEATURE
<222> LOCATION: (1)..(1)
<223> OTHER INFORMATION: CH3CO

<400> SEQUENCE: 61

Arg Arg Leu Leu Pro Ala Pro Leu Ala Leu Pro Ala Pro Leu Leu Arg
1               5                   10                  15

Arg Leu

<210> SEQ ID NO 62
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 2
<220> FEATURE:
<221> NAME/KEY: MISC_FEATURE
<222> LOCATION: (1)..(1)
<223> OTHER INFORMATION: CH3CO

<400> SEQUENCE: 62

Arg Arg Leu Leu Pro Ala Ala Leu Ala Leu Ala Ala Pro Leu Leu Arg
1               5                   10                  15

Arg Leu
```

-continued

```
<210> SEQ ID NO 63
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 3
<220> FEATURE:
<221> NAME/KEY: MISC_FEATURE
<222> LOCATION: (1)..(1)
<223> OTHER INFORMATION: CH3CO

<400> SEQUENCE: 63

Arg Arg Leu Leu Pro Ala Leu Leu Ala Leu Leu Ala Pro Leu Leu Arg
1               5                   10                  15

Arg Leu

<210> SEQ ID NO 64
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 4
<220> FEATURE:
<221> NAME/KEY: MISC_FEATURE
<222> LOCATION: (1)..(1)
<223> OTHER INFORMATION: CH3CO

<400> SEQUENCE: 64

Arg Arg Leu Leu Leu Ala Pro Leu Ala Leu Pro Ala Leu Leu Leu Arg
1               5                   10                  15

Arg Leu

<210> SEQ ID NO 65
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 5
<220> FEATURE:
<221> NAME/KEY: MISC_FEATURE
<222> LOCATION: (1)..(1)
<223> OTHER INFORMATION: CH3CO

<400> SEQUENCE: 65

Arg Arg Leu Leu Ala Ala Pro Leu Ala Leu Pro Ala Ala Leu Leu Arg
1               5                   10                  15

Arg Leu

<210> SEQ ID NO 66
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 6
<220> FEATURE:
<221> NAME/KEY: MISC_FEATURE
<222> LOCATION: (1)..(1)
<223> OTHER INFORMATION: CH3CO

<400> SEQUENCE: 66

Leu Arg Leu Leu His Ala Leu Leu Ala Leu Leu Ala His Leu Leu Arg
```

```
<210> SEQ ID NO 67
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 7
<220> FEATURE:
<221> NAME/KEY: MISC_FEATURE
<222> LOCATION: (1)..(1)
<223> OTHER INFORMATION: CH3CO

<400> SEQUENCE: 67

Leu Arg Leu Leu His Ala Pro Leu Ala Leu Pro Ala His Leu Leu Arg
1               5                   10                  15

Leu Leu

<210> SEQ ID NO 68
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 8
<220> FEATURE:
<221> NAME/KEY: MISC_FEATURE
<222> LOCATION: (1)..(1)
<223> OTHER INFORMATION: CH3CO

<400> SEQUENCE: 68

Leu Arg Leu Leu His Ala Ala Leu Ala Leu Ala Ala His Leu Leu Arg
1               5                   10                  15

Leu Leu

<210> SEQ ID NO 69
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 9
<220> FEATURE:
<221> NAME/KEY: MISC_FEATURE
<222> LOCATION: (1)..(1)
<223> OTHER INFORMATION: CH3CO

<400> SEQUENCE: 69

Leu Arg Leu Leu Pro Ala His Leu Ala Leu His Ala Pro Leu Leu Arg
1               5                   10                  15

Leu Leu

<210> SEQ ID NO 70
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 10
<220> FEATURE:
<221> NAME/KEY: MISC_FEATURE
<222> LOCATION: (1)..(1)
```

```
<223> OTHER INFORMATION: CH3CO

<400> SEQUENCE: 70

Leu Arg Leu Leu Ala Ala His Leu Ala Leu His Ala Ala Leu Leu Arg
1               5                   10                  15

Leu Leu

<210> SEQ ID NO 71
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 11
<220> FEATURE:
<221> NAME/KEY: MISC_FEATURE
<222> LOCATION: (1)..(1)
<223> OTHER INFORMATION: CH3CO

<400> SEQUENCE: 71

Arg Arg Leu Leu His Ala Leu Leu Ala Leu Leu Ala His Leu Leu Arg
1               5                   10                  15

Arg Leu

<210> SEQ ID NO 72
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 12
<220> FEATURE:
<221> NAME/KEY: MISC_FEATURE
<222> LOCATION: (1)..(1)
<223> OTHER INFORMATION: CH3CO

<400> SEQUENCE: 72

Arg Arg Leu Leu His Ala Pro Leu Ala Leu Pro Ala His Leu Leu Arg
1               5                   10                  15

Arg Leu

<210> SEQ ID NO 73
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 13
<220> FEATURE:
<221> NAME/KEY: MISC_FEATURE
<222> LOCATION: (1)..(1)
<223> OTHER INFORMATION: CH3CO

<400> SEQUENCE: 73

Arg Arg Leu Leu His Ala Ala Leu Ala Leu Ala Ala His Leu Leu Arg
1               5                   10                  15

Arg Leu

<210> SEQ ID NO 74
<211> LENGTH: 18
<212> TYPE: PRT
<213> ORGANISM: Artificial Sequence
<220> FEATURE:
<223> OTHER INFORMATION: synthetic peptide
```

```
<220> FEATURE:
<223> OTHER INFORMATION: PEPTIDE 14
<220> FEATURE:
<221> NAME/KEY: MISC_FEATURE
<222> LOCATION: (1)..(1)
<223> OTHER INFORMATION: CH3CO

<400> SEQUENCE: 74

Arg Arg Leu Leu Pro Ala His Leu Ala Leu His Ala Pro Leu Leu Arg
 1               5                  10                  15

Arg Leu

<210> SEQ ID NO 75
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 15
<220> FEATURE:
<221> NAME/KEY: MISC_FEATURE
<222> LOCATION: (1)..(1)
<223> OTHER INFORMATION: CH3CO

<400> SEQUENCE: 75

Arg Arg Leu Leu Ala Ala His Leu Ala Leu His Ala Ala Leu Leu Arg
 1               5                  10                  15

Arg Leu

<210> SEQ ID NO 76
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 16
<220> FEATURE:
<221> NAME/KEY: MISC_FEATURE
<222> LOCATION: (1)..(1)
<223> OTHER INFORMATION: CH3CO

<400> SEQUENCE: 76

Arg Arg Leu Leu His Ala His Leu Ala Leu His Ala His Leu Leu Arg
 1               5                  10                  15

Arg Leu

<210> SEQ ID NO 77
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 17
<220> FEATURE:
<221> NAME/KEY: MISC_FEATURE
<222> LOCATION: (1)..(1)
<223> OTHER INFORMATION: CH3CO

<400> SEQUENCE: 77

Arg Arg Leu Leu His Ala Lys Leu Ala Leu Lys Ala His Leu Leu Arg
 1               5                  10                  15

Arg Leu

<210> SEQ ID NO 78
```

```
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 18
<220> FEATURE:
<221> NAME/KEY: MISC_FEATURE
<222> LOCATION: (1)..(1)
<223> OTHER INFORMATION: CH3CO

<400> SEQUENCE: 78

Arg Arg Leu Leu Lys Ala Lys Leu Ala Leu Lys Ala Lys Leu Leu Arg
1               5                   10                  15

Arg Leu

<210> SEQ ID NO 79
<211> LENGTH: 18
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 19
<220> FEATURE:
<221> NAME/KEY: MISC_FEATURE
<222> LOCATION: (1)..(1)
<223> OTHER INFORMATION: CH3CO

<400> SEQUENCE: 79

Arg Arg Leu Lys Lys Ala Lys Leu Lys Leu Lys Ala Lys Lys Leu Arg
1               5                   10                  15

Arg Leu

<210> SEQ ID NO 80
<211> LENGTH: 20
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 16'
<220> FEATURE:
<221> NAME/KEY: MISC_FEATURE
<222> LOCATION: (1)..(1)
<223> OTHER INFORMATION: CH3CO
<220> FEATURE:
<221> NAME/KEY: MISC_FEATURE
<222> LOCATION: (20)..(20)
<223> OTHER INFORMATION: CH3CO

<400> SEQUENCE: 80

Lys Arg Arg Leu Leu His Ala His Leu Ala Leu His Ala His Leu Leu
1               5                   10                  15

Arg Arg Leu Lys
            20

<210> SEQ ID NO 81
<211> LENGTH: 15
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 11/PEPTIDE 6 ALIGNMNENT

<400> SEQUENCE: 81

Arg Leu Leu His Ala Leu Leu Ala Leu Leu Ala His Leu Leu Arg
```

-continued

```
1               5               10              15

<210> SEQ ID NO 82
<211> LENGTH: 15
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 13/PEPTIDE 8 ALIGNMENT

<400> SEQUENCE: 82

Arg Leu Leu His Ala Ala Leu Ala Leu Ala Ala His Leu Leu Arg
1               5               10              15

<210> SEQ ID NO 83
<211> LENGTH: 15
<212> TYPE: PRT
<213> ORGANISM: Artificial Sequence
<220> FEATURE:
<223> OTHER INFORMATION: synthetic peptide
<220> FEATURE:
<223> OTHER INFORMATION: PEPTIDE 15/PEPTIDE 10 ALIGNMENT

<400> SEQUENCE: 83

Arg Leu Leu Ala Ala His Leu Ala Leu His Ala Ala Leu Leu Arg
1               5               10              15

<210> SEQ ID NO 84
<211> LENGTH: 16
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: MOD_RES
<222> LOCATION: (5)..(5)
<223> OTHER INFORMATION: Ala, Leu or His
<220> FEATURE:
<221> NAME/KEY: MOD_RES
<222> LOCATION: (7)..(7)
<223> OTHER INFORMATION: Ala, Leu or His
<220> FEATURE:
<221> NAME/KEY: MOD_RES
<222> LOCATION: (11)..(11)
<223> OTHER INFORMATION: Ala, Leu or His
<220> FEATURE:
<221> NAME/KEY: MOD_RES
<222> LOCATION: (13)..(13)
<223> OTHER INFORMATION: Ala, Leu or His

<400> SEQUENCE: 84

Arg Arg Leu Leu Xaa Ala Xaa Leu Ala Leu Xaa Ala Xaa Leu Leu Arg
1               5               10              15

<210> SEQ ID NO 85
<211> LENGTH: 4
<212> TYPE: PRT
<213> ORGANISM: Artificial Sequence
<220> FEATURE:
<223> OTHER INFORMATION: SYNTHETIC PEPTIDE

<400> SEQUENCE: 85

Arg Arg Leu Leu
```